United States Patent
Park et al.

(10) Patent No.: US 9,646,113 B2
(45) Date of Patent: May 9, 2017

(54) GENERATION OF A COMPUTERIZED BONE MODEL REPRESENTATIVE OF A PRE-DEGENERATED STATE AND USEABLE IN THE DESIGN AND MANUFACTURE OF ARTHROPLASTY DEVICES

(71) Applicant: Howmedica Osteonics Corporation, Mahwah, NJ (US)

(72) Inventors: Ilwhan Park, Walnut Creek, CA (US); Charlie W. Chi, San Francisco, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 652 days.

(21) Appl. No.: 13/923,093

(22) Filed: Jun. 20, 2013

(65) Prior Publication Data

US 2014/0005997 A1    Jan. 2, 2014

Related U.S. Application Data

(62) Division of application No. 12/111,924, filed on Apr. 29, 2008, now Pat. No. 8,480,679.

(51) Int. Cl.
*A61B 34/10* (2016.01)
*G06F 17/50* (2006.01)
(Continued)

(52) U.S. Cl.
CPC .............. *G06F 17/50* (2013.01); *A61B 17/15* (2013.01); *A61B 34/10* (2016.02); *G06T 17/00* (2013.01);
(Continued)

(58) Field of Classification Search
CPC ........ A61B 2034/101; A61B 2034/102; A61B 2034/105; A61B 2034/104
See application file for complete search history.

(56) References Cited

U.S. PATENT DOCUMENTS 3,195,411 A    7/1965    MacDonald et al.
3,825,151 A    7/1974    Arnaud
(Continued)

FOREIGN PATENT DOCUMENTS

DE    3305237 A1    8/1983
DE    4341367 C1    6/1995
(Continued)

OTHER PUBLICATIONS

U.S. Appl. No. 13/960,498, filed Aug. 6, 2013, Song.
(Continued)

*Primary Examiner* — David Bates
(74) *Attorney, Agent, or Firm* — Polsinelli PC

(57) ABSTRACT

A method of generating a computerized bone model representative of at least a portion of a patient bone in a pre-degenerated state. The method includes: generating at least one image of the patient bone in a degenerated state; identifying a reference portion associated with a generally non-degenerated portion of the patient bone; identifying a degenerated portion associated with a generally degenerated portion of the patient bone; and using information from at least one image associated with the reference portion to modify at least one aspect associated with at least one image associated the generally degenerated portion. The method may further include employing the computerized bone model representative of the at least a portion of the patient bone in the pre-degenerated state in defining manufacturing instructions for the manufacture of a customized arthroplasty jig.

22 Claims, 42 Drawing Sheets

(51) Int. Cl.
*A61B 17/15* (2006.01)
*G06T 17/00* (2006.01)
*G06F 19/00* (2011.01)

(52) U.S. Cl.
CPC .......... *A61B 17/155* (2013.01); *A61B 17/157* (2013.01); *A61B 2034/102* (2016.02); *A61B 2034/105* (2016.02); *A61B 2034/108* (2016.02); *G06F 19/321* (2013.01); *G06F 19/3437* (2013.01)

(56) References Cited

U.S. PATENT DOCUMENTS

| | | |
|---|---|---|
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,035,699 A | 7/1991 | Coates |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,099,846 A | 3/1992 | Hardy |
| 5,122,144 A | 6/1992 | Bert et al. |
| 5,123,927 A | 6/1992 | Duncan et al. |
| 5,133,758 A | 7/1992 | Hollister |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,282,803 A | 2/1994 | Lackey |
| 5,298,115 A | 3/1994 | Leonard |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| 5,514,140 A | 5/1996 | Lackey |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,755,803 A | 5/1998 | Haines et al. |
| 5,768,134 A | 6/1998 | Swaelens et al. |
| 5,769,092 A | 6/1998 | Williamson, Jr. |
| 5,769,859 A | 6/1998 | Dorsey |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia, III et al. |
| 5,908,424 A | 6/1999 | Bertin et al. |
| 5,911,724 A | 6/1999 | Wehrli |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Roble et al. |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |

(56) References Cited

U.S. PATENT DOCUMENTS

| | | |
|---|---|---|
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,799,066 B2 | 9/2004 | Steines et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,955,345 B2 | 10/2005 | Kato |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini |
| D532,515 S | 11/2006 | Buttler et al. |
| 7,141,053 B2 | 11/2006 | Rosa et al. |
| 7,153,309 B2 | 12/2006 | Huebner et al. |
| 7,166,833 B2 | 1/2007 | Smith |
| 7,172,597 B2 | 2/2007 | Sanford |
| 7,174,282 B2 | 2/2007 | Hollister et al. |
| 7,177,386 B2 | 2/2007 | Mostafavi et al. |
| 7,184,814 B2 | 2/2007 | Lang et al. |
| 7,203,628 B1 | 4/2007 | St. Ville |
| 7,235,080 B2 | 6/2007 | Hodorek |
| 7,238,190 B2 | 7/2007 | Schon et al. |
| 7,239,908 B1 | 7/2007 | Alexander et al. |
| 7,258,701 B2 | 8/2007 | Aram et al. |
| 7,275,218 B2 | 9/2007 | Petrella et al. |
| 7,309,339 B2 | 12/2007 | Cusick et al. |
| 7,340,316 B2 | 3/2008 | Spaeth et al. |
| 7,359,746 B2 | 4/2008 | Arata |
| 7,373,286 B2 | 5/2008 | Nikolskiy et al. |
| 7,383,164 B2 | 6/2008 | Aram et al. |
| 7,388,972 B2 | 6/2008 | Kitson |
| 7,392,076 B2 | 6/2008 | de La Barrera |
| 7,393,012 B2 | 7/2008 | Funakura et al. |
| 7,394,946 B2 | 7/2008 | Dewaele |
| 7,429,346 B2 | 9/2008 | Ensign et al. |
| 7,468,075 B2 | 12/2008 | Lang et al. |
| 7,517,365 B2 | 4/2009 | Carignan et al. |
| 7,534,263 B2 | 5/2009 | Burdulis, Jr. et al. |
| 7,542,791 B2 | 6/2009 | Mire et al. |
| 7,547,307 B2 | 6/2009 | Carson et al. |
| 7,548,638 B2 | 6/2009 | Graessner |
| 7,584,080 B2 | 9/2009 | Taylor et al. |
| 7,611,519 B2 | 11/2009 | Lefevre et al. |
| 7,616,800 B2 | 11/2009 | Paik et al. |
| 7,618,421 B2 | 11/2009 | Axelson, Jr. et al. |
| 7,618,451 B2 | 11/2009 | Berez et al. |
| 7,621,744 B2 | 11/2009 | Massoud |
| 7,621,920 B2 | 11/2009 | Claypool et al. |
| 7,630,750 B2 | 12/2009 | Liang et al. |
| 7,634,119 B2 | 12/2009 | Tsougarakis et al. |
| 7,634,306 B2 | 12/2009 | Sarin et al. |
| 7,641,660 B2 | 1/2010 | Lakin et al. |
| 7,641,663 B2 | 1/2010 | Hodorek |
| 7,643,862 B2 | 1/2010 | Schoenefeld |
| 7,658,741 B2 | 2/2010 | Claypool et al. |
| 7,660,623 B2 | 2/2010 | Hunter et al. |
| 7,682,398 B2 | 3/2010 | Croxton et al. |
| 7,693,321 B2 | 4/2010 | Lehtonen-Krause |
| 7,695,520 B2 | 4/2010 | Metzger et al. |
| 7,699,847 B2 | 4/2010 | Sheldon et al. |
| 7,702,380 B1 | 4/2010 | Dean |
| 7,715,602 B2 | 5/2010 | Richard |
| 7,717,956 B2 | 5/2010 | Lang |
| D618,796 S | 6/2010 | Cantu et al. |
| 7,747,305 B2 | 6/2010 | Dean et al. |
| D619,718 S | 7/2010 | Gannoe et al. |
| D622,854 S | 8/2010 | Otto et al. |
| 7,769,429 B2 | 8/2010 | Hu |
| 7,780,672 B2 | 8/2010 | Metzger et al. |
| 7,780,681 B2 | 8/2010 | Sarin et al. |
| 7,787,932 B2 | 8/2010 | Vilsmeier et al. |
| 7,794,467 B2 | 9/2010 | McGinley et al. |
| 7,796,791 B2 | 9/2010 | Tsougarakis et al. |
| 7,799,077 B2 | 9/2010 | Lang et al. |
| D626,234 S | 10/2010 | Otto et al. |
| 7,806,838 B2 | 10/2010 | Tsai et al. |
| 7,806,896 B1 | 10/2010 | Bonutti |
| 7,815,645 B2 | 10/2010 | Haines |
| 7,824,181 B2 | 11/2010 | Sers |
| 7,842,039 B2 | 11/2010 | Hodorek et al. |
| 7,842,092 B2 | 11/2010 | Otto et al. |
| 7,881,768 B2 | 2/2011 | Lang et al. |
| 7,894,650 B2 | 2/2011 | Weng et al. |
| 7,927,335 B2 | 4/2011 | Deffenbaugh et al. |
| 7,935,150 B2 | 5/2011 | Carignan et al. |
| 7,940,974 B2 | 5/2011 | Skinner et al. |
| 7,950,924 B2 | 5/2011 | Brajnovic |
| 7,963,968 B2 | 6/2011 | Dees, Jr. |
| 7,967,868 B2 | 6/2011 | White et al. |
| D642,263 S | 7/2011 | Park |
| 7,974,677 B2 | 7/2011 | Mire et al. |
| 7,981,158 B2 | 7/2011 | Fitz et al. |
| 8,007,448 B2 | 8/2011 | de La Barrera |
| 8,021,368 B2 | 9/2011 | Haines |
| 8,036,729 B2 | 10/2011 | Lang et al. |
| 8,052,623 B2 | 11/2011 | Haimerl et al. |
| 8,059,878 B2 | 11/2011 | Feilkas et al. |
| 8,062,302 B2 | 11/2011 | Lang et al. |
| 8,066,708 B2 | 11/2011 | Lang et al. |
| 8,073,521 B2 | 12/2011 | Liew et al. |
| 8,077,950 B2 | 12/2011 | Tsougarakis et al. |
| 8,083,745 B2 | 12/2011 | Lang et al. |
| 8,086,336 B2 | 12/2011 | Christensen |
| 8,092,465 B2 | 1/2012 | Metzger et al. |
| 8,105,330 B2 | 1/2012 | Fitz et al. |
| 8,112,142 B2 | 2/2012 | Alexander et al. |
| 8,122,582 B2 | 2/2012 | Burdulis, Jr. et al. |
| 8,126,234 B1 | 2/2012 | Edwards et al. |
| 8,126,533 B2 | 2/2012 | Lavallee |
| RE43,282 E | 3/2012 | Alexander et al. |
| 8,133,234 B2 | 3/2012 | Meridew et al. |
| 8,142,189 B2 | 3/2012 | Brajnovic |
| 8,160,345 B2 | 4/2012 | Pavlovskaia et al. |
| 8,167,888 B2 | 5/2012 | Steffensmeier |
| 8,170,641 B2 | 5/2012 | Belcher |
| 8,170,716 B2 | 5/2012 | Coste-Maniere et al. |
| 8,175,683 B2 | 5/2012 | Roose |
| 8,177,850 B2 | 5/2012 | Rudan et al. |
| 8,202,324 B2 | 6/2012 | Meulink et al. |
| 8,206,153 B2 | 6/2012 | Berckmans, III et al. |
| 8,214,016 B2 | 7/2012 | Lavallee et al. |
| 8,221,430 B2 | 7/2012 | Park et al. |
| 8,224,127 B2 | 7/2012 | Woodard et al. |
| 8,231,634 B2 | 7/2012 | Mahfouz et al. |
| 8,234,097 B2 | 7/2012 | Steines et al. |
| 8,241,293 B2 | 8/2012 | Stone et al. |
| 8,265,730 B2 | 9/2012 | Alexander et al. |
| 8,265,949 B2 | 9/2012 | Haddad |
| 8,282,646 B2 | 10/2012 | Schoenefeld et al. |
| 8,290,564 B2 | 10/2012 | Lang et al. |
| 8,306,601 B2 | 11/2012 | Lang et al. |
| 8,311,306 B2 | 11/2012 | Pavlovskaia et al. |
| 8,323,288 B2 | 12/2012 | Zajac |
| 8,331,634 B2 | 12/2012 | Barth et al. |
| 8,337,501 B2 | 12/2012 | Fitz et al. |
| 8,460,302 B2 | 6/2013 | Park et al. |
| 8,460,303 B2 | 6/2013 | Park |
| 8,480,679 B2 | 7/2013 | Park |
| 8,483,469 B2 | 7/2013 | Pavlovskaia et al. |
| D691,719 S | 10/2013 | Park |
| 8,545,509 B2 | 10/2013 | Park et al. |

(56) References Cited

U.S. PATENT DOCUMENTS

| | | | |
|---|---|---|---|
| 8,734,455 B2 | 5/2014 | Park et al. |
| 8,737,700 B2 | 5/2014 | Park et al. |
| 8,777,875 B2 | 7/2014 | Park |
| 8,777,955 B2 | 7/2014 | Park |
| 8,801,719 B2 | 8/2014 | Park et al. |
| 8,801,720 B2 | 8/2014 | Park et al. |
| 8,828,011 B2 | 9/2014 | Park et al. |
| 8,882,779 B2 | 11/2014 | Park et al. |
| 8,961,527 B2 | 2/2015 | Park |
| 8,968,320 B2 | 3/2015 | Park et al. |
| 9,017,336 B2 | 4/2015 | Park et al. |
| 9,265,509 B2 | 2/2016 | Park et al. |
| 2002/0087274 A1* | 7/2002 | Alexander | A61B 5/1114 702/19 |
| 2002/0160337 A1 | 10/2002 | Klein et al. |
| 2002/0183760 A1 | 12/2002 | McGovern |
| 2003/0009167 A1 | 1/2003 | Wozencroft |
| 2003/0055502 A1 | 3/2003 | Lang et al. |
| 2004/0102792 A1 | 5/2004 | Sarin et al. |
| 2004/0102866 A1 | 5/2004 | Harris et al. |
| 2004/0133276 A1 | 7/2004 | Lang et al. |
| 2004/0147927 A1 | 7/2004 | Tsougarakis et al. |
| 2004/0153066 A1 | 8/2004 | Coon et al. |
| 2004/0153087 A1 | 8/2004 | Sanford et al. |
| 2004/0204760 A1 | 10/2004 | Fitz et al. |
| 2004/0220583 A1 | 11/2004 | Pieczynski, II et al. |
| 2004/0243148 A1 | 12/2004 | Wasielewski |
| 2004/0243481 A1 | 12/2004 | Bradbury et al. |
| 2005/0054914 A1 | 3/2005 | Duerk et al. |
| 2005/0059978 A1 | 3/2005 | Sherry et al. |
| 2005/0065617 A1 | 3/2005 | de la Barrera et al. |
| 2005/0080426 A1 | 4/2005 | Qian |
| 2005/0149091 A1 | 7/2005 | Tanamal et al. |
| 2005/0192588 A1 | 9/2005 | Garcia |
| 2005/0245934 A1 | 11/2005 | Tuke et al. |
| 2005/0245936 A1 | 11/2005 | Tuke et al. |
| 2005/0256389 A1 | 11/2005 | Koga et al. |
| 2005/0267584 A1 | 12/2005 | Burdulis, Jr. et al. |
| 2005/0272998 A1 | 12/2005 | Diehl et al. |
| 2006/0015018 A1 | 1/2006 | Jutras et al. |
| 2006/0015030 A1 | 1/2006 | Poulin et al. |
| 2006/0015188 A1 | 1/2006 | Grimes |
| 2006/0079755 A1 | 4/2006 | Stazzone et al. |
| 2006/0110017 A1 | 5/2006 | Tsai et al. |
| 2006/0122491 A1 | 6/2006 | Murray et al. |
| 2006/0155293 A1 | 7/2006 | McGinley et al. |
| 2006/0155294 A1 | 7/2006 | Steffensmeier et al. |
| 2006/0161167 A1 | 7/2006 | Myers |
| 2006/0195113 A1 | 8/2006 | Masini |
| 2006/0244448 A1 | 11/2006 | Ballon et al. |
| 2006/0271058 A1 | 11/2006 | Ashton et al. |
| 2007/0010732 A1 | 1/2007 | DeYoe et al. |
| 2007/0021838 A1 | 1/2007 | Dugas et al. |
| 2007/0038059 A1 | 2/2007 | Sheffer et al. |
| 2007/0055268 A1 | 3/2007 | Utz et al. |
| 2007/0073305 A1 | 3/2007 | Lionberger et al. |
| 2007/0083266 A1 | 4/2007 | Lang |
| 2007/0100338 A1 | 5/2007 | Deffenbaugh et al. |
| 2007/0100462 A1 | 5/2007 | Lang et al. |
| 2007/0114370 A1 | 5/2007 | Smith et al. |
| 2007/0118055 A1 | 5/2007 | McCombs |
| 2007/0118243 A1 | 5/2007 | Schroeder et al. |
| 2007/0123856 A1 | 5/2007 | Deffenbaugh et al. |
| 2007/0123857 A1 | 5/2007 | Deffenbaugh et al. |
| 2007/0123912 A1 | 5/2007 | Carson |
| 2007/0162039 A1 | 7/2007 | Wozencroft |
| 2007/0167833 A1 | 7/2007 | Redel et al. |
| 2007/0173853 A1 | 7/2007 | MacMillan |
| 2007/0173858 A1 | 7/2007 | Engh et al. |
| 2007/0191741 A1 | 8/2007 | Tsai et al. |
| 2007/0213738 A1 | 9/2007 | Martin et al. |
| 2007/0226986 A1 | 10/2007 | Park et al. |
| 2007/0232959 A1 | 10/2007 | Couture et al. |
| 2007/0233136 A1 | 10/2007 | Wozencroft |
| 2007/0233141 A1 | 10/2007 | Park et al. |
| 2007/0233269 A1 | 10/2007 | Steines et al. |
| 2007/0237372 A1 | 10/2007 | Chen et al. |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2008/0004701 A1 | 1/2008 | Axelson et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson et al. |
| 2008/0015606 A1 | 1/2008 | D'Alessio et al. |
| 2008/0015607 A1 | 1/2008 | D'Alessio et al. |
| 2008/0021299 A1 | 1/2008 | Meulink |
| 2008/0033442 A1 | 2/2008 | Amiot et al. |
| 2008/0058613 A1 | 3/2008 | Lang et al. |
| 2008/0088761 A1 | 4/2008 | Lin et al. |
| 2008/0089591 A1 | 4/2008 | Zhou et al. |
| 2008/0114370 A1 | 5/2008 | Schoenefeld |
| 2008/0147072 A1 | 6/2008 | Park et al. |
| 2008/0153067 A1 | 6/2008 | Berckmans et al. |
| 2008/0195108 A1 | 8/2008 | Bhatnagar et al. |
| 2008/0208081 A1 | 8/2008 | Murphy |
| 2008/0232661 A1 | 9/2008 | Habets |
| 2008/0234685 A1 | 9/2008 | Gjerde |
| 2008/0257363 A1 | 10/2008 | Schoenefeld et al. |
| 2008/0275452 A1 | 11/2008 | Lang et al. |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0085567 A1 | 4/2009 | Kimmlingen et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aaram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0093816 A1 | 4/2009 | Roose et al. |
| 2009/0110498 A1 | 4/2009 | Park |
| 2009/0112213 A1 | 4/2009 | Heavener et al. |
| 2009/0125114 A1 | 5/2009 | May et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0151736 A1 | 6/2009 | Belcher et al. |
| 2009/0163923 A1 | 6/2009 | Flett et al. |
| 2009/0209884 A1 | 8/2009 | Van Vorhis et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0276045 A1 | 11/2009 | Lang |
| 2009/0285465 A1 | 11/2009 | Haimerl et al. |
| 2009/0306676 A1 | 12/2009 | Lang et al. |
| 2009/0312805 A1 | 12/2009 | Lang et al. |
| 2010/0016986 A1 | 1/2010 | Trabish |
| 2010/0023015 A1 | 1/2010 | Park |
| 2010/0036252 A1 | 2/2010 | Chalana et al. |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0099977 A1 | 4/2010 | Hershberger |
| 2010/0145344 A1 | 6/2010 | Jordan et al. |
| 2010/0152741 A1 | 6/2010 | Park et al. |
| 2010/0153076 A1 | 6/2010 | Bellettre et al. |
| 2010/0153081 A1 | 6/2010 | Bellettre et al. |
| 2010/0160917 A1 | 6/2010 | Fitz et al. |
| 2010/0168754 A1 | 7/2010 | Fitz et al. |

(56) References Cited

U.S. PATENT DOCUMENTS

| | | |
|---|---|---|
| 2010/0174376 A1 | 7/2010 | Lang |
| 2010/0191242 A1 | 7/2010 | Massoud |
| 2010/0191244 A1 | 7/2010 | White et al. |
| 2010/0198351 A1 | 8/2010 | Meulink |
| 2010/0209868 A1 | 8/2010 | De Clerck |
| 2010/0228257 A1 | 9/2010 | Bonutti |
| 2010/0256479 A1 | 10/2010 | Park et al. |
| 2010/0274253 A1 | 10/2010 | Ure |
| 2010/0274534 A1 | 10/2010 | Steines et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0324692 A1 | 12/2010 | Uthgenannt et al. |
| 2010/0329530 A1 | 12/2010 | Lang et al. |
| 2011/0015636 A1 | 1/2011 | Katrana et al. |
| 2011/0016690 A1 | 1/2011 | Narainasamy et al. |
| 2011/0029093 A1 | 2/2011 | Bojarski et al. |
| 2011/0029116 A1 | 2/2011 | Jordan et al. |
| 2011/0046735 A1 | 2/2011 | Metzger et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071537 A1 | 3/2011 | Koga et al. |
| 2011/0071581 A1 | 3/2011 | Lang et al. |
| 2011/0087332 A1 | 4/2011 | Bojarski et al. |
| 2011/0087465 A1 | 4/2011 | Mahfouz |
| 2011/0092804 A1 | 4/2011 | Schoenefeld et al. |
| 2011/0092977 A1 | 4/2011 | Salehi et al. |
| 2011/0092978 A1 | 4/2011 | McCombs |
| 2011/0112808 A1 | 5/2011 | Anderson et al. |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0184526 A1 | 7/2011 | White et al. |
| 2011/0190775 A1 | 8/2011 | Ure |
| 2011/0190899 A1 | 8/2011 | Pierce et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0004725 A1 | 1/2012 | Shterling et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0143197 A1 | 6/2012 | Lang et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165821 A1 | 6/2012 | Carignan et al. |
| 2012/0172882 A1 | 7/2012 | Sato |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0265499 A1 | 10/2012 | Mahfouz et al. |
| 2012/0310400 A1 | 12/2012 | Park |
| 2013/0039551 A1 | 2/2013 | Pavlovskaia et al. |
| 2013/0115474 A1 | 5/2013 | Park |
| 2013/0116697 A1 | 5/2013 | Park et al. |
| 2013/0123789 A1 | 5/2013 | Park |
| 2013/0190767 A1 | 7/2013 | Park et al. |
| 2013/0345845 A1 | 12/2013 | Park et al. |
| 2014/0078139 A1 | 3/2014 | Park et al. |
| 2014/0081277 A1 | 3/2014 | Park et al. |
| 2014/0128875 A1 | 5/2014 | Park et al. |
| 2014/0324205 A1 | 10/2014 | Park et al. |
| 2014/0330278 A1 | 11/2014 | Park et al. |
| 2014/0330279 A1 | 11/2014 | Park et al. |
| 2014/0378978 A1 | 12/2014 | Park |
| 2016/0015466 A1 | 1/2016 | Park et al. |
| 2016/0095609 A1 | 4/2016 | Park et al. |

FOREIGN PATENT DOCUMENTS

| | | |
|---|---|---|
| DE | 102005023028 A1 | 11/2006 |
| EP | 0097001 A | 12/1983 |
| EP | 0574098 A | 12/1993 |
| EP | 0622052 A | 11/1994 |
| EP | 0709061 A1 | 5/1996 |
| EP | 0908836 A2 | 4/1999 |
| EP | 0908836 A3 | 12/1999 |
| EP | 1059153 A2 | 12/2000 |
| EP | 1486900 A1 | 12/2004 |
| EP | 1532939 A1 | 5/2005 |
| EP | 1669033 A1 | 6/2006 |
| FR | 2478462 A1 | 9/1981 |
| GB | 2215610 A1 | 9/1989 |
| GB | 2420717 A | 6/2006 |
| GB | 2447702 A | 9/2008 |
| JP | 10-94538 | 4/1998 |
| JP | 2001-092950 | 4/2001 |
| JP | 2005-287813 | 10/2005 |
| WO | WO 93/25157 A1 | 12/1993 |
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO 98/32384 | 7/1998 |
| WO | WO 00/35346 | 6/2000 |
| WO | WO 01/00096 A1 | 1/2001 |
| WO | WO 01/70142 A1 | 9/2001 |
| WO | WO 01/85040 A1 | 11/2001 |
| WO | WO 02/096268 A2 | 12/2002 |
| WO | WO 2004/032806 A1 | 4/2004 |
| WO | WO 2004/049981 A2 | 6/2004 |
| WO | WO 2005/051240 A1 | 6/2005 |
| WO | WO 2005/087125 A2 | 9/2005 |
| WO | WO 2005/099636 A1 | 10/2005 |
| WO | WO 2006/058057 A2 | 6/2006 |
| WO | WO 2006/060795 A1 | 6/2006 |
| WO | WO 2006/092600 A1 | 9/2006 |
| WO | WO 2006/127486 A2 | 11/2006 |

(56) References Cited

FOREIGN PATENT DOCUMENTS

| | | |
|---|---|---|
| WO | WO 2006/134345 A1 | 12/2006 |
| WO | WO 2007/014164 A2 | 2/2007 |
| WO | WO 2007/058632 A1 | 5/2007 |
| WO | WO 2007/092841 A2 | 8/2007 |
| WO | WO 2007/097853 A2 | 8/2007 |
| WO | WO 2007/097854 A2 | 8/2007 |
| WO | WO 2007/137327 A1 | 12/2007 |
| WO | WO 2008/014618 A1 | 2/2008 |
| WO | WO 2008/091358 A1 | 7/2008 |

OTHER PUBLICATIONS

U.S. Appl. No. 14/011,998, filed Aug. 28, 2013, Park et al.
Advisory Action and Interview Summary, U.S. Appl. No. 12/390,667, mailed Apr. 27, 2012, 23 pages.
Advisory Action, U.S. Appl. No. 11/642,385, dated Oct. 29, 2010, 3 pages.
Akca, "Matching of 3D Surfaces and Their Intensities," ISPRS Journal of Photogrammetry & Remote Sensing, 62(2007), 112-121.
Akenine-Möller et al., *Real-Time Rendering, Second Edition*, AK Peters, Natick, MA, 6 pages (Table of Contents), 2002.
Amendment and Response to Ex Parte Quayle Action, U.S. Appl. No. 29/296,687 dated Mar. 24, 2011, 17 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Non-Final Office Action, U.S. Appl. No. 11/959,344, dated Jul. 15, 2011, 13 pages.
Amendment and Response to Office Action and Petition to Revive, U.S. Appl. No. 10/146,862, filed Jan. 18, 2006, 29 pages.
Amendment and Response to Office Action, U.S. Appl. No. 11/656,323, filed Jun. 25, 2010, 7 pages.
Amendment and Response to Office Action, U.S. Appl. No. 11/641,569, dated Feb. 5, 2010, 20 pages.
Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response to Restriction/Election Requirement, U.S. Appl. No. 11/656,323, filed Dec. 8, 2009, 6 pages.
Amendment and Response, U.S. Appl. No. 11/642,385, filed May 28, 2010, 11 pages.
Amendment Under 37 C.F.R. 1.312, U.S. Appl. No. 12/386,105, filed Oct. 1, 2012, 6 pages.
Amendment Under 37 C.F.R. 1.312, U.S. Appl. No. 13/374,960, filed May 7, 2013, 6 pages.
Appeal Brief, U.S. Appl. No. 12/390,667, filed Jul. 12, 2012, 32 pages.
Appeal Brief, U.S. Appl. No. 12/391,008, filed Oct. 16, 2012, 24 pages.
Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.
Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.
Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.
Barequet et al., "Filling Gaps in the Boundary of a Polyhedron," *Computer Aided Geometric Design*, vol. 12, pp. 207-229, 1995.
Barequet et al., "Repairing CAD Models," Proceedings of the 8th IEEE Visualization '97 Conference, pp. 363-370, Oct. 1997.
Bargar et al., "Robotic Systems in Surgery," Orthopedic and Spine Surgery, Surgical Technology International II, 1993, 419-423.
Berry et al., "Personalised image-based templates for intra-operative guidance," *Proc. Inst. Mech. Eng. Part H: J. Engineering in Medicine*, vol. 219, pp. 111-118, Oct. 7, 2004.
Besl et al., "A Method for Registration of 3-D Shapes," IEEE Transactions on Pattern Analysis and Machine Intelligence (PAMI), 14(2):239-256, Feb. 1992.
Biščević et al., "Variations of Femoral Condyle 2005 Shape," *Coll. Antropol.*, vol. 29 No. 2, pp. 409-414, 2005.
Blaha et al., "Using the Transepicondylar Axis to Define the Sagittal Morphology of the Distal Part of the Femur," J Bone Joint Surg Am. 2002;84-A Suppl 2:48-55.
Blinn, *Jim Blinn's Corner—A Trip Down the Graphics Pipeline*, Morgan Kaufmann Publishers, Inc., San Francisco, CA, 5 pages (Table of Contents), 1996.
Bøhn et al., "A Topology-Based Approach for Shell-Closure," *Geometric Modeling for Product Realization* (P.R. Wilson et al. editors), pp. 297-319, Elsevier Science Publishers B.V., North-Holland, 1993.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.
Canny, "A computational Approach to Edge Detection," IEEE Transactions on Pattern Analysis and Machine Intelligence, PAMI 8(6), pp. 679-698 (1986).
Chauhan et al., "Computer-assisted knee arthroplasty versus a conventional jig-based technique—a randomised, prospective trial," *The Journal of Bone and Joint Surgery*, vol. 86-B, No. 3, pp. 372-377, Apr. 2004.
Churchill et al., "The Transepicondylar Axis Approximates the Optimal Flexion Axis of the Knee," Clin Orthop Relat Res. 1998(356):111-8.
Cicuttini et al., "Gender Differences in Knee Cartilage Volume as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume in Subjects with Knee Osteoarthritis," Rheumatology (Oxford) 2004, 43:321-4.
Cohen et al., *Radiosity and Realistic Image Synthesis*, Academic Press Professional, Cambridge, MA, 8 pages (Table of Contents), 1993.
Couglin et al., "Tibial Axis and Patellar Position Relative to the Femoral Epicondylar Axis During Squatting," *The Journal of Arthroplasty*, vol. 18, No. 8, Elsevier, 2003.
Delp et al., "Computer Assisted Knee Replacement," *Clinical Orthopaedics and Related Research*, No. 354, pp. 49-56, Sep. 1998.
Dutré et al., *Advanced Global Illumination*, AK Peters, Natick, MA, 5 pages (Table of Contents), 2003.
Eckhoff et al., "Difference Between the Epicondylar and Cylindrical Axis of the Knee," Clin Orthop Relat Res. 2007;461:238-44.
Eckhoff et al., "Three-Dimensional Mechanics, Kinematics, and Morphology of the Knee Viewed in Virtual Realty," *The Journal of Bone and Joint Surgery*, vol. 87-A, Supplement 2, pp. 71-80, 2005.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).
Eisenhart-Rothe et al., "The Role of Knee alignment in Disease Progression and Functional Decline in Knee Osteoarthritis," JAMA 2001, 286:188-95.

(56) References Cited

OTHER PUBLICATIONS

Elias et al., "A Correlative Study of the Geometry and anatomy of the Distal Femur," Clin orthop Relat Res. 1990(260):98-103.
Erikson, "Error Correction of a Large Architectural Model: The Henderson County Courthouse," Technical Report TR95-013, Dept. of Computer Science, University of North Carolina at Chapel Hill, pp. 1-11, 1995.
Ervin et al., *Landscape Modeling*, McGraw-Hill, New York, NY, 8 pages (Table of Contents), 2001.
European Search Report, 10192631.9-2310, dated Mar. 17, 2011, 5 pages.
Ex Parte Quayle Action, U.S. Appl. No. 29/296,687, mailed Jan. 24, 2011, 11 pages.
Examiner's Answer in appeal, U.S. Appl. No. 12/391,008, mailed Dec. 13, 2012, 27 pages.
Farin, *NURB Curves and Surfaces: From Projective Geometry to Practical Use*, AK Peters, Wellesley, MA, 7 pages (Table of Contents), 1995.
Favorito et al., "total Knee Arthroplasty in the Valgus Knee," Journal Am Acad Orthop surg. 2002;10(1):16-24.
Final Office Action, U.S. Appl. No. 11/641,382, mailed Aug. 5, 2010, 13 pages.
Final Office Action, U.S. Appl. No. 11/656,323, mailed Sep. 3, 2010, 11 pages.
Final Office Action, U.S. Appl. No. 11/641,569, mailed May 10, 2010, 9 pages.
Final Office Action, U.S. Appl. No. 11/959,344, mailed Oct. 27, 2011, 12 pages.
Final Office Action, U.S. Appl. No. 12/390,667, mailed Jan. 13, 2012, 27 pages.
Final Office Action, U.S. Appl. No. 12/546,545, dated Dec. 20, 2012, 16 pages.
Final Office Action, U.S. Appl. No. 12/636,939, mailed Jan. 25, 2013, 9 pages.
Final Office Action, U.S. Appl. No. 11/641,382, mailed Jul. 25, 2012, 12 pages.
Final Office Action, U.S. Appl. No. 11/641,569, mailed Mar. 1, 2012, 12 pages.
Final Office Action, U.S. Appl. No. 11/924,425, mailed Jul. 6, 2012, 14 pages.
Final Office Action, U.S. Appl. No. 11/946,002, mailed May 9, 2012, 24 pages.
Final Office Action, U.S. Appl. No. 12/391,008, mailed May 17, 2012, 28 pages.
Final Office Action, U.S. Appl. No. 12/563,809, mailed Mar. 7, 2013, 14 pages.
Fleischer et al., "Accurate Polygon Scan Conversion Using Half-Open Intervals," *Graphics Gems III*, pp. 362-365, code: pp. 599-605, 1992.
Foley et al., *Computer Graphics: Principles and Practice*, Addison-Wesley Publishing Company, Reading, MA, 9 pages (Table of Contents), 1990.
Freeman et al., "The Movement of the Knee Studied by Magnetic Resonance Imaging," Clinical orthop Relat Res. 2003(410):35-43.
Freeman et al., "The Movement of the Normal Tibio-Femoral Joint," Journal Biomech. 2005;38(2):197-208.
Glassner (editor), *An Introduction to Ray Tracing*, Academic Press Limited, San Diego, CA, 4 pages (Table of Contents), 1989.
Glassner, *Principles of Digital Image Synthesis*, vols. One and Two, Morgan Kaufmann Publishers, Inc., San Francisco, CA, 32 pages (Table of Contents), 1995.
Gooch et al., *Non-Photorealistic Rendering*, AK Peters, Natick, MA, 4 pages (Table of Contents), 2001.
Graichen et al., "Quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.
Gruen et al., "Least Squares 3D Surface and Curve Matching," ISPRS Journal of Photogrammetry & Remote Sensing, 59(2005), 151-174.
Grüne et al., "On numerical algorithm and interactive visualization for optimal control problems," *Journal of Computation and Visualization in Science*, vol. 1, No. 4, pp. 221-229, Jul. 1999.
Guéziec et al., "Converting Sets of Polygons to Manifold Surfaces by Cutting and Stitching," Proc. IEEE Visualization 1998, pp. 383-390, Oct. 1998.
Hafez et al., "Computer Assisted Total Knee Replacement: Could a Two-Piece Custom Template Replace the Complex Conventional Instrumentations?", *Computer Aided Surgery*, vol. 9, No. 3, pp. 93-94, 2004.
Hafez et al., "Computer-Assisted Total Knee Arthroplasty Using Patient-Specific Templating," *Clinical Orthopaedics and Related Research*, No. 0, pp. 1-9, 2006.
Hafez et al., "Patient Specific Instrumentation for TKA: Testing the Reliability Using a Navigational System," MIS Meets CAOS Symposium & Instructional Academy, Less and Minimally Invasive Surgery for Joint Arthroplasty: Fact and Fiction Syllabus, San Diego, CA, 8 pages, Oct. 20-22, 2005.
Hollister et al., "The Axes of Rotation of the Knee," Clin Orthop Relat Res. 1993(290):259-68.
Howell et al., "In Vivo Adduction and Reverse Axial Rotation (External) of the Tibial Component can be Minimized During Standing and Kneeling," Orthopedics|ORTHOSupersite.com vol. 32 No. 5, 319-326 (May 2009).
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
International Search Report and Written Opinion, International Application No. PCT/US2009/034983, mailed May 22, 2009, 15 pages.
International Search Report and Written Opinion, International Application No. PCT/US2009/034967, mailed Jun. 16, 2009, 15 pages.
International Search Report and Written Opinion, International Application No. PCT/US2009/041519, mailed Jun. 17, 2009, 10 pages.
International Search Report and Written Opinion, International Application No. PCT/US2009/040629, mailed Aug. 6, 2009, 9 pages.
International Search Report and Written Opinion, International Application No. PCT/US2009/051109, mailed Nov. 6, 2009, 13 pages.
International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.
International Search Report and Written Opinion, PCT/US2007/001624, dated Dec. 12, 2007, 14 pages.
International Search Report and Written Opinion, PCT/US2007/001622, dated Jun. 11,2007, 14 pages.
International Search Report and Written Opinion, PCT/US2008/083125, dated Mar. 9, 2009, 13 pages.
International Search Report and Written Opinion, PCT/US2011/032342, dated Jul. 1, 2011, 8 pages.
Invitation to Pay Additional Fees mailed on Jul. 31, 2007, for PCT Application No. PCT/US2007/001624 filed on Jan. 19, 2007, 5 pages.
Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jacobs et al., "Hip Resurfacing Through an Anterolateral Approach," J. Bone Joint Surg Am. 2008:90 Suppl 3:38-44.
Jensen, *Realistic Image Synthesis Using Photon Mapping*, AK Peters, Natick, MA, 7 pages (Table of Contents), 2001.
Johnson, "Joint Remodeling as the Basis for Osteoarthritis," Journal Am Vet Med Assoc. 1962, 141:1233-41.

(56) References Cited

OTHER PUBLICATIONS

Jones et al., "A new approach to the construction of surfaces from contour data," *Computer Graphics Forum*, vol. 13, No. 3, pp. 75-84, 1994 [ISSN 0167-7055].
Kass et al., "Active Contour Models," International Journal of Computer Vision, pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.
Khorramabadi, "A Walk Through the Planned CS Building," Technical Report UCB/CSD 91/652, Computer Science Department, University of California at Berkeley, 74 pages, 1991.
Kidder et al., "3-D Model Acquisition, Design, Planning and Manufacturing of Orthopaedic Devices: A Framework," *Advanced Sensor and Control-System Interface* (B.O. Nnaji editor), Proceedings SPIE—The International Society for Optical Engineering, Bellingham, WA, vol. 2911, pp. 9-22, Nov. 21-22, 1996.
Kienzel III et al., "An Integrated CAD-Robotics System for Total Knee Replacement Surgery", IEEE International Conference, pp. 889-894, vol. 1, May 1993.
Kienzel III et al., "Total Knee Replacement," IEEE May/Jun. 1995.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.
Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Kumar, *Robust Incremental Polygon Triangulation for Surface Rendering*, Center for Geometric Computing, Department of Computer Science, Johns Hopkins University, Baltimore, MD, WSCG, The International Conference in Central Europe on Computer Graphics, Visualization and Computer Vision, pp. 381-388, 2000.
Kunz et al., "Computer Assisted Hip Resurfacing Using Individualized Drill Templates," *The Journal of Arthroplasty*, vol. 00, No. 0, pp. 1-7, 2009.
Kusumoto et al., "Application of Virtual Reality Force Feedback Haptic Device for Oral Implant Surgery", Graduate School of Dentistry Course for Integrated Oral Science and Stomatology, Jun. 16, 2005.
Lea et al., "Registration and immobilization in robot-assisted surgery", Journal of Image Guided Surgery, pp. 1-10, 1995.
Lorensen et al., "Marching Cubes: A High Resolution 3d Surface Construction Algorithm," *Computer Graphics*, vol. 21, No. 4, pp. 163-169, 1987.
Manner et al., "Knee Deformity in Congenital Longitudinal Deficiencies of the Lower Extremity," Clin Orthop Relat Res. 2006;448:185-92.
Matsuda et al., "Anatomical Analysis of the Femoral Condyle in Normal and Osteoarthritic Knees," Journal Orthopaedic Res. 2004;22(1):104-9.
Matsuda et al., "Femoral Condyle Geometry in the Normal and Varus Knee," Clinical Orthop Relat Res. 1998(349):183-8.
Messmer et al., "Volumetric Determination of the Tibia Based on 2d Radiographs Using A 2d/3d Database", Dept. of Surgery, Trauma Unit, University Hospital, Bassel, Switzerland, *Computer Aided Surgery* 6:183-194 (2001).
Mihalko et al., The Variability of Intramedullary Alignment of the Femoral Component During Total Knee Arthroplasty, Journal Arthroplasty. 2005;20(1):25-8.
Mole et al., "A New Three-Dimensional Treatment Algorithm for Complex Surfaces: Applications in Surgery", Feb. 1995.
Morvan et al., IVECS, Interactively Correcting .STL Files in a Virtual Environment, Clemson University, Clemson, SC, Proc. Conf. Virtual Design, Aug. 1996.
Non-Final Office Action, U.S. Appl. No. 11/641,382, mailed Jan. 20, 2010, 12 pages.
NonFinal Office Action, U.S. Appl. No. 11/642,385, mailed Mar. 2, 2010, 11 pages.
Non-Final Office Action, U.S. Appl. No. 11/656,323, mailed Mar. 30, 2010, 10 pages.
Non-Final Office Action, U.S. Appl. No. 11/641,569, dated Aug. 3, 2011, 14 pages.
Non-Final Office Action, U.S. Appl. No. 11/641,569, dated Jan. 3, 2013, 12 pages.
Non-Final Office Action, U.S. Appl. No. 11/924,425, mailed Jan. 25, 2012, 35 pages.
Non-Final Office Action, U.S. Appl. No. 12/390,667, dated Aug. 24, 2011, 49 pages.
Non-Final Office Action, U.S. Appl. No. 13/086,275, mailed Feb. 7, 2013, 36 pages.
Non-Final Office Action, U.S. Appl. No. 11/641,382, mailed Mar. 29, 2012, 24 pages.
NonFinal Office Action, U.S. Appl. No. 11/641,569, mailed Nov. 12, 2009, 9 pages.
Non-Final Office Action, U.S. Appl. No. 11/946,002, dated Nov. 25, 2011, 44 pages.
Nonfinal Office Action, U.S. Appl. No. 11/959,344, dated Feb. 15, 2011, 29 pages.
Non-Final Office Action, U.S. Appl. No. 12/111,924, mailed Jun. 29, 2012, 35 pages.
Non-Final Office Action, U.S. Appl. No. 12/386,105, dated Feb. 9, 2012, 30 pages.
Non-Final Office Action, U.S. Appl. No. 12/390,667, mailed Sep. 26, 2012, 21 pages.
Non-Final Office Action, U.S. Appl. No. 12/390,667, mailed May 8, 2013, 20 pages.
Non-Final Office Action, U.S. Appl. No. 12/391,008, mailed Oct. 31, 2011, 44 pages.
Non-Final Office Action, U.S. Appl. No. 12/546,545, mailed Jul. 19, 2012, 28 pages.
Non-Final Office Action, U.S. Appl. No. 12/546,545, mailed Mar. 13, 2013, 10 pages.
Non-Final Office Action, U.S. Appl. No. 12/563,809, mailed Sep. 21, 2012, 32 pages.
Non-Final Office Action, U.S. Appl. No. 12/636,939, mailed Jul. 20, 2012, 25 pages.
Non-Final Office Action, U.S. Appl. No. 12/636,939, mailed Apr. 25, 2013, 16 pages.
Non-Final Office Action, U.S. Appl. No. 13/374,960, mailed Aug. 1, 2012, 6 pages.
Nooruddin et al., Simplification and Repair of Polygonal Models Using Volumetric Techniques, *IEEE Transactions on Visualization and Computer Graphics*, vol. 9, No. 2, pp. 191-205, Apr.-Jun. 2003.
Notice of Allowance, U.S. Appl. No. 12/111,924, dated Dec. 24, 2012, 10 pages.
Notice of Allowance, U.S. Appl. No. 13/066,568, mailed Oct. 26, 2011, 28 pages.
Notice of Allowance, U.S. Appl. No. 11/641,382, mailed Oct. 9, 2012, 9 pages.
Notice of Allowance, U.S. Appl. No. 11/924,425, mailed Sep. 25, 2012, 18 pages.
Notice of Allowance, U.S. Appl. No. 11/959,344, mailed Mar. 5, 2012, 13 pages.
Notice of Allowance, U.S. Appl. No. 12/111,924, mailed Mar. 11, 2013, 14 pages.
Notice of Allowance, U.S. Appl. No. 12/386,105, mailed Jul. 5, 2012, 11 pages.
Notice of Allowance, U.S. Appl. No. 12/563,809, mailed May 28, 2013, 11 pages.
Notice of Allowance, U.S. Appl. No. 13/374,960, mailed Nov. 2, 2012, 24 pages.
Notice of Allowance, U.S. Appl. No. 13/374,960, mailed May 6, 2013, 20 pages.
Notice of Allowance, U.S. Appl. No. 13/573,662, mailed Mar. 19, 2013, 34 pages.
Notice of Allowance, U.S. Appl. No. 29/296,687, mailed Mar. 31, 2011, 18 pages.

(56) References Cited

OTHER PUBLICATIONS

Notice of Non-Compliant Amendment, U.S. Appl. No. 11/641,569, mailed Aug. 7, 2009, 3 pages.
Office Action (Restriction Requirement), U.S. Appl. No. 12/563,809, dated Feb. 2, 2012, 7 pages.
Office Action, U.S. Appl. No. 10/146,862, mailed Jan. 13, 2005, 10 pages.
Panjabi et al., "Errors in Kinematic Parameters of a Planar Joint: Guidelines for Optimal Experimental Design," Journal Biomech. 1982;15(7):537-44.
Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.
Peterfy et al., "Quantification of articular Cartilage in the Knee with Pulsed Saturation Transfer Subtraction and Fact-Suppressed MR Imaging: Optimization and Validation," Radiology 1994, 192:485-91.
Pinskerova et al., "The Shapes and Relative Movements of the Femur and Tibia at the Knee," Orthopaedics 2000;29 Suppl 1:S3-5.
Platt et al., "Mould Arthroplasty of the Knee, A Ten-Year Follow-up Study," *The Journal of Bone and Joint Surgery* (British Volume), vol. 51-B, No. 1, pp. 76-87, Feb. 1969.
Potter, "Arthroplasty of the Knee with Metallic Implants of the McKeever and Macintosh Tibial Design," *The Surgical Clinics of North America*, vol. 49, No. 4, pp. 903-915, Aug. 1969.
Preliminary Amendment, U.S. Appl. No. 11/641,569, dated Aug. 14, 2008, 13 pages.
Preliminary Amendment, U.S. Appl. No. 11/642,385, filed Aug. 22, 2008, 42 pages.
Preliminary Amendment, U.S. Appl. No. 13/731,697, filed May 10, 2013, 6 pages.
Radermacher et al., "Computer Assisted Orthopaedic Surgery with Image Based Individual Templates," *Clinical Orthopaedics and Related Research*, vol. 354, pp. 28-38, Sep. 1998.
RCE/Amendment, U.S. Appl. No. 11/641,569, filed Aug. 9, 2010, 18 pages.
RCE/Amendment, U.S. Appl. No. 11/642,382, filed Oct. 26, 2010, 14 pages.
RCE/Amendment, U.S. Appl. No. 11/642,385, filed Dec. 6, 2010, 13 pages.
RCE/Amendment, U.S. Appl. No. 11/656,323, filed Nov. 19, 2010, 12 pages.
RCE/Amendment, U.S. Appl. No. 11/946,002, filed Sep. 6, 2012, 38 pages.
Response to Final Office Action, U.S. Appl. No. 11/641,569, filed Jun. 28, 2012, 10 pages.
Response to Final Office Action, U.S. Appl. No. 11/641,382, filed Sep. 24, 2012, 11 pages.
Response to Final Office Action, U.S. Appl. No. 11/959,344, filed Dec. 27, 2011, 16 pages.
Response to Final Office Action, U.S. Appl. No. 11/924,425, filed Sep. 5, 2012, 9 pages.
Response to Final Office Action, U.S. Appl. No. 12/390,667, filed Mar. 12, 2012, 19 pages.
Response to Final Office Action, U.S. Appl. No. 12/563,809, filed May 6, 2013, 15 pages.
Response to Final Office Action, U.S. Appl. No. 12/636,939, filed Apr. 8, 2013, 10 pages.
Response to Non-Final Office Action, U.S. Appl. No. 12/563,809, filed Dec. 13, 2012, 15 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Non-Final Office Action, U.S. Appl. No. 11/924,425, filed Apr. 25, 2012, 8 pages.
Response to Non-Final Office Action, U.S. Appl. No. 12/386,105, filed Jun. 8, 2012, 13 pages.
Response to Non-Final Office Action, U.S. Appl. No. 11/641,382, filed Jun. 27, 2012, 12 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
Response to Non-Final Office Action, U.S. Appl. No. 11/641,569, filed Apr. 3, 2013, 9 pages.
Response to Non-Final Office Action, U.S. Appl. No. 13/086,275, filed May 7, 2013, 11 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Response to Restriction Requirement, U.S. Appl. No. 11/959,344, filed Nov. 24, 2010, 13 pages.
Response to Restriction Requirement, U.S. Appl. No. 12/390,667, dated Jul. 27, 2011, 8 pages.
Response to Restriction Requirement, U.S. Appl. No. 12/391,008, filed Aug. 29, 2011, 9 pages.
Response to Restriction Requirement, U.S. Appl. No. 12/386,105, filed Dec. 21, 2011, 9 pages.
Response to Restriction Requirement, U.S. Appl. No. 12/563,809, filed Feb. 24, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction Requirement, U.S. Appl. No. 12/760,388, filed Apr. 5, 2013, 7 pages.
Response to Restriction, U.S. Appl. No. 12/563,809, filed Aug. 6, 2012, 10 pages.
Response to Restriction, U.S. Appl. No. 11/924,425, filed Nov. 8, 2011, 5 pages.
Response to Restriction, U.S. Appl. No. 11/946,002, filed Sep. 23, 2011, 7 pages.
Response to Restriction, U.S. Appl. No. 12/505,056, filed Apr. 11, 2012, 9 pages.
Response to Restriction, U.S. Appl. No. 12/546,545, filed Jun. 4, 2012, 7 pages.
Response to Restriction, U.S. Appl. No. 13/573,662, filed Feb. 8, 2013, 8 pages.
Restriction Requirement, U.S. Appl. No. 13/573,662, mailed Jan. 17, 2013, 6 pages.
Restriction Requirement, U.S. Appl. No. 11/641,382, mailed Sep. 3, 2009, 6 pages.
Restriction Requirement, U.S. Appl. No. 11/641,569, mailed Apr. 27, 2009, 7 pages.
Restriction Requirement, U.S. Appl. No. 11/642,385, mailed Oct. 27, 2009, 7 pages.
Restriction Requirement, U.S. Appl. No. 11/656,323, mailed Nov. 13, 2009, 10 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 11/959,344, dated Oct. 29, 2010, 6 pages.
Restriction Requirement, U.S. Appl. No. 12/111,924, mailed Mar. 19, 2012, 8 pages.
Restriction Requirement, U.S. Appl. No. 12/386,105, dated Oct. 24, 2011, 7 pages.
Restriction Requirement, U.S. Appl. No. 12/390,667, dated Jul. 14, 2011, 9 pages.
Restriction Requirement, U.S. Appl. No. 12/391,008, dated Aug. 18, 2011, 6 pages.

(56) References Cited

OTHER PUBLICATIONS

Restriction Requirement, U.S. Appl. No. 12/505,056, mailed Mar. 14, 2012, 8 pages.
Restriction Requirement, U.S. Appl. No. 12/546,545, mailed May 3, 2012, 8 pages.
Restriction Requirement, U.S. Appl. No. 12/563,809, mailed Jul. 6, 2012, 6 pages.
Restriction Requirement, U.S. Appl. No. 12/636,939, mailed Apr. 13, 2012, 6 pages.
Restriction Requirement, U.S. Appl. No. 12/760,388, mailed Mar. 6, 2013, 7 pages.
Restriction Requirement, U.S. Appl. No. 29/296,687, mailed Sep. 21, 2010, 7 pages.
Rohlfing et al., "Chapter 11 Quo Vadis, Atlas-Based Segmentation?", in Handbook of Biomedical Image Analysis vol. III: Registration Models 435, 435-486 (Jasjit S. Suri et al. eds., Kluwer Academic/Plenum Publishers, NY 2005).
Rosset et al., "General Consumer Communication Tools for Improved Image Management and Communication in Medicine," Journal Digital Imaging, 2005;18(4):270-9.
Shakespeare D., "Conventional Instruments in Total Knee Replacement: What Should We Do With Them?" Knee. 2006;13(1):1-6.
Shepstone et al., "The shape of the Distal Femur: A Palaeopathological Comparison of Eburnated and Non-Eburnated Femora," Ann. Rheum Dis. 1999, 58:72-8.
Shirley et al., Realistic Ray Tracing, Second Edition, AK Peters, Natick, MA, 7 pages (Table of Contents), 2003.
Siston et al., "Averaging Different Alignment Axes Computer-Navigated Total Knee Arthroplasty," Improves Femoral Rotational Alignment in Journal Bone Joint Surg Am. 2008;90(10):2098-104.
Siston et al., "The Variability of Femoral Rotational Alignment in Total Knee Arthroplasty," Journal Bone Joint Surg Am. 2005;87(10):2276-80.
Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.
Spencer et al., "Initial Experience with Custom-Fit Total Knee Replacement: Intra-operative Events and Long-Leg Coronal alignment," International Orthopaedics (SICOT), 2009:In Press.
Strothotte et al., Non-Photorealistic Computer Graphics—Modeling, Rendering, and Animation, Morgan Kaufmann Publishers, San Francisco, CA, 9 pages (Table of Contents), 2002.
Stulberg et al., "Computer- and Robot-Assisted Orthopaedic Surgery", Computer-Integrated Surgery Technology and Clinical Applications, edited by Taylor et al., Massachusetts Institute of Technology, Chapter 27, pp. 373-378, 1996.
Teeny et al., "Primary Total Knee Arthroplasty in Patients with Severe Varus Deformity. A Comparative Study," Clin Orthop Relat Res. 1991(273):19-31.
Vande Berg et al., "Assessment of Knee Cartilage in Cadavers with Dual-Detector Spiral CT Arthrography and MR Imaging," Radiology, vol. 222, No. 2, pp. 430-436, Feb. 2002.
Wikipedia, the Free Encyclopedia, "CNC," (date unknown) located at http://en.wikipedia.org/wiki/CNC>, 6 pages, last visited on Apr. 12, 2007.
Wright Medical Technology, Inc., "Prophecy Pre-Operative Navigation Guides Surgical Technique," 2009.
U.S. Appl. No. 10/146,862, filed May 15, 2002, Park et al., (abandoned).
U.S. Appl. No. 29/394,882, filed Jun. 22, 2011, Park.
U.S. Appl. No. 13/730,585, filed Dec. 28, 2012, Park et al.
U.S. Appl. No. 13/730,608, filed Dec. 28, 2012, Park et al.
U.S. Appl. No. 13/731,697, filed Dec. 31, 2012, Pavlovskaia et al.
U.S. Appl. No. 13/749,095, filed Jan. 24, 2013, Song.
Non-Final Office Action, U.S. Appl. No. 11/641,569, mailed Jul. 12, 2013, 21 pages.
Non-Final Office Action, U.S. Appl. No. 12/505,056, mailed Jun. 28, 2013, 7 pages.
Non-Final Office Action, U.S. Appl. No. 12/760,388, mailed Jun. 20, 2013, 54 pages.
Non-Final Office Action, U.S. Appl. No. 13/723,904, mailed Aug. 9, 2013, 6 pages.
Non-Final Office Action, U.S. Appl. No. 13/730,585, mailed Jun. 11, 2013, 10 pages.
Non-Final Office Action, U.S. Appl. No. 13/730,608, dated Oct. 7, 2013, 10 pages.
Notice of Allowance, Design U.S. Appl. No. 29/394,882, mailed May 24, 2013, 16 pages.
Notice of Allowance, U.S. Appl. No. 13/086,275, mailed Aug. 27, 2013, 31 pages.
Response to Final Office Action, U.S. Appl. No. 12/546,545, filed Feb. 20, 2013, 13 pages.
Response to Non-Final Office Action, U.S. Appl. No. 12/390,667, filed Feb. 26, 2013, 36 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
Audette et al. "An algorithmic overview of surface registration techniques for medical imaging." Medical Image Analysis, vol. 4, No. 3, Sep. 1, 2000, pp. 201-217.
Banks et al. "Accurate Measurement of Three-Dimensional Knee Replacement Kinematics Using Single-Plane Fluoroscopy." IEEE Transactions on Biomedical Engineering, vol. 43, No. 6, Jun. 1996.
Calvo et al., "High Resolution MRI Detects Cartilage Swelling at the Early Stages of Experimental Osteoarthritis," OARSI, 2001, pp. 463-472.
Delp et al. "An Interactive Graphics-Based Model of the lower Extremity to Study Orthopaedic Surgical Procedures." IEEE Transactions on Biomedical Engineering, vol. 37, No. 8, Aug. 1990.
Garg, A. et al.. "Prediction of Total Knee Motion Using a Three-Dimensional Computer-Graphics Model." J. Biomechanics, vol. 23, No. 1, pp. 45-58, 1990.
Ibáñez et al., The ITK Software Guide, Second Edition, Updated for ITK version 2.4, Nov. 21, 2005, pp. 114, 396-411, and 426.
Richolt et al. "Planning and Evaluation of Reorienting Osteotomies of the Proximal Femur in Cases of SCFE Using Virtual Three-Dimensional Models." Lecture Notes in Computer Science, vol. 1496, 1998, pp. 1-8.
Siemens MAGNETOM Sonata 1.5T Technical Specifications, pp. 1-4, accessed online Jan. 28, 2014.
Taylor et al., "Computer-integrated revision total hip replacement surgery: concept and preliminary results," Medical Image Analysis (1999) vol. 3, No. 3, pp. 301-319.
Walker, P. S. et al. "Range of Motion in Total Knee Arthroplasty: A Computer Analysis." Clinical Orthopaedics and Related Research, No. 262, Jan. 1991.
Xie et al. "Segmentation by surface-to-image registration." proceedings of SPIE, vol. 6144, Mar. 2 2006, pp. 614405-1-614405-7.
Advisory Action, U.S. Appl. No. 11/642,385, dated Aug. 1, 2014.
Amendment and Response After Final Office Action, U.S. Appl. No. 11/656,323, dated Aug. 25, 2014.
Amendment Under 37 CFR 1.312, U.S. Appl. No. 14/824,731, dated Dec. 28, 2015.
Appeal Brief, U.S. Appl. No. 11/642,385, dated Oct. 7, 2014.
Australian Patent Examination Report No. 1, AU 2013200861, dated Mar. 3, 2015.
Canadian Office Action, Appl. No. 2642616, dated Apr. 22, 2015.
Canadian Office Action, Appl. No. 2708393, dated Jul. 29, 2014.
Canadian Office Action, CA2642616, dated Feb. 26, 2016.
Canadian Office Action, CA2708393, dated Mar. 11, 2016.

(56) References Cited

OTHER PUBLICATIONS

Canadian Office Action, CA2708393, dated May 7, 2015.
Canadian Office Action, CA2721735, dated Jul. 7, 2015.
Canadian Office Action, CA2721762, dated Nov. 10, 2015.
Decision on Appeal, U.S. Appl. No. 12/391,008, dated Dec. 11, 2015.
EP Communication pursuant to Article 94(3) EPC, EP10192631.9, dated Feb. 12, 2016.
EP Search Report and Opinion, EP09800841.0, dated Mar. 22, 2016.
European Examination Report, EP10192631.9, dated Feb. 11, 2015.
European Patent Office, Summons to Attend Oral Proceedings, EP07749030.8, dated Sep. 10, 2015.
European Search Report, EP 09835583.7, dated May 9, 2014.
European Search Report, EP09718014.5, dated May 13, 2015.
European Search Report, EP09718041.8, dated May 12, 2015.
European Search Report, EP09739422.5, dated Mar. 28, 2013, 9 pages.
European Search Report, EP09823986.6, dated Sep. 23, 2014.
European search Report, European Appl. No. 08863202.1, dated May 16, 2014.
Extended European Search Report, European Appl. No. 13188389.4, dated Jan. 8, 2014.
Final Office Action, U.S. Appl. No. 11/641,569, dated Nov. 29, 2013, 20 pages.
Final Office Action, U.S. Appl. No. 11/642,385, dated Apr. 25, 2014.
Final Office Action, U.S. Appl. No. 11/656,323, dated Apr. 3, 2014.
Final Office Action, U.S. Appl. No. 11/946,002, dated Sep. 17, 2014.
Final Office Action, U.S. Appl. No. 12/390,667, dated Oct. 25, 2013, 17 pages.
Final Office Action, U.S. Appl. No. 12/505,056, dated Dec. 30, 2013, 48 pages.
Final Office Action, U.S. Appl. No. 12/546,545, dated Oct. 7, 2013, 24 pages.
Final Office Action, U.S. Appl. No. 13/723,904, dated Dec. 24, 2013, 10 pages.
Final Office Action, U.S. Appl. No. 13/730,585, dated Dec. 27, 2013, 8 pages.
Final Office Action, U.S. Appl. No. 11/946,002, dated Nov. 30, 2015.
Final Rejection, U.S. Appl. No. 13/749,095, dated Dec. 24, 2015.
Final Rejection, U.S. Appl. No. 14/476,500, dated Feb. 1, 2016.
International Search Report and Written Opinion, PCT/US2014/030496, dated Aug. 6, 2014.
Japanese Office Action, JP Application No. 2011-507530, dated Dec. 17, 2013, 8 pages.
Japanese Office Action, JP2014-147908, dated Jun. 9, 2015.
Non-Final Office Action, U.S. Appl. No. 13/731,697, dated Jan. 29, 2015.
Non-Final Office Action, U.S. Appl. No. 13/749,095, dated Jan. 27, 2015.
Non-Final Office Action, U.S. Appl. No. 11/642,385, dated Oct. 22, 2013, 37 pages.
Non-Final Office Action, U.S. Appl. No. 11/656,323, dated Oct. 22, 2013, 36 pages.
Non-Final Office Action, U.S. Appl. No. 11/656,323, dated Sep. 18, 2014.
Non-Final Office Action, U.S. Appl. No. 11/946,002, dated Oct. 2, 2013, 39 pages.
Non-Final Office Action, U.S. Appl. No. 11/946,002, dated Feb. 6, 2014, 46 pages.
Non-Final Office Action, U.S. Appl. No. 13/488,505, dated Jul. 17, 2014.
Non-Final Office Action, U.S. Appl. No. 13/730,467, dated Jan. 15, 2014, 8 pages.
Non-Final Office Action, U.S. Appl. No. 11/946,002, dated May 18, 2016.
Non-Final Office Action, U.S. Appl. No. 11/946,002, dated Jun. 29, 2015.
Non-Final Office Action, U.S. Appl. No. 13/749,095, dated Sep. 10, 2015.
Non-Final Office Action, U.S. Appl. No. 13/960,498, dated Feb. 9, 2016.
Non-Final Office Action, U.S. Appl. No. 14/011,998, dated Feb. 12, 2016.
Non-Final Office Action, U.S. Appl. No. 14/084,255, dated Feb. 25, 2016.
Non-Final Office Action, U.S. Appl. No. 14/476,500, dated Jun. 18, 2015.
Non-Final Office Action, U.S. Appl. No. 14/869,762, dated Mar. 31, 2016.
Notice of Allowance, U.S. Appl. No. 11/656,323, dated Feb. 3, 2015.
Notice of Allowance, U.S. Appl. No. 11/641,382, mailed Feb. 6, 2013, 14 pages.
Notice of Allowance, U.S. Appl. No. 11/924,425, mailed Feb. 5, 2013, 16 pages.
Notice of Allowance, U.S. Appl. No. 29/394,882, mailed Feb. 4, 2013, 32 pages.
Notice of Allowance, U.S. Appl. No. 11/641,569, dated Feb. 5, 2014, 11 pages.
Notice of Allowance, U.S. Appl. No. 12/390,667, dated Jan. 17, 2014, 9 pages.
Notice of Allowance, U.S. Appl. No. 12/505,056, dated Mar. 6, 2014, 10 pages.
Notice of Allowance, U.S. Appl. No. 12/546,545, dated Dec. 26, 2013, 9 pages.
Notice of Allowance, U.S. Appl. No. 12/636,939, dated Oct. 7, 2013, 28 pages.
Notice of Allowance, U.S. Appl. No. 12/760,388, dated Jan. 22, 2014, 13 pages.
Notice of Allowance, U.S. Appl. No. 13/723,904, dated Mar. 7, 2014, 8 pages.
Notice of Allowance, U.S. Appl. No. 13/730,467, dated May 5, 2014.
Notice of Allowance, U.S. Appl. No. 13/730,585, dated Mar. 18, 2014, 10 pages.
Notice of Allowance, U.S. Appl. No. 13/730,608, dated Apr. 18, 2014.
Notice of Allowance, U.S. Appl. No. 13/731,850, dated Jun. 6, 2014.
Notice of Allowance, U.S. Appl. No. 12/391,008, dated Dec. 22, 2015.
Notice of Allowance, U.S. Appl. No. 13/731,697, dated Jul. 29, 2015.
Notice of Allowance, U.S. Appl. No. 13/749,095, dated Apr. 7, 2016.
Notice of Allowance, U.S. Appl. No. 14/476,500, dated May 19, 2016.
Notice of Allowance, U.S. Appl. No. 14/824,731, dated Oct. 20, 2015.
Preliminary Amendment, U.S. Appl. No. 13/731,850, filed Apr. 11, 2014, 8 pages.
Reply Brief, U.S. Appl. No. 11/642,385, dated Jan. 23, 2015.
Response to Final Office Action, U.S. Appl. No. 11/641,569, dated Jan. 29, 2014, 10 pages.
Response to Final Office Action, U.S. Appl. No. 11/642,385, dated Jul. 22, 2014.
Response to Final Office Action, U.S. Appl. No. 12/390,667, dated Dec. 23, 2013, 5 pages.
Response to Final Office Action, U.S. Appl. No. 12/546,545, dated Dec. 9, 2013, 8 pages.
Response to Final Office Action, U.S. Appl. No. 12/505,056, dated Feb. 26, 2014, 19 pages.
Response to Final Office Action, U.S. Appl. No. 13/723,904, dated Feb. 19, 2014, 7 pages.
Response to Final Office Action, U.S. Appl. No. 13/730,585, dated Feb. 26, 2014, 9 pages.
Response to Final Office Action, U.S. Appl. No. 11/946,002, dated Mar. 29, 2016.
Response to Final Office Action, U.S. Appl. No. 13/749,095, dated Feb. 17, 2016.

(56) References Cited

OTHER PUBLICATIONS

Response to Non-Final Office Action, U.S. Appl. No. 13/731,697, dated May 26, 2015.
Response to Non-Final Office Action, U.S. Appl. No. 13/749,095, dated Apr. 20, 2015.
Response to Non-Final Office Action, U.S. Appl. No. 13/723,904, filed Nov. 6, 2013, 8 pages.
Response to Non-Final Office Action, U.S. Appl. No. 11/946,002, filed Dec. 6, 2013, 18 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Response to Non-Final Office Action, U.S. Appl. No. 11/642,385, dated Feb. 24, 2014, 16 pages.
Response to Non-Final Office Action, U.S. Appl. No. 13/730,467, dated Apr. 11, 2014, 8 pages.
Response to Non-Final Office Action, U.S. Appl. No. 11/946,002, dated Jul. 7, 2014.
Response to Non-Final Office Action, U.S. Appl. No. 11/946,002, dated Sep. 29, 2015.
Response to Non-Final Office Action, U.S. Appl. No. 14/011,998, dated May 6, 2016.
Response to Non-Final Office Action, U.S. Appl. No. 14/476,500, dated Oct. 16, 2015.
Response to Restriction, U.S. Appl. No. 14/476,500, dated Mar. 17, 2015.
Response to Restriction, U.S. Appl. No. 13/749,095, dated Nov. 13, 2014.
Response to Restriction, U.S. Appl. No. 13/488,505, dated May 5, 2014, 7 pages.
Response to Restriction, U.S. Appl. No. 13/960,498, dated Nov. 19, 2015.
Restriction Requirement, U.S. Appl. No. 14/476,500, dated Feb. 25, 2015.
Restriction Requirement, U.S. Appl. No. 13/488,505, dated Mar. 4, 2014, 5 pages.
Restriction Requirement, U.S. Appl. No. 13/749,095, dated Sep. 25, 2014.
Restriction Requirement, U.S. Appl. No. 13/960,498, dated Sep. 23, 2015.
Supplementary European Search Report and Opinion, EP 09739474.6, dated Feb. 27, 2014, 7 pages.
Extended European Search Report, European Appl. No. 14765072.5, dated Sep. 22, 2016.
Non-Final Office Action, U.S. Appl. No. 14/086,849, dated Nov. 2, 2016.

* cited by examiner

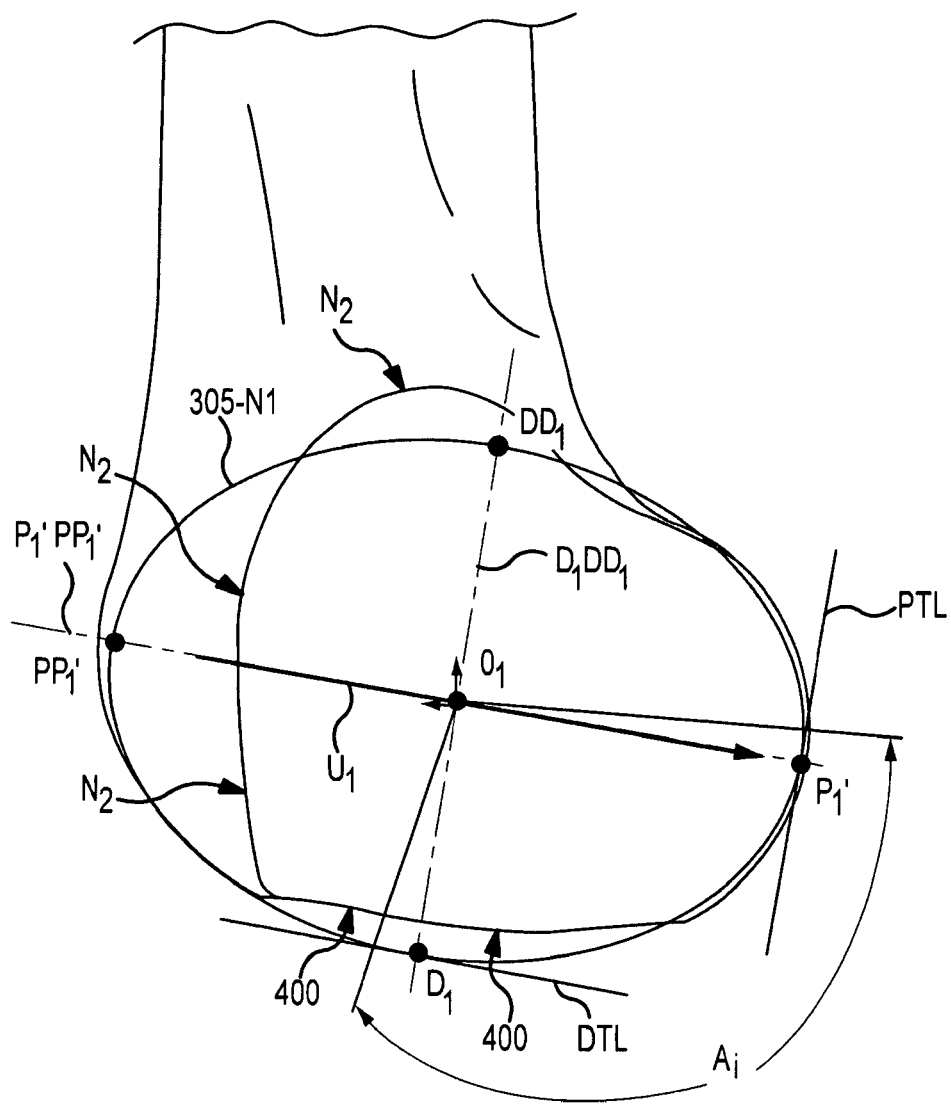
FIG.5C1

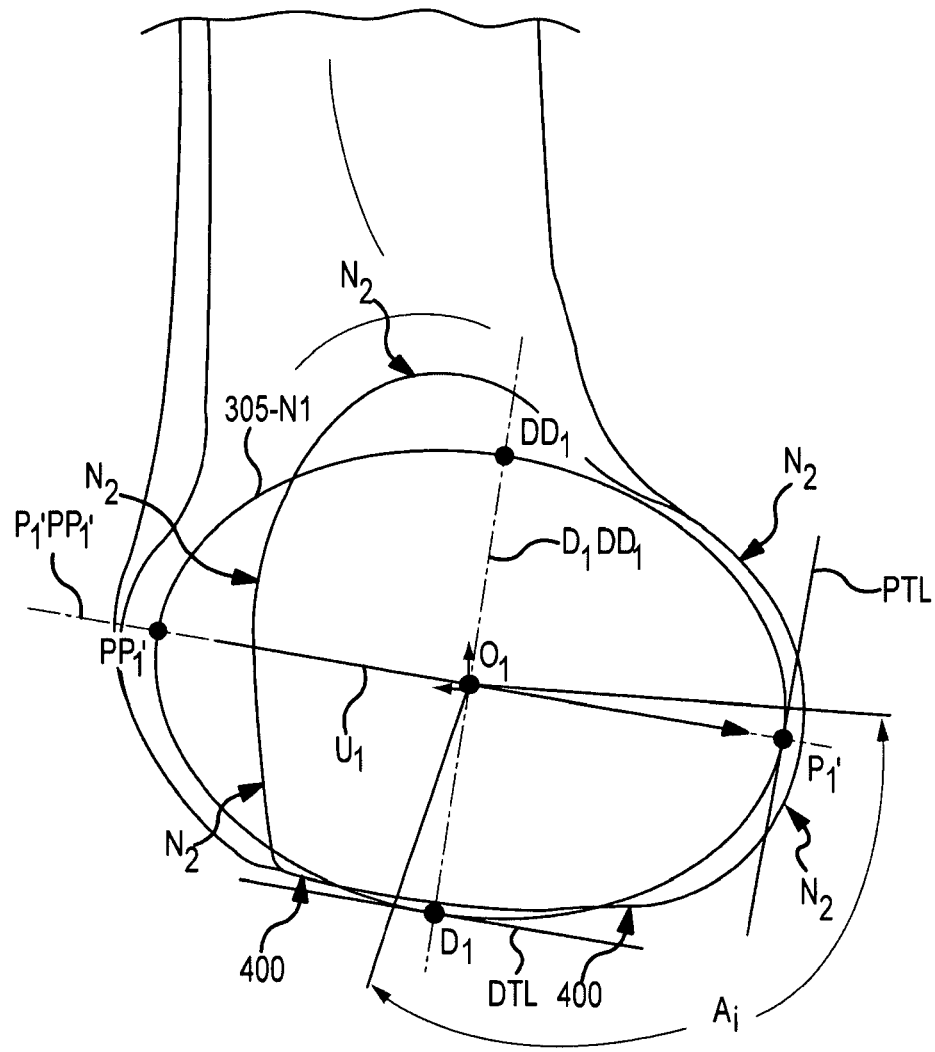
FIG.5C2

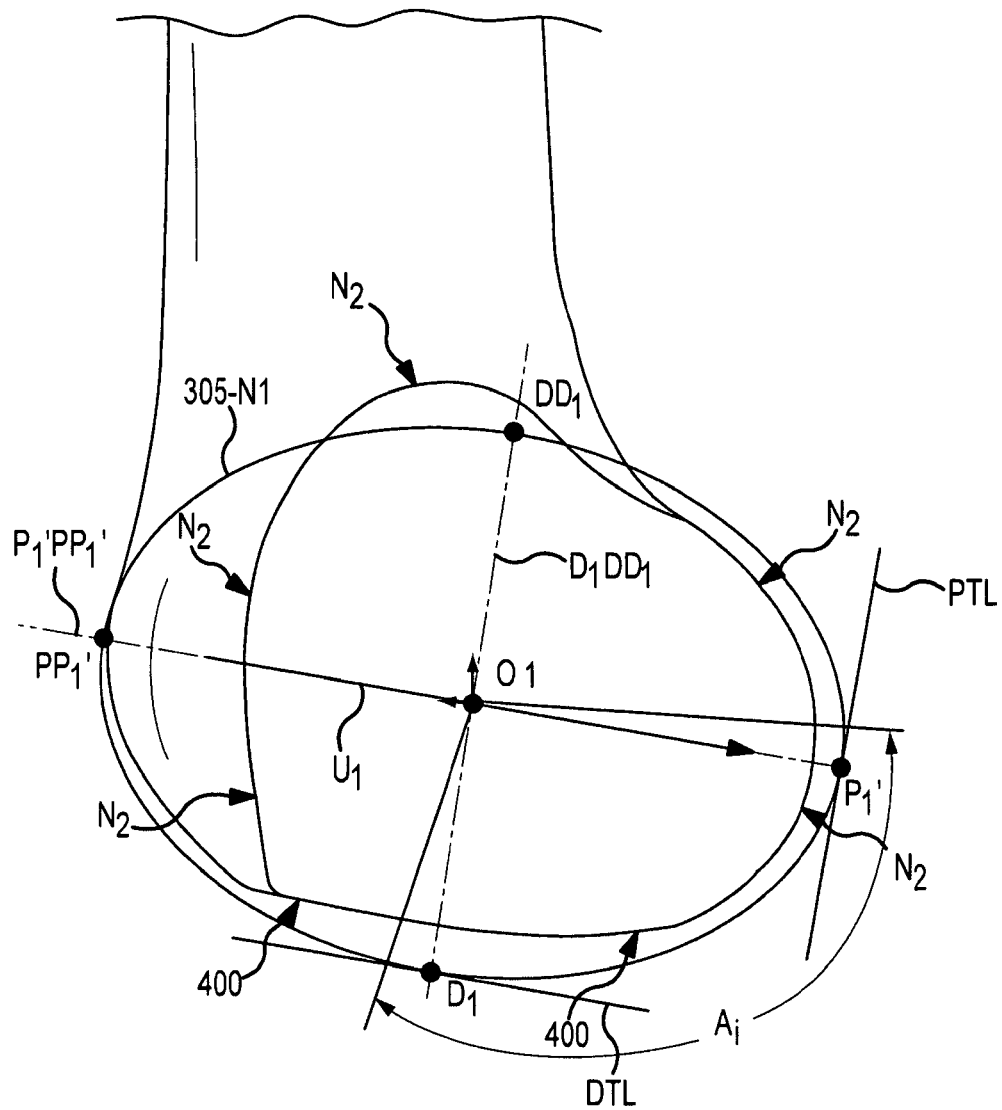
FIG.5C3

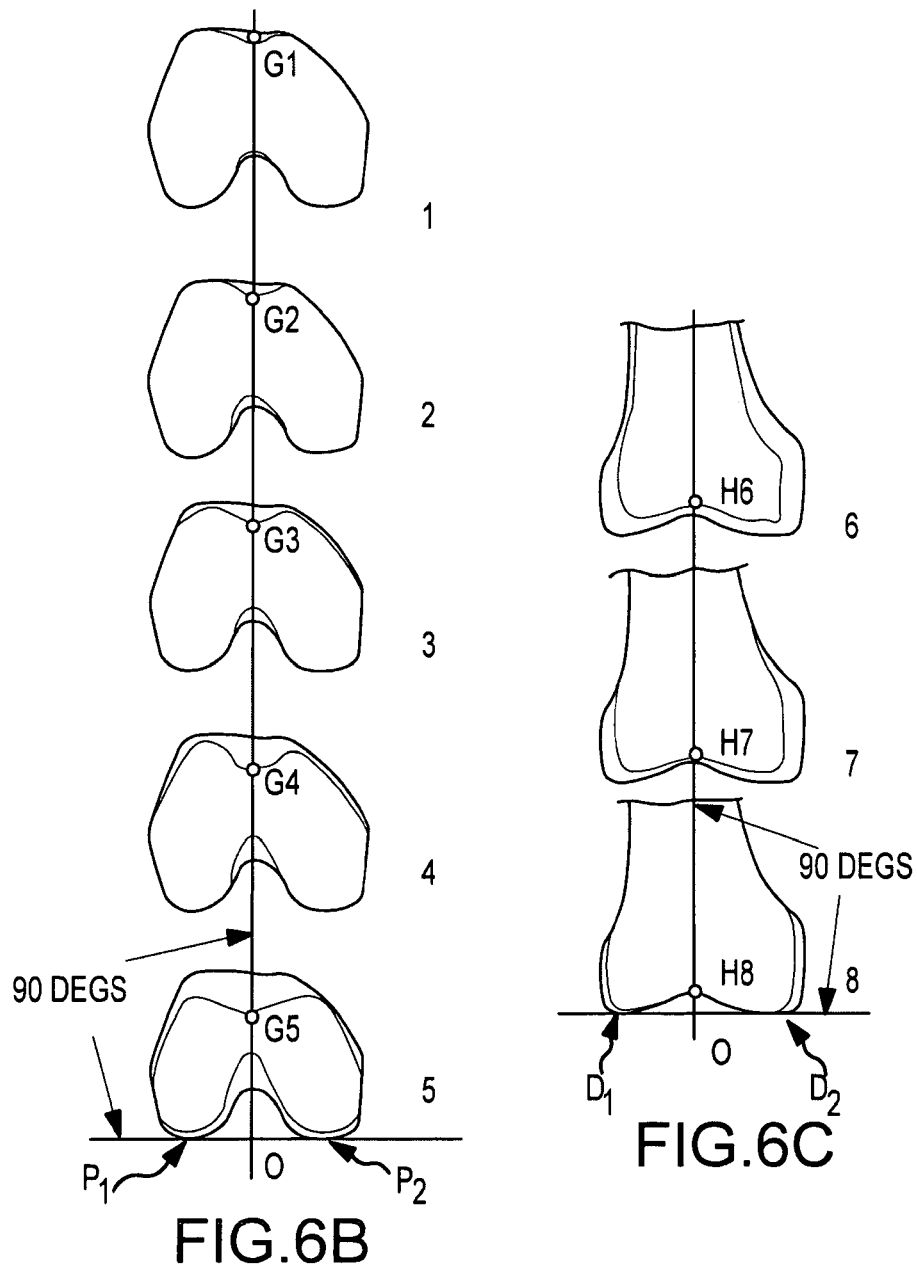

OSTEO ARTHRITIS KNEE BONE DAMAGE CRITERIA

| MEDIAL KNEE | | | LATERAL KNEE | | | RESTORATION (YES/NO) |
|---|---|---|---|---|---|---|
| SEVERE | MEDIUM | LIGHT | SEVERE | MEDIUM | LIGHT | |
|  |  | X |  |  | X | YES |
|  |  | X | X |  |  | YES |
|  |  | X |  | X |  | YES |
|  | X |  |  |  | X | YES |
|  | X |  | X |  |  | YES |
|  | X |  |  | X |  | NO |
| X |  |  |  |  | X | YES |
| X |  |  |  | X |  | NO |
| X |  |  | X |  |  | NO |

LIGHT: NO BONE DAMAGE OR BONE DAMAGE << 1mm
MEDIUM: BONE DAMAGE≈1mm
SEVERE: BONE DAMAGE >>1mm

FIG.7

GENERATION OF A COMPUTERIZED BONE MODEL REPRESENTATIVE OF A PRE-DEGENERATED STATE AND USEABLE IN THE DESIGN AND MANUFACTURE OF ARTHROPLASTY DEVICES

CROSS REFERENCE TO RELATED APPLICATIONS

The present application is a divisional application of U.S. application Ser. No. 12/111,924 filed Apr. 29, 2008, which application is hereby incorporated by reference in its entirety.

FIELD OF THE INVENTION

The present invention relates to systems and methods for manufacturing customized surgical devices. More specifically, the present invention relates to automated systems and methods for manufacturing customized arthroplasty jigs.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on a human to "eyeball" bone models on a computer screen to determine configurations needed for the generation of the customized jigs. This is "eyeballing" or manual manipulation of the bone models on the computer screen is inefficient and unnecessarily raises the time, manpower and costs associated with producing the customized arthroplasty jigs. Furthermore, a less manual approach may improve the accuracy of the resulting jigs.

There is a need in the art for a system and method for reducing the labor associated with generating customized arthroplasty jigs. There is also a need in the art for a system and method for increasing the accuracy of customized arthroplasty jigs.

SUMMARY

Preoperative assessment of bone loss is advantageous for prosthesis design, for example, to reduce the likelihood of prosthesis loosening and to provide a more reliable bone restoration method for preoperative implant design, thereby improving the success rate for such procedures such as total knee arthroplasty ("TKA") and partial knee arthroplasty (e.g., a unicompartment knee arthroplasty) and providing a patient-specific bone restoration method to fit an individual patient's knee features.

The current available joint reconstruction and replacement surgeries, including knee, ankle, hip, shoulder or elbow arthroplasty, are mainly based on standard guidelines and methods for acceptable performance. Taking this into account, the positioning and orientation of the arthroplasty work on a joint is based on standard values for orientation relative to the biomechanical axes, such as flexion/extension, varus/valgus, and range of motion.

One of the surgical goals of joint replacement/reconstruction should be to achieve a certain alignment relative to a load axes. However, the conventional standards are based on static load analysis and therefore may not be able to provide an optimal joint functionality for adopting individual knee features of OA patients. The methods disclosed herein provide a kinetic approach for bone restoration, properly balancing the unconstrained joint and ligaments surrounding the joint, and resulting in a placement of a prosthetic implant that generally restores the patient's knee to a generally pre-degenerated state.

In one embodiment, the result of the bone restoration process disclosed herein is a TKA or partial knee arthroplasty procedure that generally returns the knee to its pre-degenerated state whether that pre-degenerated state is naturally varus, valgus or neutral. In other words, if the patient's knee was naturally varus, valgus or neutral prior to degenerating, the surgical procedure will result in a knee that is generally restored to that specific natural pre-degenerated alignment, as opposed to simply making the knee have an alignment that corresponds to the mechanical axis, as is the common focus and result of most, if not all, arthroplasty procedures known in the art.

Disclosed herein is a method of generating a restored bone model representative of at least a portion of a patient bone in a pre-degenerated state. In one embodiment, the method includes: determining reference information from a reference portion of a degenerated bone model representative of the at least a portion of the patient bone in a degenerated state; and using the reference information to restore a degenerated portion of the degenerated bone model into a restored portion representative of the degenerated portion in the pre-degenerated state. In one embodiment, the method further includes employing the restored bone model in defining manufacturing instructions for the manufacture of a customized arthroplasty jig.

Also disclosed herein is a customized arthroplasty jig manufactured according to the above-described method. In one embodiment, the customized arthroplasty jig is configured to facilitate a prosthetic implant restoring a patient joint to a natural alignment. The prosthetic implant may be for a total joint replacement or partial joint replacement. The patient joint may be a variety of joints, including, but not limited to, a knee joint.

Disclosed herein is a method of generating a computerized bone model representative of at least a portion of a patient bone in a pre-degenerated state. In one embodiment, the method includes: generating at least one image of the patient bone in a degenerated state; identifying a reference portion associated with a generally non-degenerated portion of the patient bone; identifying a degenerated portion associated with a generally degenerated portion of the patient bone; and using information from at least one image associated with the reference portion to modify at least one aspect associated with at least one image associated the generally degenerated portion. In one embodiment, the method may further include employing the computerized bone model representative of the at least a portion of the patient bone in the pre-degenerated state in defining manufacturing instructions for the manufacture of a customized arthroplasty jig.

Also disclosed herein is a customized arthroplasty jig manufactured according to the above-described method. In one embodiment, the customized arthroplasty jig is configured to facilitate a prosthetic implant restoring a patient joint to a natural alignment. The prosthetic implant may be for a total joint replacement or partial joint replacement. The patient joint may be a variety of joints, including, but not limited to, a knee joint.

Disclosed herein is a method of generating a computerized bone model representative of at least a portion of a first patient bone in a pre-degenerated state. In one embodiment, the method includes: generating at least one image of the first patient bone in a degenerated state; identifying a reference portion associated with a generally non-degenerated portion of a second patient bone; identifying a degenerated portion associated with a generally degenerated portion of the first patient bone; and using information from at least one image associated with the reference portion to modify at least one aspect associated with at least one image associated the generally degenerated portion. In one embodiment, the method may further include employing the computerized bone model representative of the at least a portion of the first patient bone in the pre-degenerated state in defining manufacturing instructions for the manufacture of a customized arthroplasty jig.

Also disclosed herein is a customized arthroplasty jig manufactured according to the above-described method. In one embodiment, the customized arthroplasty jig is configured to facilitate a prosthetic implant restoring a patient joint to a natural alignment. The prosthetic implant may be for a total joint replacement or partial joint replacement. The patient joint may be a variety of joints, including, but not limited to, a knee joint.

Disclosed herein is a method of generating a computerized bone model representative of at least a portion of a first patient bone in a pre-degenerated state, wherein the first patient bone is part of a first patient joint. In one embodiment, the method includes: identifying a second patient bone of a second joint, wherein the second bone is a generally symmetrical mirror image of the first patient bone; generating a plurality of images of the second patient bone when the second patient bone is in a generally non-degenerated state; mirroring the plurality of images to reverse the order of the plurality images; and compiling the plurality of images in the reversed order to form the computerized bone model representative of the at least a portion of the first patient bone. In one embodiment, the method may further include employing the computerized bone model representative of the at least a portion of the first patient bone in the pre-degenerated state in defining manufacturing instructions for the manufacture of a customized arthroplasty jig.

Also disclosed herein is a customized arthroplasty jig manufactured according to the above-described method. In one embodiment, the customized arthroplasty jig is configured to facilitate a prosthetic implant restoring a patient joint to a natural alignment. The prosthetic implant may be for a total joint replacement or partial joint replacement. The patient joint may be a variety of joints, including, but not limited to, a knee joint.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 5C1 is an N2 image slice of the medial condyle as taken along the N2 line in FIG. 5A.

FIG. 5C2 is the same view as FIG. 5C1, except illustrating the need to increase the size of the reference information prior to restoring the contour line of the N2 image slice.

FIG. 5C3 is the same view as FIG. 5C1, except illustrating the need to reduce the size of the reference information prior to restoring the contour line of the N2 image slice.

FIG. 6B is the distal images slices 1-5 taken along section lines 1-5 of the femur restored bone model in FIG. 6A.

FIG. 6C is the coronal images slices 6-8 taken along section lines 6-8 of the femur restored bone model in FIG. 6A.

FIG. 7 is a table illustrating how OA knee conditions may impact the likelihood of successful bone restoration.

DETAILED DESCRIPTION

Figure 1A:
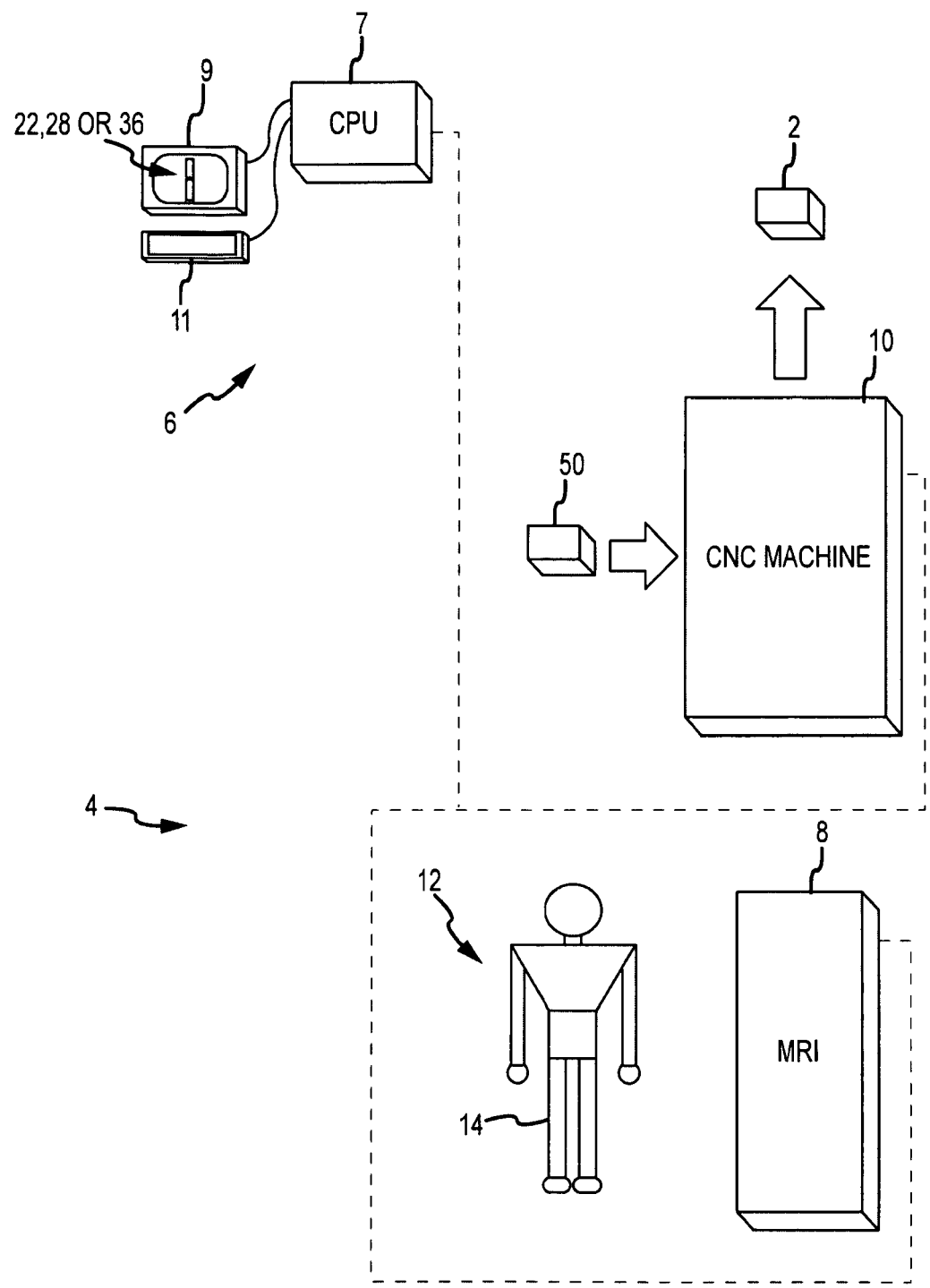
FIG. 1A is a schematic diagram of a system for employing the automated jig production method disclosed herein.

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. patent applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent Ser. No. 11/642,385 to Park et al., titled "Arthroplasty Devices and Related Methods" and filed Dec. 19, 2006. The disclosures of these three U.S. patent applications are incorporated by reference in their entireties into this Detailed Description.

a. Overview of System and Method for Manufacturing Customized Arthroplasty Cutting Jigs For an overview discussion of the systems 4 for, and methods of, producing the customized arthroplasty jigs 2, reference is made to FIGS. 1A-1E. FIG. 1A is a schematic diagram of a system 4 for employing the automated jig production method disclosed herein. FIGS. 1B-1E are flow chart diagrams outlining the jig production method disclosed herein. The following overview discussion can be broken down into three sections.

The first section, which is discussed with respect to FIG. 1A and [blocks 100-125] of FIGS. 1B-1E, pertains to an example method of determining, in a three-dimensional ("3D") computer model environment, saw cut and drill hole locations 30, 32 relative to 3D computer models that are termed restored bone models 28. The resulting "saw cut and drill hole data" 44 is referenced to the restored bone models 28 to provide saw cuts and drill holes that will allow arthroplasty implants to generally restore the patient's joint to its pre-degenerated state. In other words, the patient's joint will be restored to its natural alignment prior to degeneration. Thus, where the patient's pre-degenerated joint had a certain degree of valgus, the saw cuts and drill holes will allow the arthroplasty implants to generally restore the patient's joint to that degree of valgus. Similarly, where the patient's pre-degenerated joint had a certain degree of varus, the saw cuts and drill holes will allow the arthroplasty implants to generally restore the patient's joint to that degree of varus, and where the patient's pre-degenerated joint was neutral, the saw cuts and drill holes will allow the arthroplasty implants to generally restore the patient's joint to neutral.

The second section, which is discussed with respect to FIG. 1A and [blocks 100-105 and 130-145] of FIGS. 1B-1E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

Figure 1B:
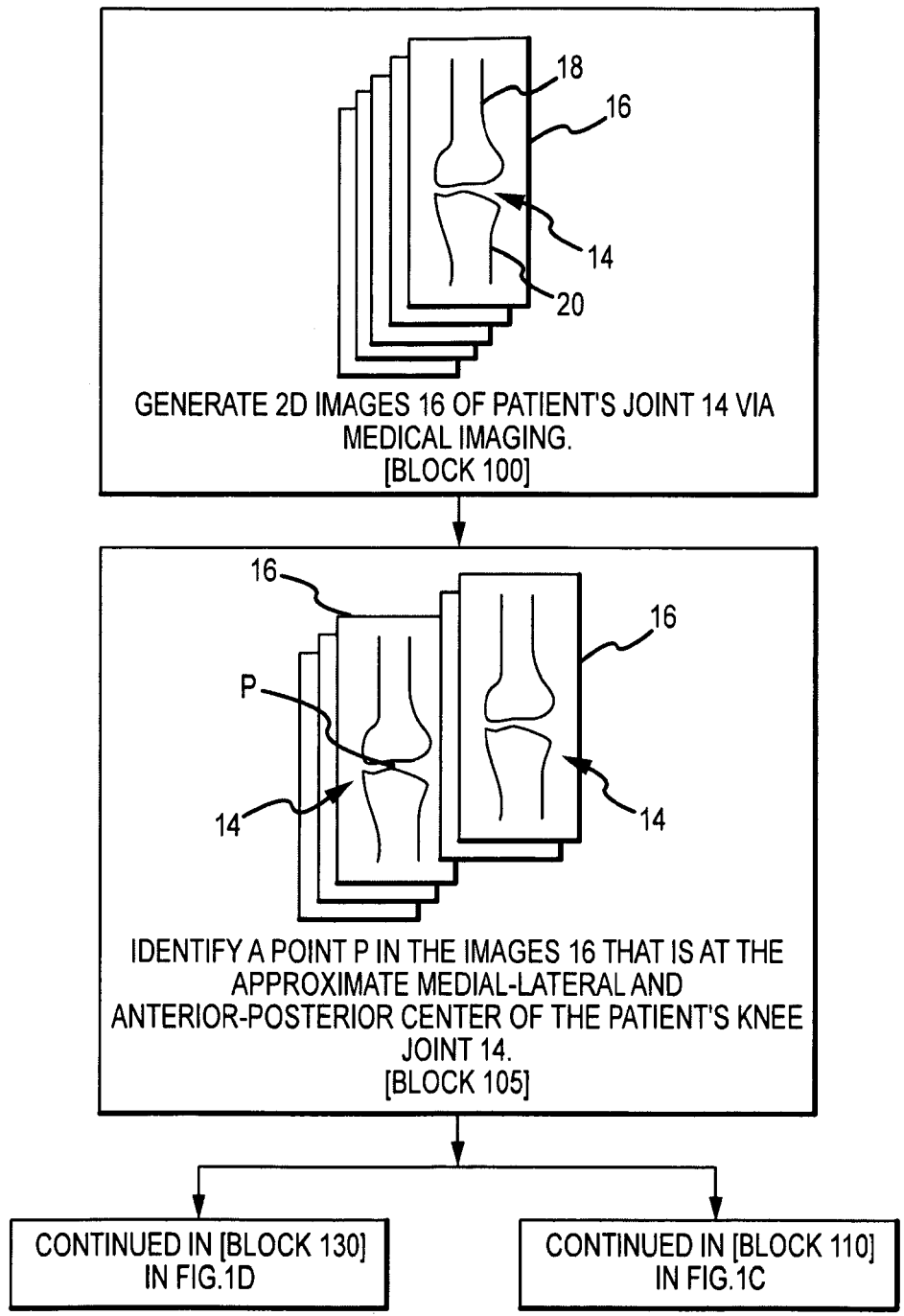
FIGS. 1B-1E are flow chart diagrams outlining the jig production method disclosed herein.
Figure 1C:
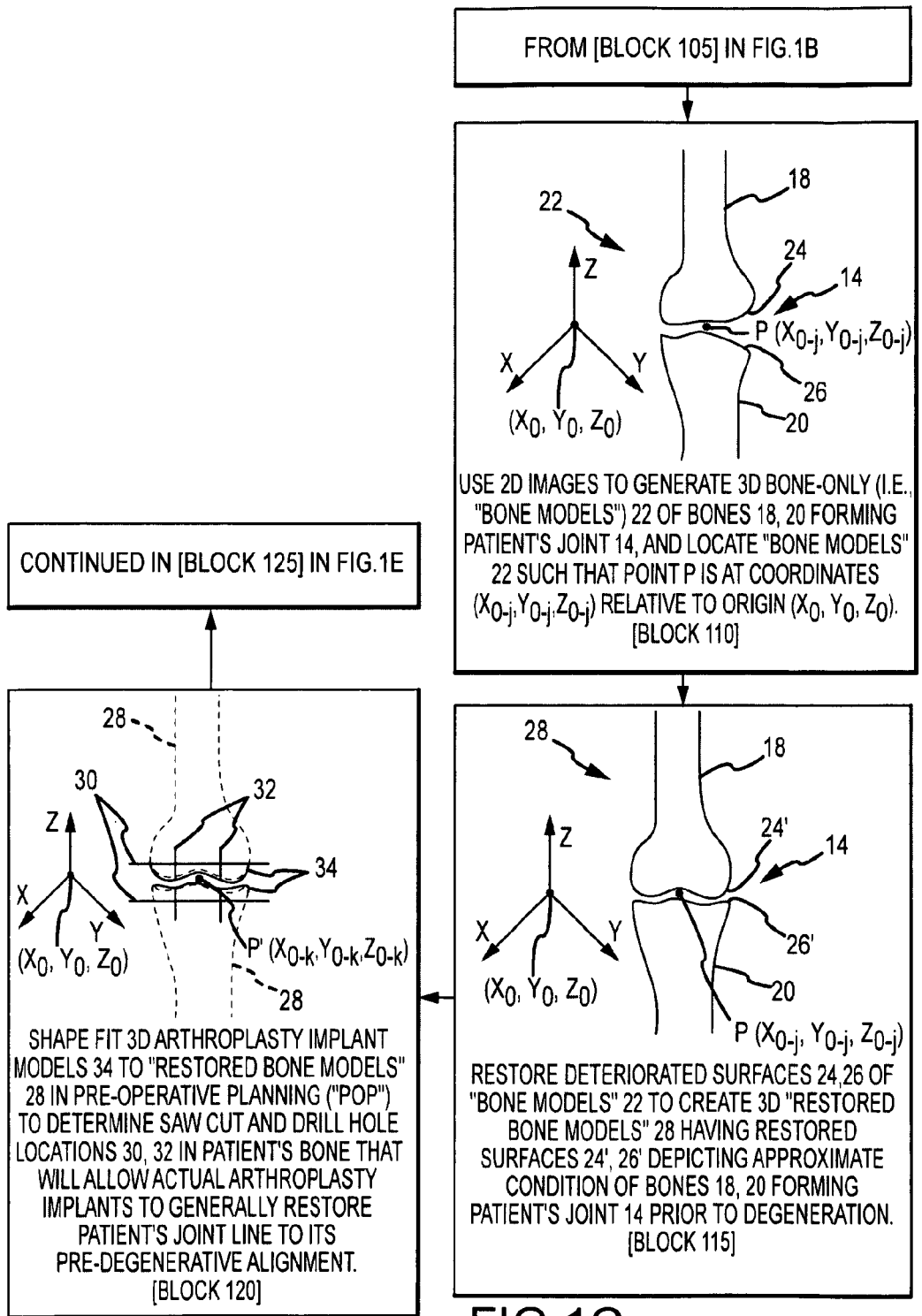
Figure 1D:
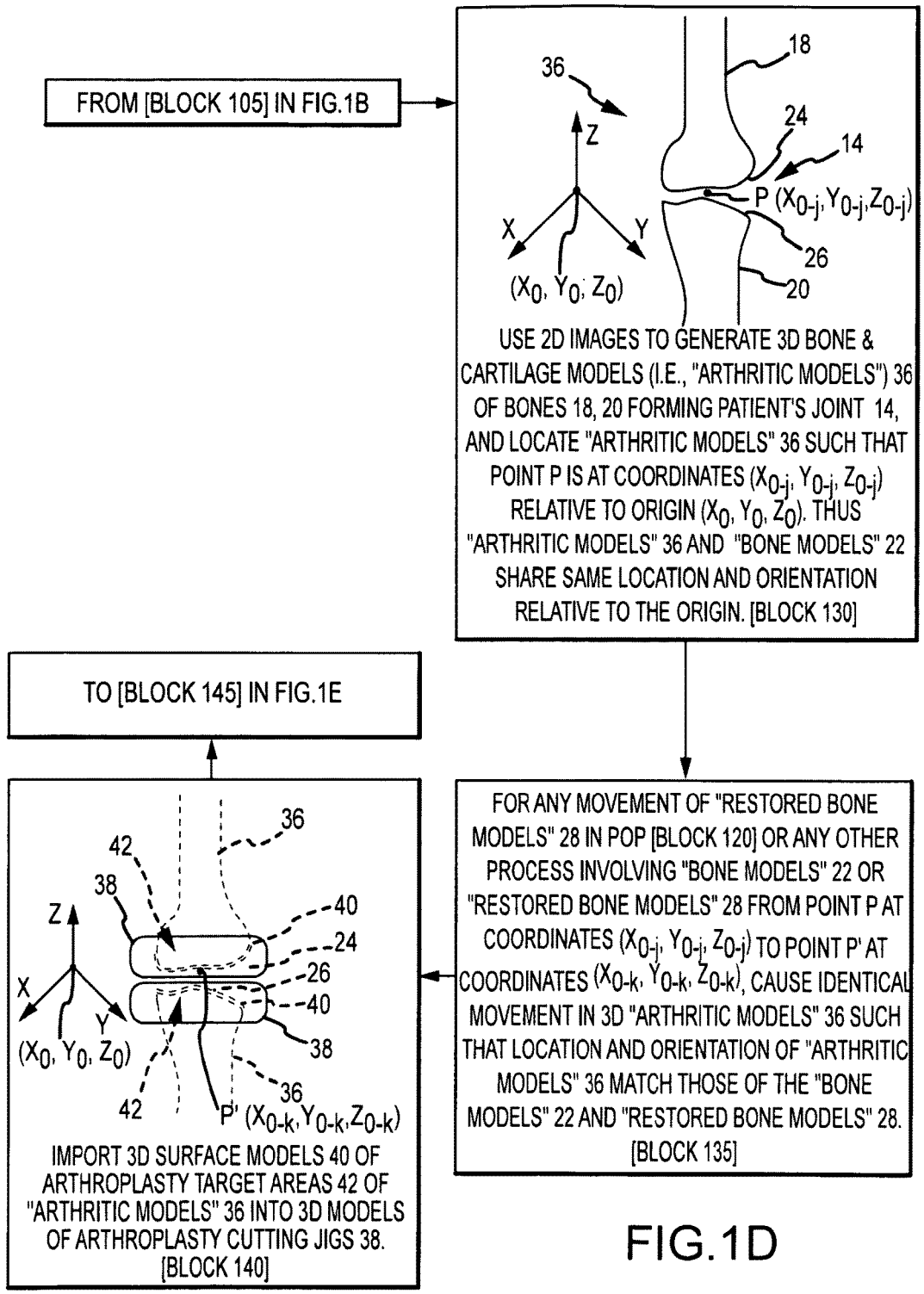
Figure 1E:
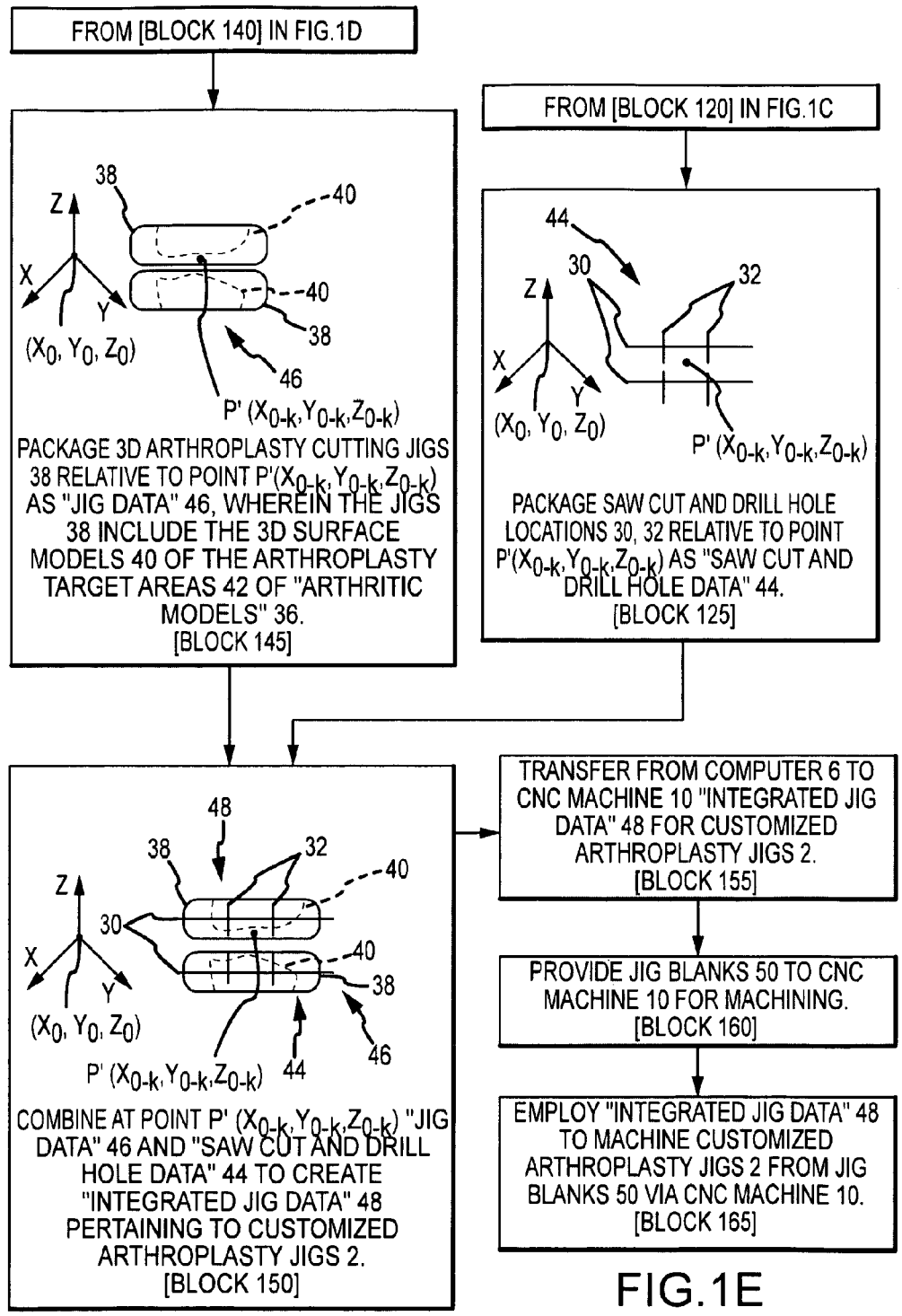

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated state. In other words, the customized arthroplasty jigs 2 facilitate preparing the patient's bone in a manner that allows the arthroplasty joint implants to restore the patient's joint to a natural alignment that corresponds to the patient's specific pre-degenerated alignment, whether that specific pre-degenerated alignment was valgus, varus or neutral.

As shown in FIG. 1A, the system 4 includes a computer 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

As indicated in FIG. 1A, a patient 12 has a joint 14 (e.g., a knee, elbow, ankle, wrist, hip, shoulder, skull/vertebrae or vertebrae/vertebrae interface, etc.) to be totally replaced (e.g., TKA), partially replaced (e.g., partial or compartmentalized replacement), resurfaced, or otherwise treated. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D") images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description.

As can be understood from FIG. 1A, the 2D images are sent to the computer 6 for creating computer generated 3D models. As indicated in FIG. 1B, in one embodiment, point P is identified in the 2D images 16 [block 105]. In one embodiment, as indicated in [block 105] of FIG. 1A, point P may be at the approximate medial-lateral and anterior-posterior center of the patient's joint 14. In other embodiments, point P may be at any other location in the 2D images 16, including anywhere on, near or away from the bones 18, 20 or the joint 14 formed by the bones 18, 20.

As described later in this overview, point P may be used to locate the computer generated 3D models 22, 28, 36 created from the 2D images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D images 16.

As shown in FIG. 1C, the 2D images 16 are employed to create computer generated 3D bone-only (i.e., "bone models") 22 of the bones 18, 20 forming the patient's joint 14 [block 110]. The bone models 22 are located such that point P is at coordinates $(X_{0-j}, Y_{0-j}, Z_{0-j})$ relative to an origin $(X_0, Y_0, Z_0)$ of an X-Y-Z axis [block 110]. The bone models 22 depict the bones 18, 20 in the present deteriorated condition with their respective degenerated joint surfaces 24, 26, which may be a result of osteoarthritis, injury, a combination thereof, etc.

Computer programs for creating the 3D computer generated bone models 22 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

As indicated in FIG. 1C, the 3D computer generated bone models 22 are utilized to create 3D computer generated "restored bone models" or "planning bone models" 28 wherein the degenerated surfaces 24, 26 are modified or restored to approximately their respective conditions prior to degeneration [block 115]. Thus, the bones 18, 20 of the restored bone models 28 are reflected in approximately their condition prior to degeneration. The restored bone models 28 are located such that point P is at coordinates $(X_{0-j}, Y_{0-j}, Z_{0-j})$ relative to the origin $(X_0, Y_0, Z_0)$. Thus, the restored bone models 28 share the same orientation and positioning relative to the origin $(X_0, Y_0, Z_0)$ as the bone models 22.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 on the 3D computer bone models 22 need to be modified to generally restore them to their pre-degenerated condition or an estimation or approximation of their pre-degenerated state. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state. In other words, the result is restored bone models 28 that can be used to represent the natural, pre-degenerated alignment and configuration of the patient's knee joint whether that pre-degenerated alignment and configuration was varus, valgus or neutral.

In one embodiment, the above-described bone restoration process is generally or completely automated to occur via a processor employing the methods disclosed herein. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition or an estimation or approximation of their pre-degenerated state. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state. A discussion of various embodiments of the automated restoration process employed to a greater or lesser extent by a computer is provided later in this Detailed Description.

As depicted in FIG. 1C, the restored bone models 28 are employed in a pre-operative planning ("POP") procedure to determine saw cut locations 30 and drill hole locations 32 in the patient's bones that will allow the arthroplasty joint implants, whether in the context of total joint arthroplasty or partial or compartmentalized joint arthroplasty, to generally restore the patient's joint line to its pre-degenerative or natural alignment [block 120].

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. By superimposing the implant models 34 over the restored bone models 28, or vice versa, the joint surfaces of the implant models 34 can be aligned or caused to correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. For example, a computer program may manipulate computer generated 3D implant models 34 (e.g., femur and tibia implants in the context of the joint being a knee) and restored bone models or planning bone models 8 relative to each other to determine the saw cut and drill hole locations 30, 32 relative to the restored bone models 28. The implant models 34 may be superimposed over the restored bone models 28, or vice versa. In one embodiment, the implant models 34 are located at point P' $(X_{0-k}, Y_{0-k}, Z_{0-k})$ relative to the origin $(X_0, Y_0, Z_0)$, and the restored bone models 28 are located at point P $(X_{0-j}, Y_{0-j}, Z_{0-j})$. To cause the joint surfaces of the models 28, 34 to correspond, the computer program may move the restored bone models 28 from point P $(X_{0-j}, Y_{0-j}, Z_{0-j})$ to point P' $(X_{0-k}, Y_{0-k}, Z_{0-k})$, or vice versa. Once the joint surfaces of the models 28, 34 are in close proximity, the joint surfaces of the implant models 34 may be shape-matched to align or correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

As indicated in FIG. 1E, in one embodiment, the data 44 regarding the saw cut and drill hole locations 30, 32 relative to point P' $(X_{0-k}, Y_{0-k}, Z_{0-k})$ is packaged or consolidated as the "saw cut and drill hole data" 44 [block 145]. The "saw cut and drill hole data" 44 is then used as discussed below with respect to [block 150] in FIG. 1E.

As can be understood from FIG. 1D, the 2D images 16 employed to generate the bone models 22 discussed above with respect to [block 110] of FIG. 1C are also used to create computer generated 3D bone and cartilage models (i.e., "arthritic models") 36 of the bones 18, 20 forming the patient's joint 14 [block 130]. Like the above-discussed bone models 22, the arthritic models 36 are located such that point P is at coordinates $(X_{0-j}, Y_{0-j}, Z_{0-j})$ relative to the origin $(X_0, Y_0, Z_0)$ of the X-Y-Z axis [block 130]. Thus, the bone and arthritic models 22, 36 share the same location and orientation relative to the origin $(X_0, Y_0, Z_0)$. This position/orientation relationship is generally maintained throughout the process discussed with respect to FIGS. 1B-1E. Accordingly, movements relative to the origin $(X_0, Y_0, Z_0)$ of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

Similar to the bone models 22, the arthritic models 36 depict the bones 18, in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the bone and arthritic models 36, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point P' ($X_{0-k}$, $Y_{0-k}$, $Z_{0-k}$) can also be imported into the jig models 38, resulting in jig models 38 positioned and oriented relative to point P' ($X_{0-k}$, $Y_{0-k}$, $Z_{0-k}$) to allow their integration with the bone cut and drill hole data 44 of [block 125].

In one embodiment, the procedure for indexing the jig models 38 to the arthroplasty target areas 42 is generally or completely automated, as disclosed in U.S. patent application Ser. No. 11/959,344 to Park, which is entitled System and Method for Manufacturing Arthroplasty Jigs, was filed Dec. 18, 2007 and is incorporated by reference in its entirety into this Detailed Description. For example, a computer program may create 3D computer generated surface models 40 of the arthroplasty target areas 42 of the arthritic models 36. The computer program may then import the surface models 40 and point P' ($X_{0-k}$, $Y_{0-k}$, $Z_{0-k}$) into the jig models 38, resulting in the jig models 38 being indexed to matingly receive the arthroplasty target areas 42 of the arthritic models 36. The resulting jig models 38 are also positioned and oriented relative to point P' ($X_{0-k}$, $Y_{0-k}$, $Z_{0-k}$) to allow their integration with the bone cut and drill hole data 44 of [block125].

In one embodiment, the arthritic models 36 may be 3D volumetric models as generated from the closed-loop process discussed in U.S. patent application Ser. No. 11/959,344 filed by Park. In other embodiments, the arthritic models 36 may be 3D surface models as generated from the open-loop process discussed in U.S. patent application Ser. No. 11/959,344 filed by Park.

As indicated in FIG. 1E, in one embodiment, the data regarding the jig models 38 and surface models 40 relative to point P' ($X_{0-k}$, $Y_{0-k}$, $Z_{0-k}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated state or, in other words, the joint's natural alignment.

As can be understood from FIGS. 1A and 1E, the "integrated jig data" 44 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50.

Figure 1F:
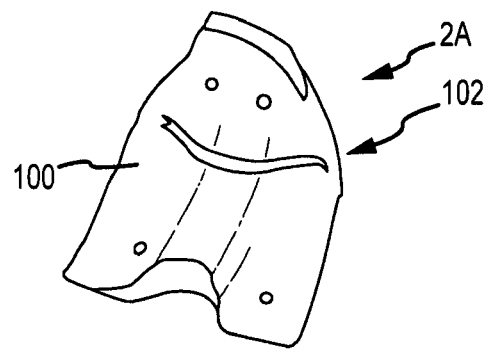
FIGS. 1F and 1G are, respectively, bottom and top perspective views of an example customized arthroplasty femur jig.
Figure 1G:
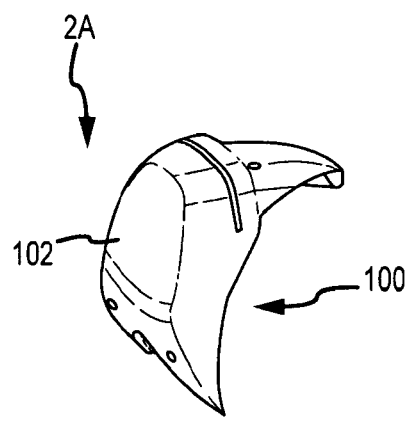
Figure 1H:
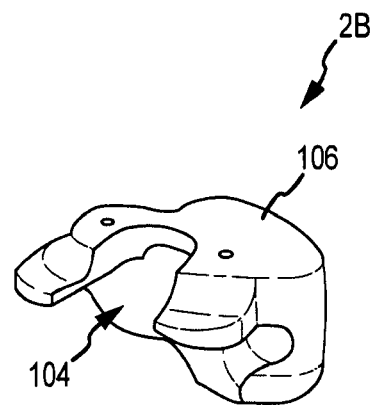
FIGS. 1H and 1I are, respectively, bottom and top perspective views of an example customized arthroplasty tibia jig.
Figure 1I:
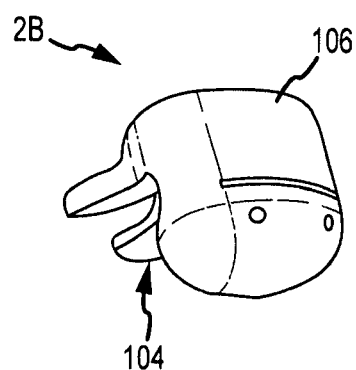

For a discussion of example customized arthroplasty cutting jigs 2 capable of being manufactured via the above-discussed process, reference is made to FIGS. 1F-1I. While, as pointed out above, the above-discussed process may be employed to manufacture jigs 2 configured for arthroplasty procedures (e.g., total joint replacement, partial joint replacement, joint resurfacing, etc.) involving knees, elbows, ankles, wrists, hips, shoulders, vertebra interfaces, etc., the jig examples depicted in FIGS. 1F-1I are for total knee replacement ("TKR") or partial knee replacement. Thus, FIGS. 1F and 1G are, respectively, bottom and top perspective views of an example customized arthroplasty femur jig 2A, and FIGS. 1H and 1I are, respectively, bottom and top perspective views of an example customized arthroplasty tibia jig 2B.

As indicated in FIGS. 1F and 1G, a femur arthroplasty jig 2A may include an interior side or portion 100 and an exterior side or portion 102. When the femur cutting jig 2A is used in a TKR or partial knee replacement procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR or partial knee replacement surgery, the surfaces of the target area 42 and the interior portion 100 match.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18.

As indicated in FIGS. 1H and 1I, a tibia arthroplasty jig 2B may include an interior side or portion 104 and an exterior side or portion 106. When the tibia cutting jig 2B is used in a TKR or partial knee replacement procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR or partial knee replacement surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20.

b. Overview of Automated Processes for Restoring Damaged Regions of 3D Bone Models to Generate 3D Restored Bone Models As mentioned above with respect to [block 115] of FIG. 1C, the process for restoring damaged regions of 3D "bone models" 22 to generate 3D "restored bone models" 28 can be automated to be carried out to a greater or lesser extent by a computer. A discussion of various examples of such an automated process will now concern the remainder of this Detailed Description, beginning with an overview of various automated bone restoration processes.

As can be understood from FIG. 1A and [blocks 100-105] of FIG. 1B, a patient 12 has a joint 14 (e.g., a knee, elbow, ankle, wrist, shoulder, hip, vertebra interface, etc.) to be replaced (e.g., partially or totally) or resurfaced. The patient 12 has the joint 14 scanned in an imaging machine 10 (e.g., a CT, MRI, etc. machine) to create a plurality of 2D scan images 16 of the bones (e.g., femur 18 and tibia 20) forming the patient's joint 14 (e.g., knee). The process of creating the 2D scan images or slices 16 may occur as disclosed in Ser. No. 11/946,002, which was filed by Park Nov. 27, 2007 and is incorporated by reference in its entirety into this Detailed Description. Each scan image 16 is a thin slice image of the targeted bone(s) 18, 20. The scan images 16 are sent to the CPU 7, which may employ an open-loop or closed-loop image analysis along targeted features 42 of the scan images 16 of the bones 18, 20 to generate a contour line for each scan image 16 along the profile of the targeted features 42. The process of generating contour lines for each scan image 16 may occur as disclosed in Ser. No. 11/959,344, which is incorporated by reference in its entirety into this Detailed Description.

As can be understood from FIG. 1A and [block 110] of FIG. 1C, the CPU 7 compiles the scan images 16 and, more specifically, the contour lines to generate 3D computer surface or volumetric models ("bone models") 22 of the targeted features 42 of the patient's joint bones 18, 20. In the context of total knee replacement ("TKR") or partial knee replacement surgery, the targeted features 42 may be the lower or knee joint portions of the patient's femur 18 and the upper or knee joint portions of the patient's tibia 20. More specifically, for the purposes of generating the femur bone models 22, the targeted features 42 may include the condyle portion of the femur and may extend upward to include at least a portion of the femur shaft. Similarly, for purposes of generating the tibia bone models 22, the targeted features 42 may include the plateau portion of the tibia and may extend downward to include at least a portion of the tibia shaft.

In some embodiments, the "bone models" 22 may be surface models or volumetric solid models respectively formed via an open-loop or closed-loop process such that the contour lines are respectively open or closed loops. Regardless, the bone models 22 are bone-only 3D computer generated models of the joint bones that are the subject of the arthroplasty procedure. The bone models 22 represent the bones in the deteriorated condition in which they existed at the time of the medical imaging of the bones.

To allow for the POP procedure, wherein the saw cut and drill hole locations 30, 32 are determined as discussed with respect to [block 120] of FIG. 1C, the "bone models" 22 and/or the image slices 16 (see [block 100] of FIG. 1B) are modified to generate a 3D computer generated model that approximates the condition of the patient's bones prior to their degeneration. In other words, the resulting 3D computer generated model, which is termed a "restored bone model" 28, approximates the patient's bones in a non-degenerated or healthy state and can be used to represent the patient's joint in its natural alignment prior to degeneration.

Figure 2:
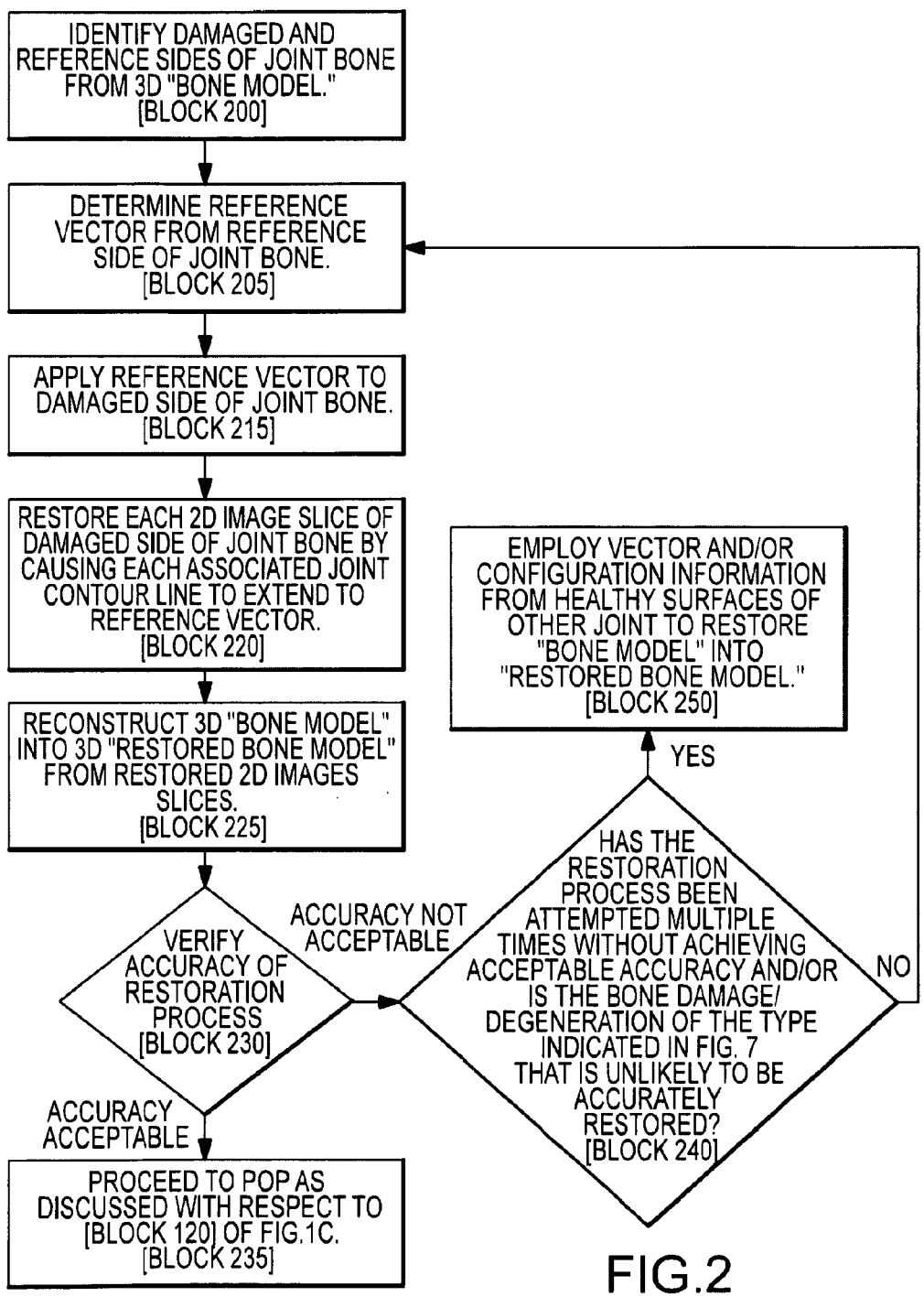
FIG. 2 is a diagram generally illustrating a bone restoration process for restoring a 3D computer generated bone model into a 3D computer generated restored bone model.

In one embodiment, the bone restoration process employed to generate the restored bone model 28 from the bone model 22 or image slices 16 may be as indicated in the process diagram depicted in FIG. 2. As shown in FIG. 2, the damaged and reference sides of a joint bone to undergo an arthroplasty procedure are identified from the 3D computer generated "bone model" [block 200]. The damaged side is the side or portion of the joint bone that needs to be restored in the bone model 22, and the reference side is the side of the joint bone that is generally undamaged or at least sufficiently free of deterioration that it can serve as a reference for restoring the damaged side.

As can be understood from FIG. 2, reference data or information (e.g., in the form of ellipses, ellipse axes, and/or vectors in the form of lines and/or planes) is then determined from the reference side of the joint bone [block 205]. The reference information or data is then applied to the damaged side of the joint bone [block 215]. For example, in a first embodiment and in the context of a knee joint, a vector associated with a femur condyle ellipse of the reference side is determined and applied to the damaged side femur condyle and damaged side tibia plateau. In a second embodiment and in the context of a knee joint, a vector associated with the highest anterior and posterior points of a tibia plateau of the reference side is determined and applied to the damaged side femur condyle and damaged side tibia plateau. These vectors are generally parallel with the condyle ellipse and generally parallel with the knee joint line.

As indicated in FIG. 2, each joint contour line associated with a 2D image slice of the damaged side of the joint bone is caused to extend to the reference vector or ellipse [block 220]. This restoration process is carried out slice-by-slice for the joint contour lines of most, if not all, image slices associated with the damaged side of the joint. The 3D "bone model" is then reconstructed into the 3D "restored bone model" from the restored 2D images slices [block 225].

Once generated from the "bone model" 22, the "restored bone model" 28 can then be employed in the POP process discussed with respect to [block 120] of FIG. 1C. As discussed with respect to [blocks 125 and 150], "saw cut and drill hole data" resulting from the POP process is indexed into "jig data" 46 to create "integrated jig data" 48. As discussed with respect to [blocks 155-165] of FIG. 1E, the "integrated jig data" 48 is utilized by a CNC machine 10 to produce customized arthroplasty jigs 2.

The systems 4 and methods disclosed herein allow for the efficient manufacture of arthroplasty jigs 2 customized for the specific bone features of a patient. Each resulting arthroplasty jig 2 includes an interior portion dimensioned specific to the surface features of the patient's bone that are the focus of the arthroplasty. Each jig 2 also includes saw cut slots and drill holes that are indexed relative to the interior portion of the jig such that saw cuts and drill holes administered to the patient's bone via the jig will result in cuts and holes that will allow joint implants to restore the patient's joint line to a pre-degenerated state or at least a close approximation of the pre-degenerated state.

Where the arthroplasty is for TKR or partial knee replacement surgery, the jigs will be a femur jig and/or a tibia jig. The femur jig will have an interior portion custom configured to match the damaged surface of the lower or joint end of the patient's femur. The tibia jig will have an interior portion custom configured to match the damaged surface of the upper or joint end of the patient's tibia.

The jigs 2 and systems 4 and methods of producing such jigs are illustrated herein in the context of knees and TKR or partial knee replacement surgery. However, those skilled in the art will readily understand the jigs 2 and system 4 and methods of producing such jigs can be readily adapted for use in the context of other joints and joint replacement or resurfacing surgeries, e.g., surgeries for elbows, shoulders, hips, etc. Accordingly, the disclosure contained herein regarding the jigs 2 and systems 4 and methods of producing such jigs should not be considered as being limited to knees and TKR or partial knee replacement surgery, but should be considered as encompassing all types of joint surgeries.

c. Overview of the Mechanics of an Accurate Restored Bone Model

An overview discussion of the mechanics of an accurate restored bone model 28 will first be given before discussing any of the bone restoration procedures disclosed herein. While this overview discussion is given in the context of a knee joint 14 and, more particularly, a femur restored bone model 28A and a tibia restored bone model 28B, it should be remembered that this discussion is applicable to other joints (e.g., elbows, ankles, wrists, hips, spine, etc.) and should not be considered as being limited to knee joints 14, but to included all joints.

Figure 3A:
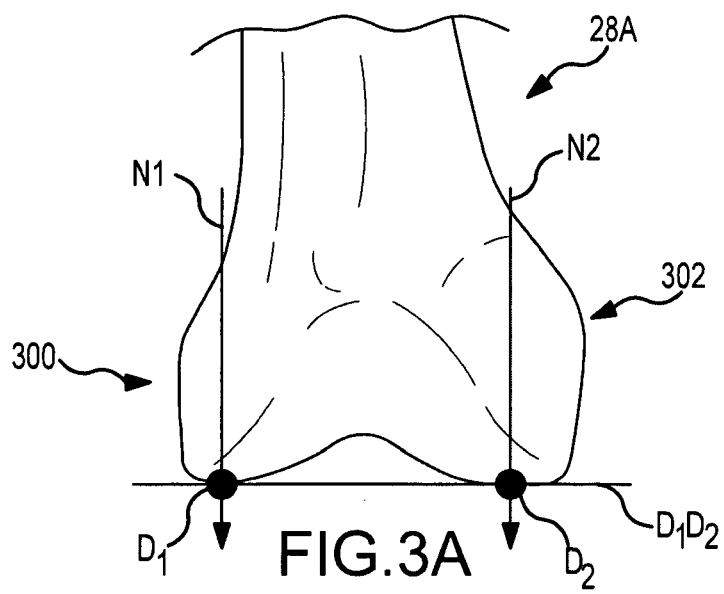
FIG. 3A is a coronal view of a distal or knee joint end of a femur restored bone model.

As shown in FIG. 3A, which is a coronal view of a distal or knee joint end of a femur restored bone model 28A, points $D_1$, $D_2$ represent the most distal tangent contact points of each of the femoral lateral and medial condyles 300, 302, respectively. In other words, points $D_1$, $D_2$ represent the lowest contact points of each of the femoral lateral and medial condyles 300, 302 when the knee is in zero degree extension. Line $D_1D_2$ can be obtained by extending across the two tangent contact points $D_1$, $D_2$. In this femur restored bone model 28A, line $D_1D_2$ is parallel or nearly parallel to the joint line of the knee when the knee is in zero degree extension.

The reference line N1 is perpendicular to line $D_1D_2$ at point $D_1$ and can be considered to represent a corresponding 2D image slice 16 taken along line N1. The reference line N2 is perpendicular to line $D_1D_2$ at point $D_2$ and can be considered to represent a corresponding 2D image slice 16 taken along line N2. The cross-sectional 2D image slices 16 taken along lines N1, N2 are perpendicular or nearly perpendicular to the tangent line $D_1D_2$ and joint line.

Figure 3B:
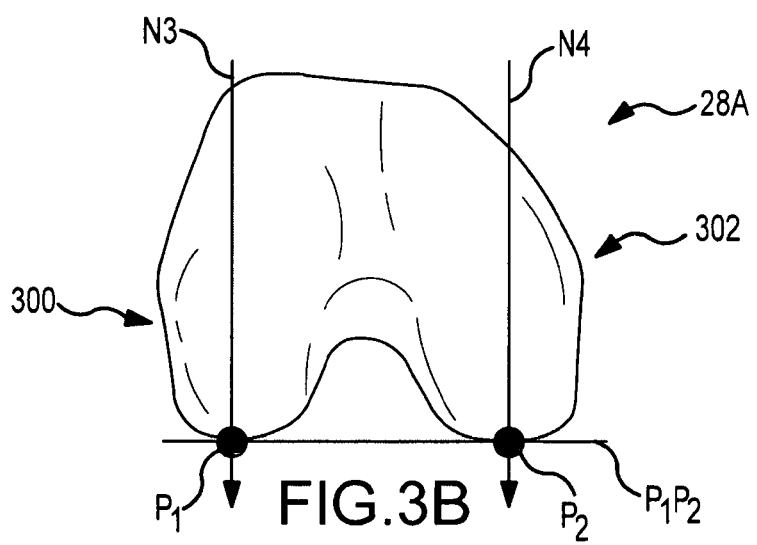
FIG. 3B is an axial view of a distal or knee joint end of a femur restored bone model.

As shown in FIG. 3B, which is an axial view of a distal or knee joint end of a femur restored bone model 28A, points $P_1$, $P_2$ represent the most posterior tangent contact points of each of the femoral lateral and medial condyles 300, 302, respectively. In other words, points $P_1$, $P_2$ represent the lowest contact points of each of the femoral lateral and medial condyles 300, 302 when the knee is in 90 degree extension. Line $P_1P_2$ can be obtained by extending across the two tangent contact points $P_1$, $P_2$. In this femur restored bone model 28A, line $P_1P_2$ is parallel or nearly parallel to the joint line of the knee when the knee is in 90 degree flexion.

The reference line N3 is perpendicular to line $P_1P_2$ at point $P_1$ and can be considered to represent a corresponding 2D image slice 16 taken along line N3. In some instances, the lines N1, N3 may occupy generally the same space on the femur restored bone model 28A or lines N1, N3 may be offset to a greater or lesser extent from each other along the joint line of the knee. The reference line N4 is perpendicular to line $P_1P_2$ at point $P_2$ and can be considered to represent a corresponding 2D image slice 16 taken along line N4. In some instances, the lines N2, N4 may occupy generally the same space on the femur restored bone model 28A or lines N2, N4 may be offset to a greater or lesser extent from each other along the joint line of the knee. The cross-sectional 2D image slices 16 taken along lines N3, N4 are perpendicular or nearly perpendicular to the tangent line $P_1P_2$ and joint line.

Figure 3C:
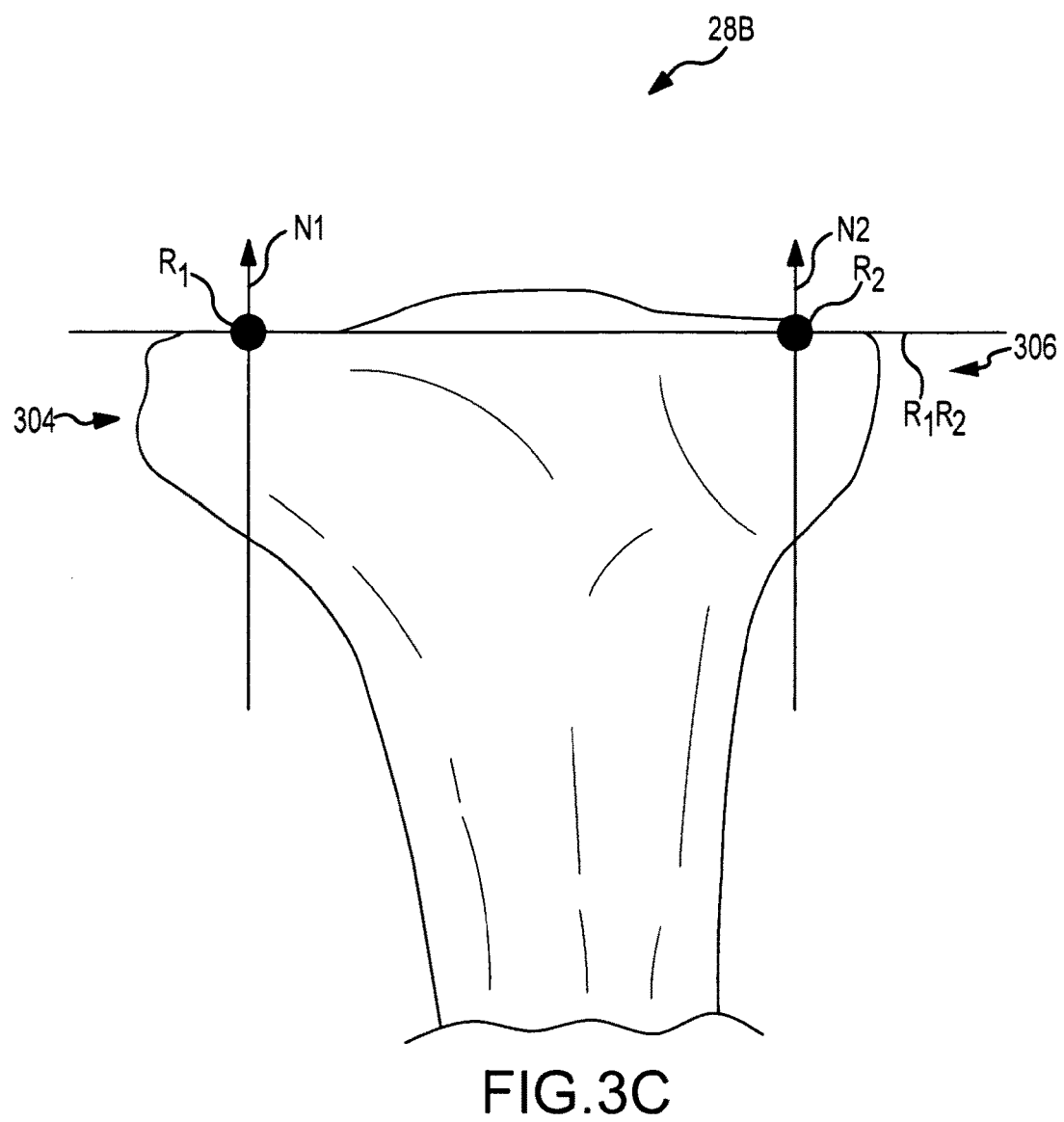
FIG. 3C is a coronal view of a proximal or knee joint end of a tibia restored bone model.

As shown in FIG. 3C, which is a coronal view of a proximal or knee joint end of a tibia restored bone model 28B, points $R_1$, $R_2$ represent the lowest tangent contact points of each of the tibial lateral and medial plateaus 304, 306, respectively. In other words, points $R_1$, $R_2$ represent the lowest points of contact of the tibia plateau with the femur condyles when the knee is in zero degree extension. Line $R_1R_2$ can be obtained by extending across the two tangent contact points $R_1$, $R_2$. In this tibia restored bone model 28B, line $R_1R_2$ is parallel or nearly parallel to the joint line of the knee when the knee is in zero degree extension. Also, when the knee joint is in zero degree extension, line $R_1R_2$ is parallel or nearly parallel to line $D_1D_2$. When the knee joint is in 90 degree extension, line $R_1R_2$ is parallel or nearly parallel to line $P_1P_2$. The reference line N1 is perpendicular to line $R_1R_2$ at point $R_1$ and can be considered to represent a corresponding 2D image slice 16 taken along line N1. The reference line N2 is perpendicular to line $R_1R_2$ at point $R_2$ and can be considered to represent a corresponding 2D image slice 16 taken along line N2. The cross-sectional 2D image slices 16 taken along lines N1, N2 are perpendicular or nearly perpendicular to the tangent line $R_1R_2$ and joint line. Because both the femur and tibia restored bone modesl 28A, 28B represent the knee joint 14 prior to degeneration or damage, lines N1, N2 of the femur restored model 28A in FIG. 1A align with and may be the same as lines N1, N2 of the tibia restored bone model 28B when the knee joint is in zero degree extension. Thus, points $D_1$, $D_2$ align with points $R_1$, $R_2$ when the knee joint is in zero degree extension.

Figure 3D:
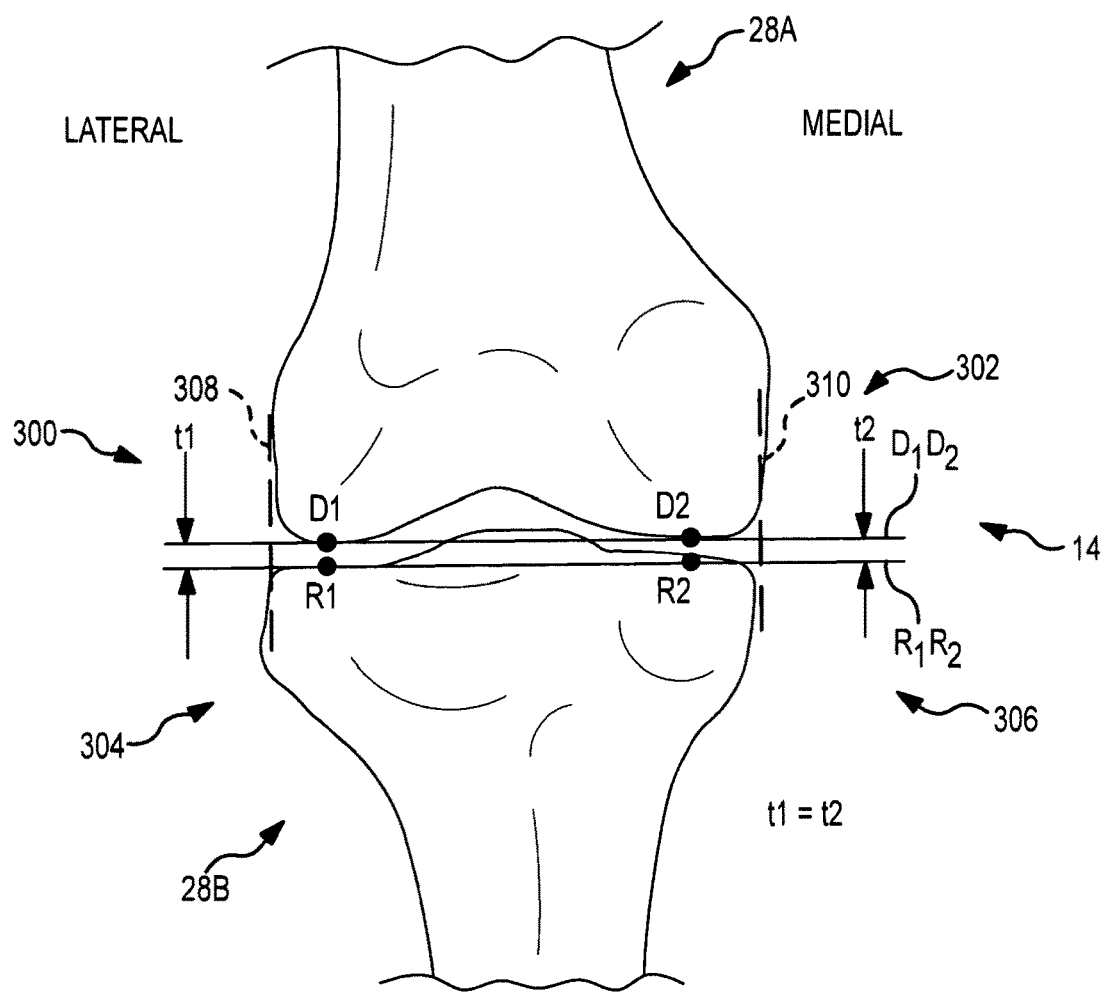
FIG. 3D represents the femur and tibia restored bone models in the views depicted in FIGS. 3A and 3C positioned together to form a knee joint.

FIG. 3D represents the femur and tibia restored bone models 28A, 28B in the views depicted in FIGS. 3A and 3C positioned together to form a knee joint 14. FIG. 3D shows the varus/valgus alignment of the femur and tibia restored bone models 28A, 28B intended to restore the patient's knee joint 14 back to its pre-OA or pre-degenerated state, wherein the knee joint 14 is shown in zero degree extension and in its natural alignment (e.g., neutral, varus or valgus) as the knee joint existed prior to degenerating. The respective locations of the lateral collateral ligament ("LCL") 308 and medial collateral ligament ("MCL") 310 are indicated in FIG. 3D by broken lines and serve as stabilizers for the side-to-side stability of the knee joint 14.

As can be understood from FIGS. 3A, 3C and 3D, when the knee joint 14 is in zero degree extension, lines N1, N2 are parallel or nearly parallel to the LCL 308 and MCL 310. Gap t1 represents the distance between the tangent contact point $D_1$ of the femoral lateral condyle 300 and the tangent contact point $R_1$ of the tibia lateral plateau 304. Gap t2 represents the distance between the tangent contact point $D_2$ of the femoral medial condyle 302 and the tangent contact point $R_2$ of the medial tibia plateau 306. For a properly restored knee joint 14, as depicted in FIG. 3D, in one embodiment, with respect to varus/valgus rotation and alignment, t1 is substantially equal to t2 such that the difference between t1 and t2 is less than one millimeter (e.g., [t1-t2] <<1 mm). Accordingly, line $D_1D_2$ is parallel or nearly parallel to the joint line and line $R_1R_2$.

Figure 3E:
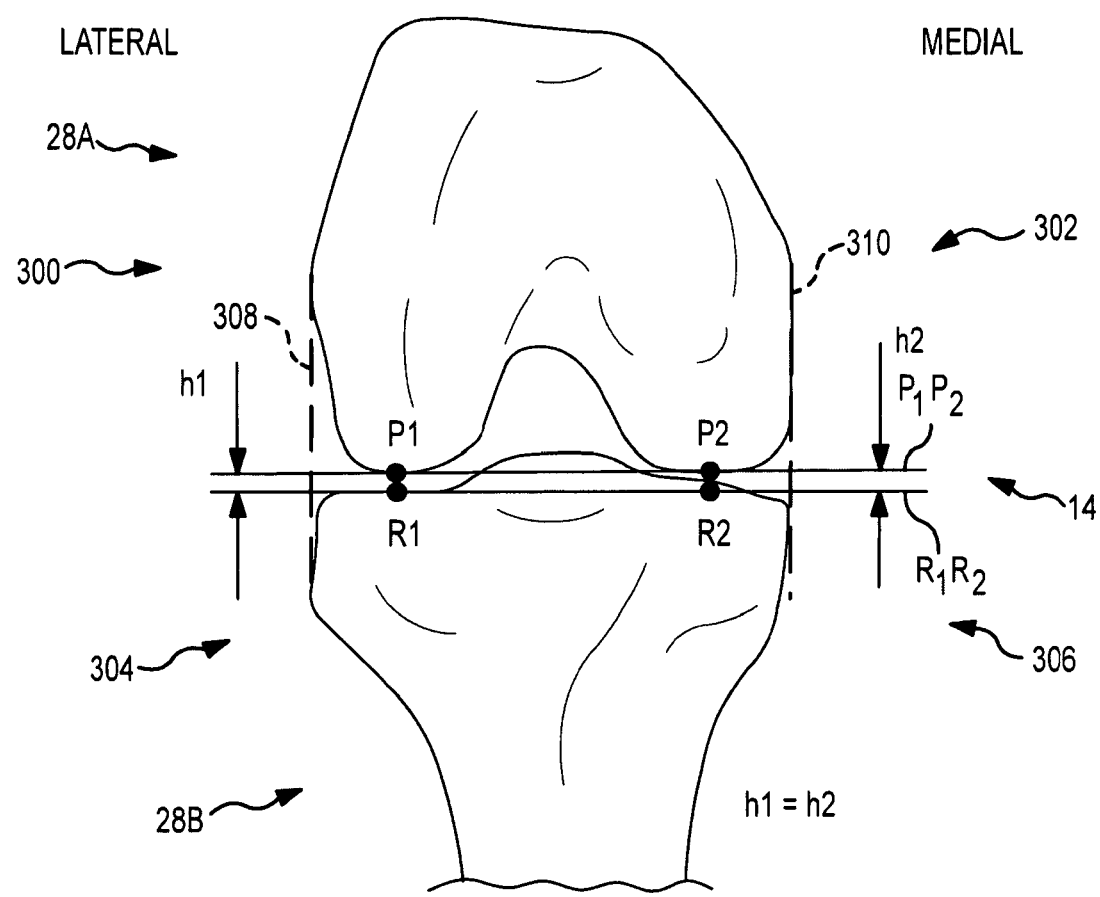
FIG. 3E represents the femur and tibia restored bone models in the views depicted in FIGS. 3B and 3C positioned together to form a knee joint.

FIG. 3E represents the femur and tibia restored bone models 28A, 28B in the views depicted in FIGS. 3B and 3C positioned together to form a knee joint 14. FIG. 3E shows the varus/valgus alignment of the femur and tibia restored bone models 28A, 28B intended to restore the patient's knee joint 14 back to its pre-OA or pre-degenerated state, wherein the knee joint 14 is shown in 90 degree flexion and in its natural alignment (e.g., neutral, varus or valgus) as the knee joint existed prior to degenerating. The respective locations of the lateral collateral ligament ("LCL") 308 and medial collateral ligament ("MCL") 310 are indicated in FIG. 3E by broken lines and serve as stabilizers for the side-to-side stability of the knee joint 14.

As can be understood from FIGS. 3B, 3C and 3E, when the knee joint 14 is in 90 degree flexion, lines N3, N4 are parallel or nearly parallel to the LCL 308 and MCL 310. Gap h1 represents the distance between the tangent contact point $P_1$ of the femoral lateral condyle 300 and the tangent contact point $R_1$ of the tibia lateral plateau 304. Gap h2 represents the distance between the tangent contact point $P_2$ of the femoral medial condyle 302 and the tangent contact point $R_2$ of the medial tibia plateau 306. For a properly restored knee joint 14, as depicted in FIG. 3E, in one embodiment, with respect to varus/valgus rotation and alignment, h1 is substantially equal to h2 such that the difference between h1 and h2 is less than one millimeter (e.g., [h1−h2]<<1 mm). Accordingly, line $P_1P_2$ is parallel or nearly parallel to the joint line and line $R_1R_2$.

Figure 3F:
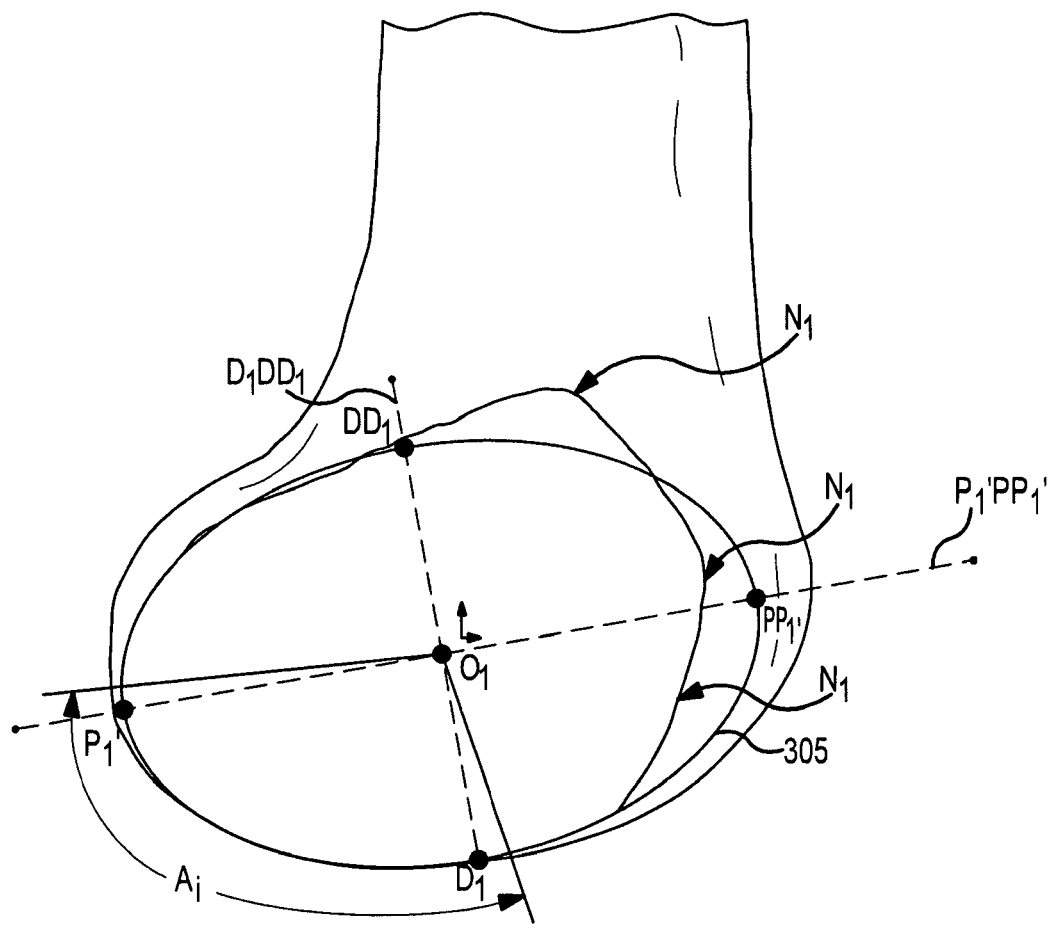
FIG. 3F is a sagittal view of the femoral medial condyle ellipse and, more specifically, the N1 slice of the femoral medial condyle ellipse as taken along line N1 in FIG. 3A.

FIG. 3F is a sagittal view of the femoral medial condyle ellipse 300 and, more specifically, the N1 slice of the femoral medial condyle ellipse 300 as taken along line N1 in FIG. 3A. The contour line $N_1$ in FIG. 3F represents the N1 image slice of the femoral medial condyle 300. The N1 image slice may be generated via such imaging methods as MRI, CT, etc. An ellipse contour 305 of the medial condyle 300 can be generated along contour line $N_1$. The ellipse 305 corresponds with most of the contour line $N_1$ for the N1 image slice, including the posterior and distal regions of the contour line $N_1$ and portions of the anterior region of the contour line $N_1$. As can be understood from FIG. 3F and discussed in greater detail below, the ellipse 305 provides a relatively close approximation of the contour line $N_1$ in a region of interest or region of contact $A_i$ that corresponds to an region of the femoral medial condyle surface that contacts and displaces against the tibia medial plateau.

As can be understood from FIGS. 3A, 3B and 3F, the ellipse 305 can be used to determine the distal extremity of the femoral medial condyle 300, wherein the distal extremity is the most distal tangent contact point $D_1$ of the femoral medial condyle 300 of the N1 slice. Similarly, the ellipse 305 can be used to determine the posterior extremity of the femoral medial condyle 300, wherein the posterior extremity is the most posterior tangent contact point $P_1'$ of the femoral medial condyle 300 of the N1 slice. The ellipse origin point $O_1$, the ellipse major axis $P_1'PP_1'$ and ellipse minor axis $D_1DD_1$ can be obtained based on the elliptical shape of the N1 slice of the medial condyle 300 in conjunction with well-known mathematical calculations for determining the characteristics of an ellipse.

As can be understood from FIG. 3F and as mentioned above, the region of contact $A_i$ represents or corresponds to the overlapping surface region between the medial tibia plateau 304 and the femoral medial condyle 300 along the N1 image slice. The region of contact $A_i$ for the N1 image slice is approximately 120° of the ellipse 305 of the N1 image slice from just proximal the most posterior tangent contact point $P_1'$ to just anterior the most distal tangent contact point $D_1$.

Figure 3G:
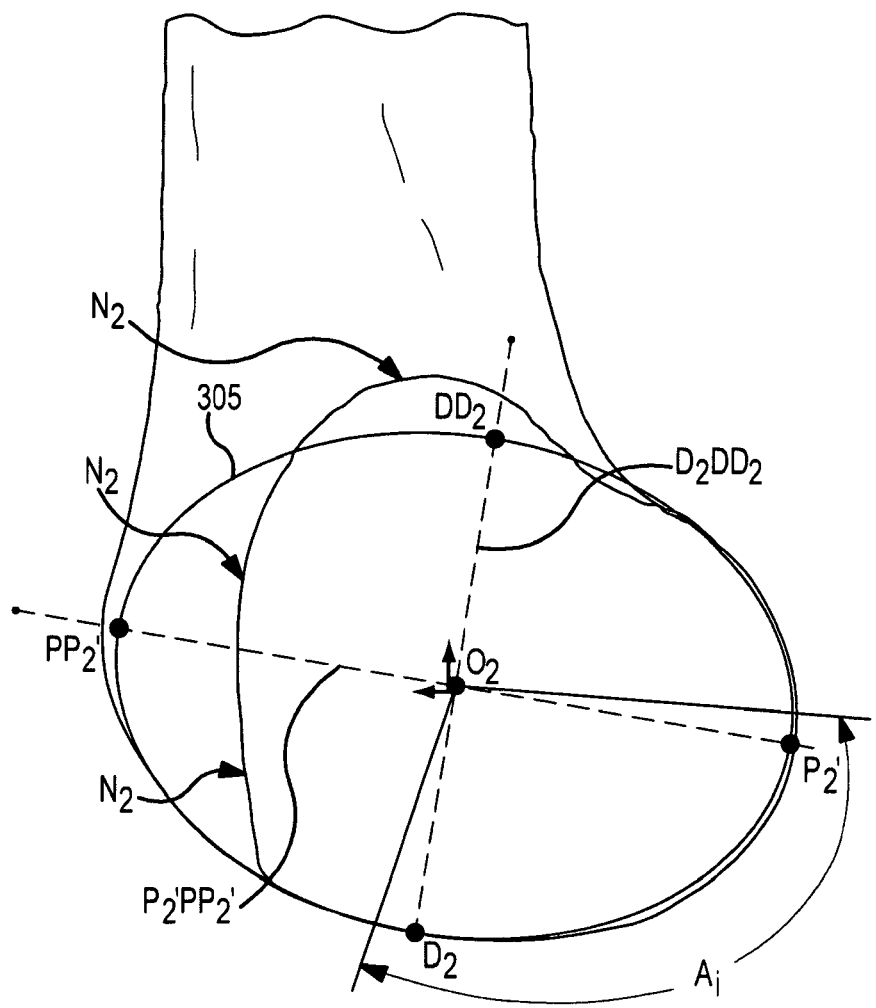
FIG. 3G is a sagittal view of the femoral lateral condyle ellipse and, more specifically, the N2 slice of the femoral lateral condyle ellipse as taken along line N2 in FIG. 3A.

FIG. 3G is a sagittal view of the femoral lateral condyle ellipse 302 and, more specifically, the N2 slice of the femoral lateral condyle ellipse 302 as taken along line N2 in FIG. 3A. The contour line $N_2$ in FIG. 3G represents the N2 image slice of the femoral lateral condyle 302. The N2 image slice may be generated via such imaging methods as MRI, CT, etc. An ellipse contour 305 of the lateral condyle 302 can be generated along contour line $N_2$. The ellipse 305 corresponds with most of the contour line $N_2$ for the N2 image slice, including the posterior and distal regions of the contour line $N_2$ and portions of the anterior region of the contour line $N_2$. As can be understood from FIG. 3G and discussed in greater detail below, the ellipse 305 provides a relatively close approximation of the contour line $N_2$ in a region of interest or region of contact $A_i$ that corresponds to an region of the femoral lateral condyle surface that contacts and displaces against the tibia lateral plateau.

As can be understood from FIGS. 3A, 3B and 3G, the ellipse 305 can be used to determine the distal extremity of the femoral lateral condyle 302, wherein the distal extremity is the most distal tangent contact point $D_2$ of the femoral lateral condyle 302 of the N2 slice. Similarly, the ellipse 305 can be used to determine the posterior extremity of the femoral lateral condyle 302, wherein the posterior extremity is the most posterior tangent contact point $P_2'$ of the femoral lateral condyle 302 of the N2 slice. The ellipse origin point $O_2$, the ellipse major axis $P_2'PP_2'$ and ellipse minor axis $D_2DD_2$ can be obtained based on the elliptical shape of the N2 slice of the lateral condyle 302 in conjunction with well-known mathematical calculations for determining the characteristics of an ellipse.

As can be understood from FIG. 3G and as mentioned above, the region of contact $A_i$ represents or corresponds to the overlapping surface region between the lateral tibia plateau 306 and the femoral lateral condyle 302 along the N2 image slice. The region of contact $A_i$ for the N2 image slice is approximately 120° of the ellipse 305 of the N2 image slice from just proximal the most posterior tangent contact point $P_2'$ to just anterior the most distal tangent contact point $D_2$.

Figure 3H:
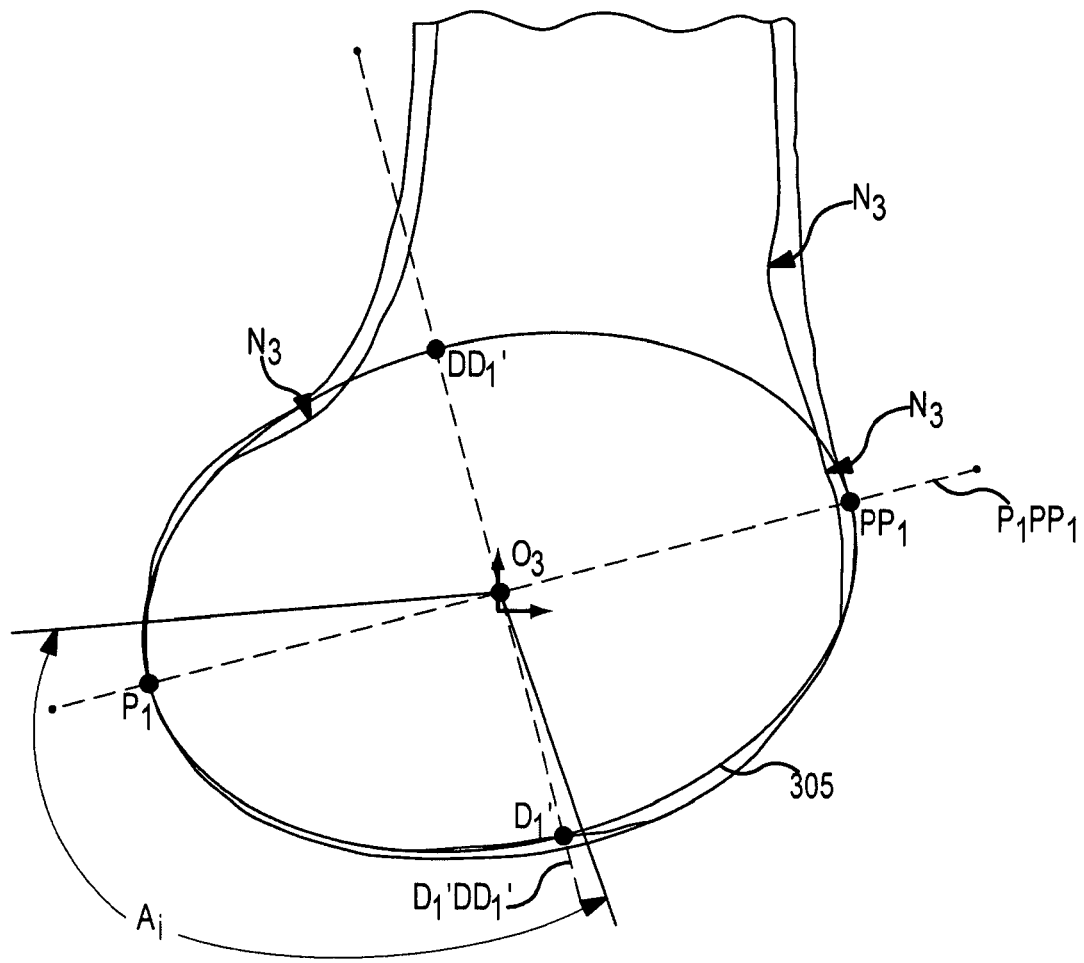
FIG. 3H is a sagittal view of the femoral medial condyle ellipse and, more specifically, the N3 slice of the femoral medial condyle ellipse as taken along line N3 in FIG. 3B.

FIG. 3H is a sagittal view of the femoral medial condyle ellipse 300 and, more specifically, the N3 slice of the femoral medial condyle ellipse 300 as taken along line N3 in FIG. 3B. The contour line $N_3$ in FIG. 3H represents the N3 image slice of the femoral medial condyle 300. The N3 image slice may be generated via such imaging methods as MRI, CT, etc. An ellipse contour 305 of the medial condyle 300 can be generated along contour line $N_3$. The ellipse 305 corresponds with most of the contour line $N_3$ for the N3 image slice, including the posterior and distal regions of the contour line $N_3$ and portions of the anterior region of the contour line $N_3$. As can be understood from FIG. 3H and discussed in greater detail below, the ellipse 305 provides a relatively close approximation of the contour line $N_3$ in a region of interest or region of contact $A_i$ that corresponds to an region of the femoral medial condyle surface that contacts and displaces against the tibia medial plateau.

As can be understood from FIGS. 3A, 3B and 3H, the ellipse 305 can be used to determine the distal extremity of the femoral medial condyle 300, wherein the distal extremity is the most distal tangent contact point $D_1'$ of the femoral medial condyle 300 of the N3 slice. Similarly, the ellipse 305 can be used to determine the posterior extremity of the femoral medial condyle 300, wherein the posterior extremity is the most posterior tangent contact point $P_1$ of the femoral medial condyle 300 of the N3 slice. The ellipse origin point $O_3$, the ellipse major axis $P_1PP_1$ and ellipse minor axis $D_1'DD_1'$ can be obtained based on the elliptical shape of the N3 slice of the medial condyle 300 in conjunction with well-known mathematical calculations for determining the characteristics of an ellipse.

As can be understood from FIG. 3H and as mentioned above, the region of contact $A_i$ represents or corresponds to the overlapping surface region between the medial tibia plateau 304 and the femoral medial condyle 300 along the N3 image slice. The region of contact $A_i$ for the N3 image slice is approximately 120° of the ellipse 305 of the N3 image slice from just proximal the most posterior tangent contact point $P_1$ to just anterior the most distal tangent contact point $D_1'$.

Figure 3I:
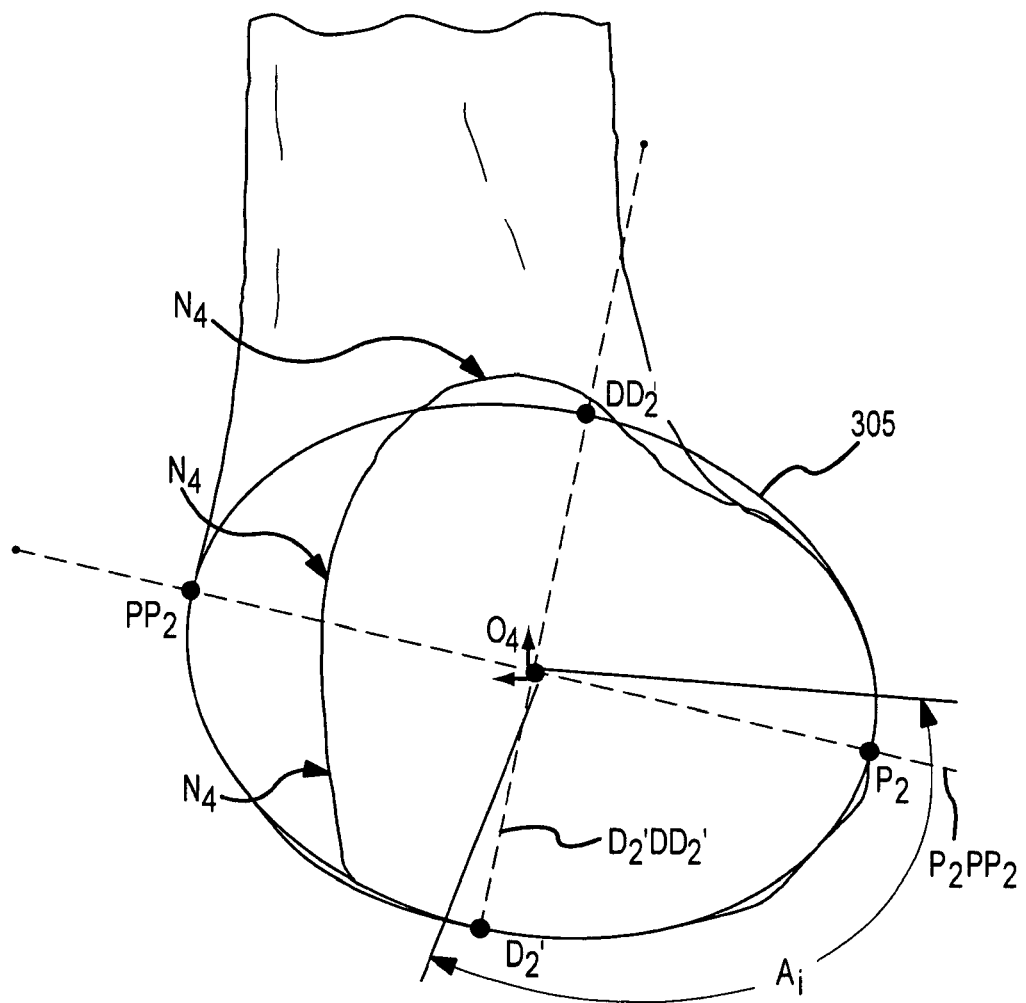
FIG. 3I is a sagittal view of the femoral lateral condyle ellipse and, more specifically, the N4 slice of the femoral lateral condyle ellipse as taken along line N4 in FIG. 3B.

FIG. 3I is a sagittal view of the femoral lateral condyle ellipse 302 and, more specifically, the N4 slice of the femoral lateral condyle ellipse 302 as taken along line N4 in FIG. 3B. The contour line $N_4$ in FIG. 3I represents the N4 image slice of the femoral lateral condyle 302. The N4 image slice may be generated via such imaging methods as MRI, CT, etc. An ellipse contour 305 of the lateral condyle 302 can be generated along contour line $N_4$. The ellipse 305 corresponds with most of the contour line $N_4$ for the N4 image slice, including the posterior and distal regions of the contour line $N_4$ and portions of the anterior region of the contour line $N_4$. As can be understood from FIG. 3G and discussed in greater detail below, the ellipse 305 provides a relatively close approximation of the contour line $N_4$ in a region of interest or region of contact $A_i$ that corresponds to an region of the femoral lateral condyle surface that contacts and displaces against the tibia lateral plateau.

As can be understood from FIGS. 3A, 3B and 3I, the ellipse 305 can be used to determine the distal extremity of the femoral lateral condyle 302, wherein the distal extremity is the most distal tangent contact point $D_2'$ of the femoral lateral condyle 302 of the N4 slice. Similarly, the ellipse 305 can be used to determine the posterior extremity of the femoral lateral condyle 302, wherein the posterior extremity is the most posterior tangent contact point $P_2$ of the femoral lateral condyle 302 of the N4 slice. The ellipse origin point $O_4$, the ellipse major axis $P_2PP_2$ and ellipse minor axis $D_2'DD_2'$ can be obtained based on the elliptical shape of the N4 slice of the lateral condyle 302 in conjunction with well-known mathematical calculations for determining the characteristics of an ellipse.

As can be understood from FIG. 3I and as mentioned above, the region of contact $A_i$ represents or corresponds to the overlapping surface region between the lateral tibia plateau 306 and the femoral lateral condyle 302 along the N4 image slice. The region of contact $A_i$ for the N4 image slice is approximately 120° of the ellipse 305 of the N4 image slice from just proximal the most posterior tangent contact point $P_2$ to just anterior the most distal tangent contact point $D_2'$.

While the preceding discussion is given in the context of image slices N1, N2, N3 and N4, of course similar elliptical contour lines, ellipse axes, tangent contact points and contact regions may be determined for the other image slices generated during the imaging of the patient's joint and which are parallel to image slices N1, N2, N3 and N4.

d. Employing Vectors From a Reference Side of a Joint to a Damaged Side of a Joint and Extending the Contour Lines of the Damaged Side to Meet the Vectors to Restore the Damaged Side A discussion of methods for determining reference vectors from a reference side of a joint bone for use in restoring a damaged side of the joint bone is first given, followed by specific examples of the restoration process in the context of MRI images. While this overview discussion is given in the context of a knee joint 14 and, more particularly, femur and tibia bone models 22A, 22B being converted image slice by slice into femur and tibia restored bone models 28A, 28B, it should be remembered that this discussion is applicable to other joints (e.g., elbows, ankles, wrists, hips, spine, etc.) and should not be considered as being limited to knee joints 14, but to included all joints. Also, while the image slices are discussed in the context of MRI image slices, it should be remembered that this discussion is applicable to all types of medical imaging, including CT scanning.

Figure 4A:
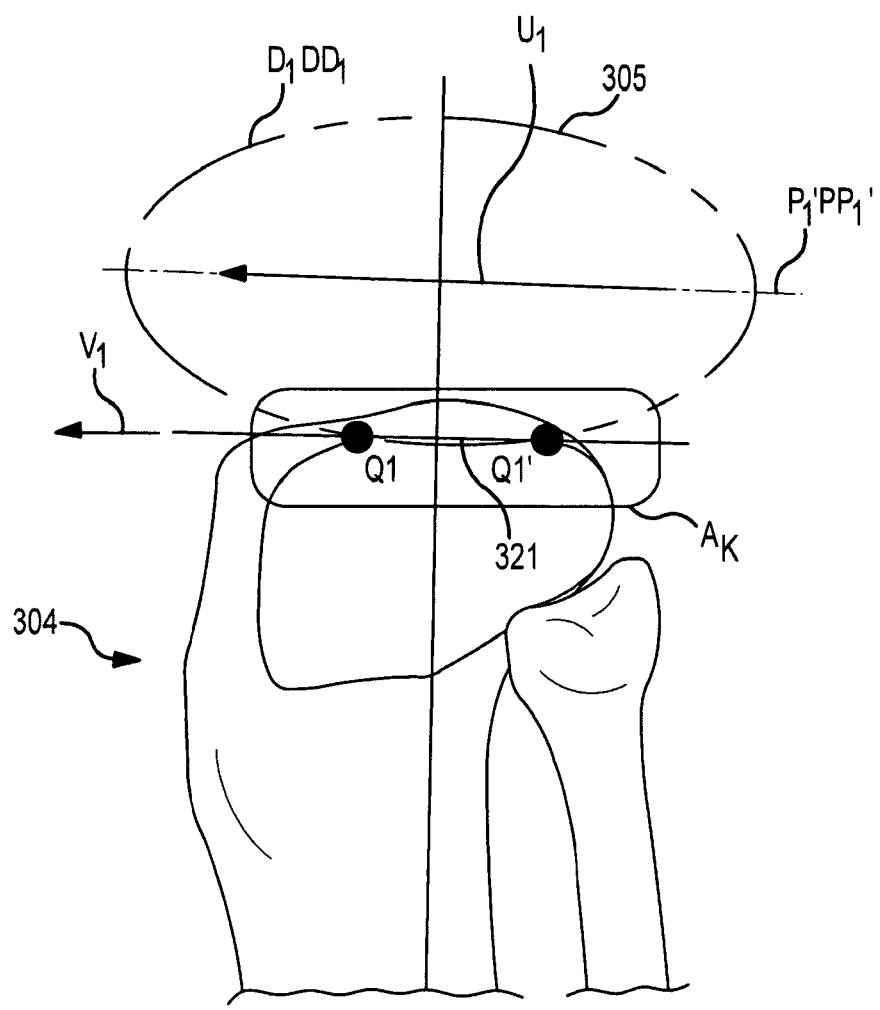
FIG. 4A is a sagital view of the lateral tibia plateau with the lateral femur condyle ellipse of the N1 slice of FIG. 3F superimposed thereon.
Figure 4B:
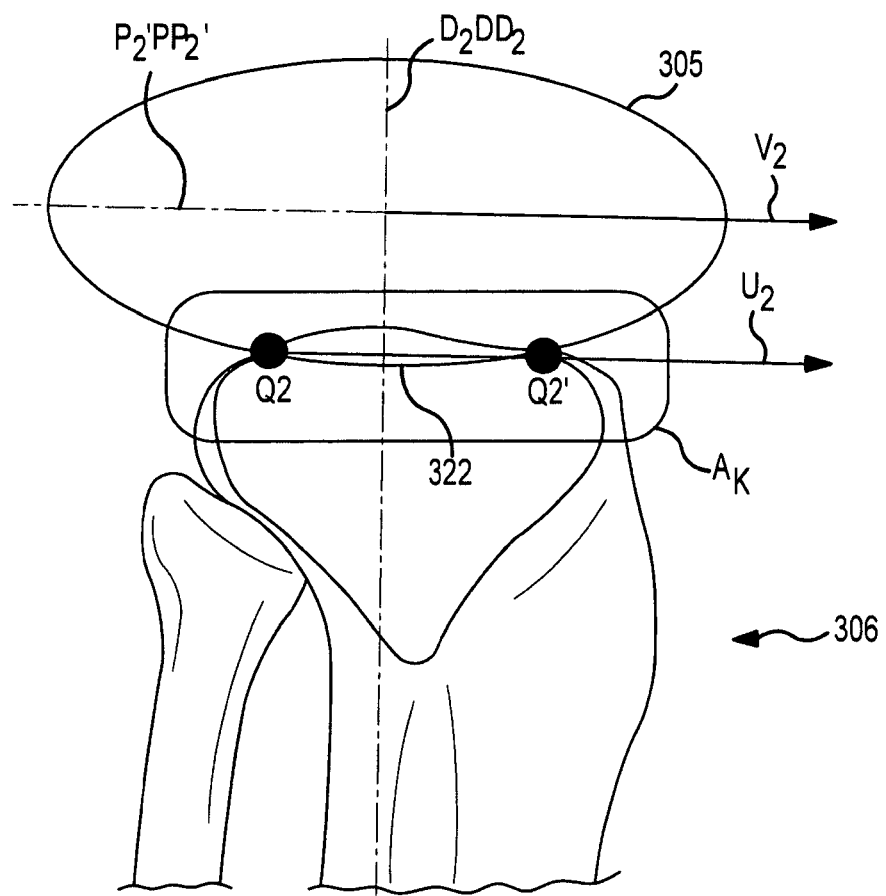
FIG. 4B is a sagital view of the medial tibia plateau with the lateral femur condyle ellipse of the N2 slice of FIG. 3G superimposed thereon.

For a discussion of the motion mechanism of the knee and, more specifically, the motion vectors associated with the motion mechanism of the knee, reference is made to FIGS. 4A and 4B. FIG. 4A is a sagital view of the lateral tibia plateau 304 with the lateral femur condyle ellipse 305 of the N1 slice of FIG. 3F superimposed thereon. FIG. 4B is a sagital view of the medial tibia plateau 306 with the lateral femur condyle ellipse 305 of the N2 slice of FIG. 3G superimposed thereon.

The motion mechanism for a human knee joint operates as follows. The femoral condyles glide on the corresponding tibia plateaus as the knee moves, and in a walking theme, as a person's leg swings forward, the femoral condyles and the corresponding tibia plateaus are not under the compressive load of the body. Thus, the knee joint movement is a sliding motion of the tibia plateaus on the femoral condyles coupled with a rolling of the tibia plateaus on the femoral condyles in the same direction. The motion mechanism of the human knee as the femur condyles and tibia plateaus move relative to each other between zero degree flexion and 90 degree flexion has associated motion vectors. As discussed below, the geometrical features of the femur condyles and tibia plateaus can be analyzed to determine vectors $U_1$, $U_2$, $V_1$, $V_2$, $V_3$, $V_4$ that are associated with image slices N1, N2, N3 and N4. These vectors $U_1$, $U_2$, $V_1$, $V_2$, $V_3$, $V_4$ correspond to the motion vectors of the femur condyles and tibia plateaus moving relative to each other. The determined vectors $U_1$, $U_2$, $V_1$, $V_2$, $V_3$, $V_4$ associated with a healthy side of a joint 14 can be applied to a damaged side of a joint 14 to restore the bone model 22 to create a restored bone model 28.

In some embodiments of the bone restoration process disclosed herein and as just stated, the knee joint motion mechanism may be utilized to determine the vector references for the restoration of bone models 22 to restored bone models 28. As can be understood from a comparison of FIGS. 3F and 3G to FIGS. 4A and 4B, the $U_1$ and $U_2$ vectors respectively correspond to the major axes $P_1'PP_1'$ and $P_2'PP_2'$ of the ellipses 305 of the N1 and N2 slices. Since the major axes $P_1'PP_1'$ and $P_2'PP_2'$ exist in the N1 and N2 slices, which are planes generally perpendicular to the joint line, the $U_1$ and $U_2$ vectors may be considered to represent both vector lines and vector planes that are perpendicular to the joint line.

The $U_1$ and $U_2$ vectors are based on the joint line reference between the femur and the tibia from the zero degree flexion (full extension) to 90 degree flexion. The $U_1$ and $U_2$ vectors represent the momentary sliding movement force from zero degree flexion of the knee to any degree of flexion up to 90 degree flexion. As can be understood from FIGS. 4A and 4B, the $U_1$ and $U_2$ vectors, which are the vectors of the femoral condyles, are generally parallel to and project in the same direction as the $V_1$ and $V_2$ vectors of the tibia plateaus 321, 322. The vector planes associated with these vectors $U_1$, $U_2$, $V_1$, $V_2$ are presumed to be parallel or nearly parallel to the joint line of the knee joint 14 represented by restored bone model 28A, 28B such as those depicted in FIGS. 3D and 3E.

As shown in FIGS. 4A and 4B, the distal portion of the ellipses 305 extend along and generally correspond with the curved surfaces 321, 322 of the tibia plateaus. The curved portions 321, 322 of the tibia plateaus that generally correspond with the distal portions of the ellipses 305 represent the tibia contact regions $A_k$, which are the regions that contact and displace along the femur condyles and correspond with the condyle contact regions $A_i$ discussed with respect to FIGS. 3F-3I.

Figure 4C:
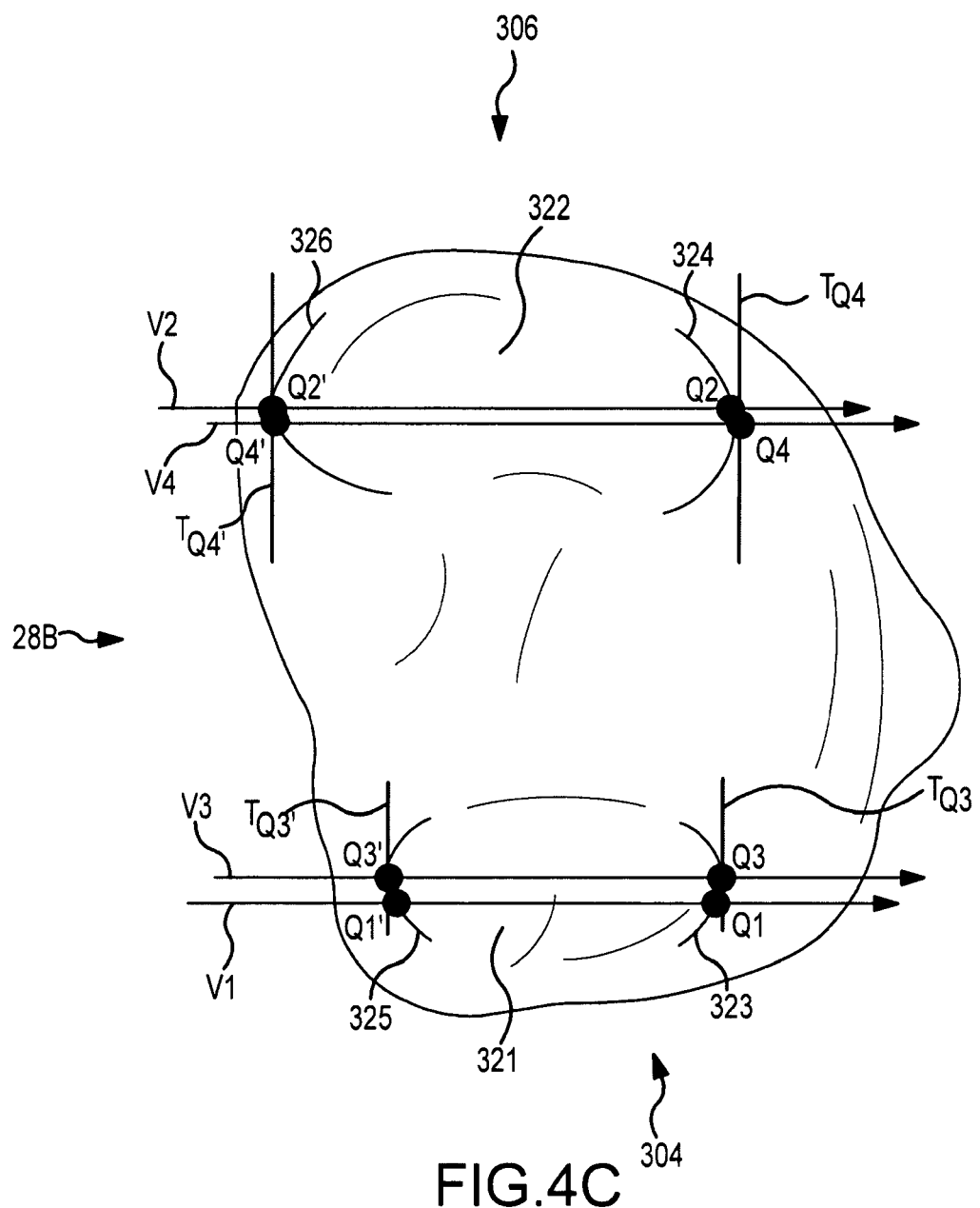
FIG. 4C is a top view of the tibia plateaus of a restored tibia bone model.
Figure 4D:
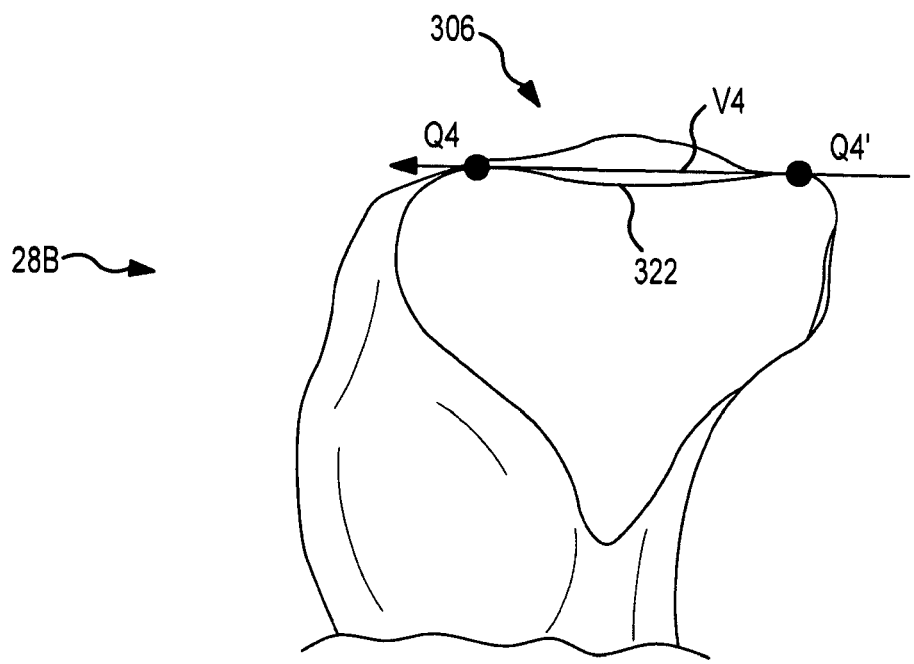
FIG. 4D is a sagital cross section through a lateral tibia plateau of the restored bone model 28B of FIG. 4C and corresponding to the N3 image slice of FIG. 3B.
Figure 4E:
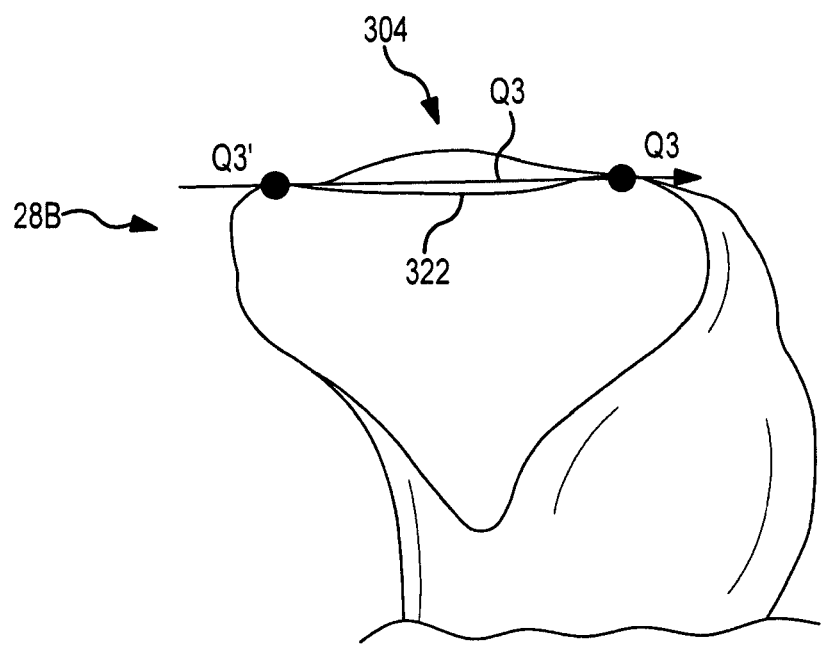
FIG. 4E is a sagital cross section through a medial tibia plateau of the restored bone model of FIG. 4C and corresponding to the N4 image slice of FIG. 3B.

For a discussion of motion vectors associated with the tibia plateaus, reference is made to FIGS. 4C-4E. FIG. 4C is a top view of the tibia plateaus 304, 306 of a restored tibia bone model 28B. FIG. 4D is a sagital cross section through a lateral tibia plateau 304 of the restored bone model 28B of FIG. 4C and corresponding to the N3 image slice of FIG. of FIG. 3B. FIG. 4E is a sagital cross section through a medial tibia plateau 306 of the restored bone model 28B of FIG. 4C and corresponding to the N4 image slice of FIG. of FIG. 3B.

As shown in FIGS. 4C-4E, each tibia plateau 304, 306 includes a curved recessed condyle contacting surface 321, 322 that is generally concave extending anterior/posterior and medial/lateral. Each curved recessed surface 321, 322 is generally oval in shape and includes an anterior curved edge 323, 324 and a posterior curved edge 325, 326 that respectively generally define the anterior and posterior boundaries of the condyle contacting surfaces 321, 322 of the tibia plateaus 304, 306. Depending on the patient, the medial tibia plateau 306 may have curved edges 324, 326 that are slightly more defined than the curved edges 323, 325 of the lateral tibia plateau 304.

Anterior tangent lines $T_{Q3}$, $T_{Q4}$ can be extended tangentially to the most anterior location on each anterior curved edge 323, 324 to identify the most anterior points Q3, Q4 of the anterior curved edges 323, 324. Posterior tangent lines $T_{Q3'}$, $T_{Q4'}$ can be extended tangentially to the most posterior location on each posterior curved edge 325, 326 to identify the most posterior points Q3', Q4' of the posterior curved edges 325, 326. Such anterior and posterior points may correspond to the highest points of the anterior and posterior portions of the respective tibia plateaus.

Vector line V3 extends through anterior and posterior points Q3, Q3', and vector line V4 extends through anterior and posterior points Q4, Q4'. Each vector line V3, V4 may align with the lowest point of the anterior-posterior extending groove/valley that is the elliptical recessed tibia plateau surface 321, 322. The lowest point of the anterior-posterior extending groove/valley of the elliptical recessed tibia plateau surface 321, 322 may be determined via simple ellipsoid calculus. Each vector V3, V4 will be generally parallel to the anterior-posterior extending valleys of its respective elliptical recessed tibia plateau surface 321, 322 and will be generally perpendicular to it respective tangent lines $T_{Q3}$, $T_{Q4}$, $T_{Q3'}$, $T_{Q4'}$. The anterior-posterior extending valleys of the elliptical recessed tibia plateau surfaces 321, 322 and the vectors V3, V4 aligned therewith may be generally parallel with and even exist within the N3 and N4 image slices depicted in FIG. 3B.

As can be understood from FIGS. 4A-4E, the $V_3$ and $V_4$ vectors, which are the vectors of the tibia plateaus, are generally parallel to and project in the same direction as the other tibia plateau vectors $V_1$ and $V_2$ and, as a result, the femur condyle vectors $U_1$, $U_2$. The vector planes associated with these vectors $U_1$, $U_2$, $V_1$, $V_2$, $V_3$ and $V_4$ are presumed to be parallel or nearly parallel to the joint line of the knee joint 14 represented by restored bone models 28A, 28B such as those depicted in FIGS. 3D and 3E.

As indicated in FIGS. 4A-4C, tibia plateau vectors $V_1$ and $V_2$ in the N1 and N2 image slices can be obtained by superimposing the femoral condyle ellipses 305 of the N1 and N2 image slices onto their respective tibia plateaus. The ellipses 305 correspond to the elliptical tibia plateau surfaces 321, 322 along the condyle contact regions $A_k$ of the tibia plateaus 304, 306. The anterior and posterior edges 323, 324, 325, 326 of the elliptical tibia plateau surfaces 321, 322 can be determined at the locations where the ellipses 305 cease contact with the plateau surfaces 321. 322. These edges 323, 324, 325, 326 are marked as anterior and posterior edge points Q1, Q1', Q2, Q2' in respective image slices N1 and N2. Vector lines V1 and V2 are defined by being extended through their respective edge points Q1, Q1', Q2, Q2'.

As can be understood from FIG. 4C, image slices N1, N2, N3 and N4 and their respective vectors $V_1$, $V_2$, $V_3$ and $V_4$ may be medially-laterally spaced apart a greater or lesser extent, depending on the patient. With some patients, the N1 and N3 image slices and/or the N2 and N4 image slices may generally medially-laterally align.

While the preceding discussion is given with respect to vectors $U_1$, $U_2$, $V_1$, $V_2$, $V_3$ and $V_4$, contact regions $A_i$, $A_k$, and anterior and posterior edge points Q1, Q1', Q2, Q2', Q3, Q3', Q4, Q4' associated with image slices N1, N2, N3 and N4, similar vectors, contact regions, and anterior and posterior edge points can be determined for the other image slices 16 used to generate the 3D computer generated bone models 22 (see [block 100]-[block 110] of FIGS. 1A-1C).

As illustrated via the following examples given with respect to MRI slices, vectors similar to the $U_1$, $U_2$, $V_1$, $V_2$, $V_3$, $V_4$ vectors of FIGS. 4A-4E can be employed in restoring image slice-by-image slice the bone models 22A, 22B into restored bone models 28A, 28B. For example, a bone model 22 includes a femur bone model 22A and a tibia bone model 22B. The bone models 22A, 22B are 3D bone-only computer generated models compiled via any of the above-mentioned 3D computer programs from a number of image slices 16, as discussed with respect to [blocks 100]-[block 110] of FIGS. 1A-1C. Depending on the circumstances and generally speaking, either the medial side of the bone models will be generally undamaged and the lateral side of the bone models will be damaged, or vice versa.

Figure 4F:
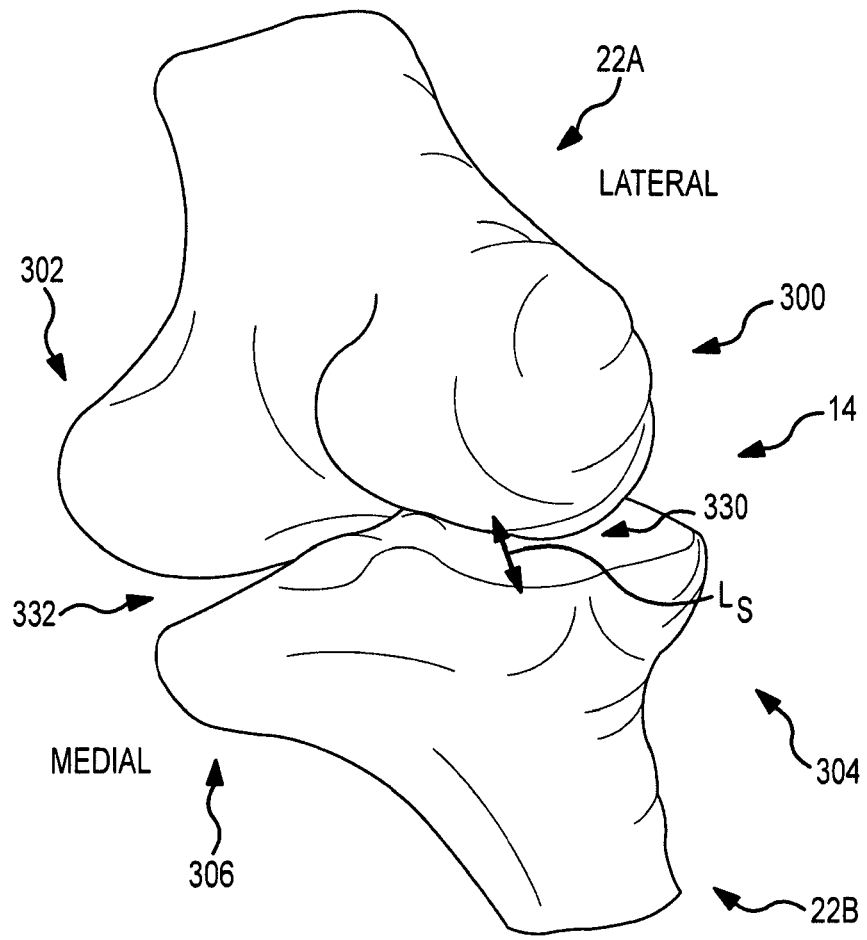
FIG. 4F is a posterior-lateral perspective view of femur and tibia bone models forming a knee joint.

For example, as indicated in FIG. 4F, which is a posterior-lateral perspective view of femur and tibia bone models 22A, 22B forming a knee joint 14, the medial sides 302, 306 of the bone models 22A, 22B are in a generally non-deteriorated condition and the lateral sides 300, 304 of the bone models 22A, 22B are in a generally deteriorated or damaged condition. The lateral sides 300, 304 of the femur and tibia bone models 22A, 22B depict the damaged bone attrition on the lateral tibia plateau and lateral femoral condyle. The lateral sides 300, 304 illustrate the typical results of OA, specifically joint deterioration in the region of arrow $L_S$ between the femoral lateral condyle 300 and the lateral tibia plateau 304, including the narrowing of the lateral joint space 330 as compared to medial joint space 332. As the medial sides 302, 306 of the bone models 22A, 22B are generally undamaged, these sides 302, 306 will be identified as the reference sides of the 3D bone models 22A, 22B (see [block 200] of FIG. 2). Also, as the lateral sides 300, 304 of the bone models 22A, 22B are damaged, these sides 300, 304 will be identified as the damaged sides of the 3D bone models 22A, 22B (see [block 200] of FIG. 2) and targeted for restoration, wherein the images slices 16 associated with the damaged sides 300, 304 of the bone models 22A, 22B are restored slice-by-slice.

Reference vectors like the $U_1$, $U_2$, $V_1$, $V_2$, $V_3$, $V_4$ vectors may be determined from the reference side of the bone models 22A, 22B (see [block 205] of FIG. 2). Thus, as can be understood from FIGS. 4B and 4F, since the medial sides 302, 306 are the reference sides 302, 306, the reference vectors $U_2$, $V_2$ $V_4$ may be applied to the damaged sides 300, 304 to restore the damaged sides 300, 304 2D image slice by 2D image slice (see [block 215]-[block 220] of FIG. 2). The restored image slices are then recompiled into a 3D computer generated model, the result being the 3D computer generated restored bone models 28A, 28B (see [block 225] of FIG. 2).

Figure 4G:
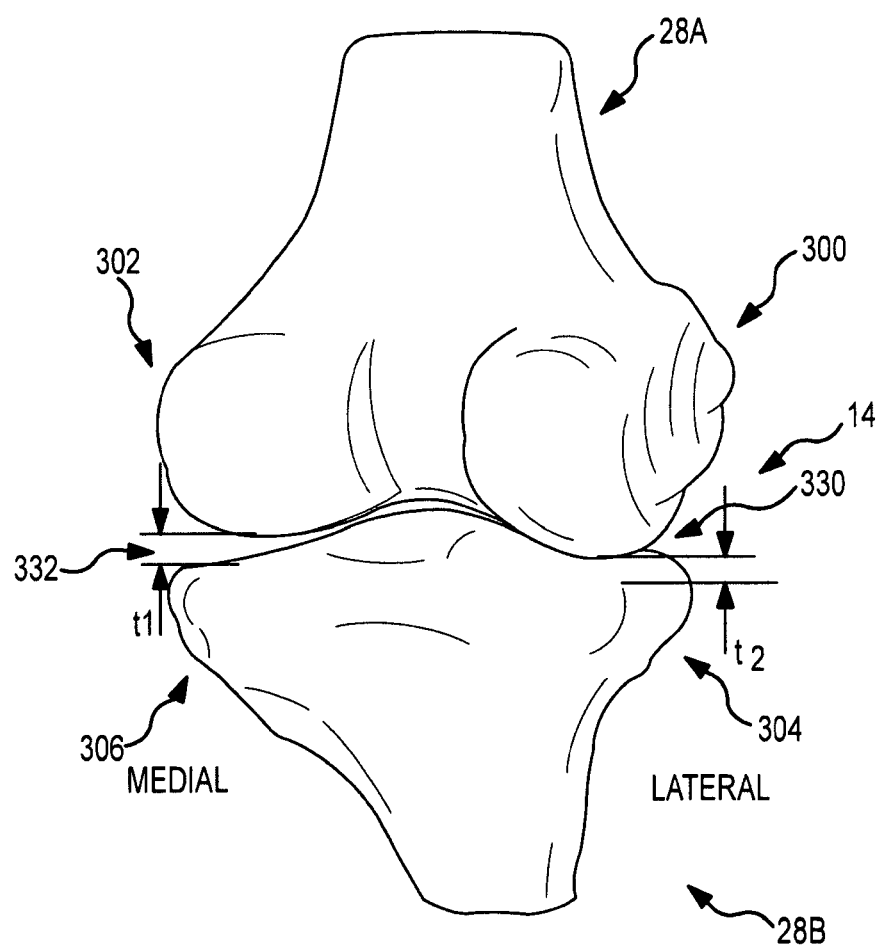
FIG. 4G is a posterior-lateral perspective view of femur and tibia restored bone models forming a knee joint.

As shown in FIG. 4G, which is a posterior-lateral perspective view of femur and tibia restored bone models 28A, 28B forming a knee joint 14, the lateral sides 300, 304 of the restored bone models 28A, 28B have been restored such that the lateral and medial joint spaces 330, 332 are generally equal. In other words, the distance t1 between the lateral femur condyle and lateral tibia plateau is generally equal to the distance t2 between the medial femur condyle and the medial tibia plateau.

The preceding discussion has occurred in the context of the medial sides 302, 306 being the reference sides and the lateral sides 300, 304 being the damaged sides; the reference vectors $U_2$, $V_2$ and $V_4$ of the medial sides 302, 306 being applied to the damaged sides 300, 304 in the process of restoring the damaged sides 300, 304. Of course, as stated above, the same process could occur in a reversed context, wherein the lateral sides 300, 304 are generally undamaged and are identified as the reference sides, and the medial sides 302, 306 are damaged and identified as the damaged sides. The reference vectors $U_1$, $V_1$ and $V_3$ of the lateral sides 300, 304 can then be applied to the damaged sides 302, 306 in the process of restoring the damaged sides 302, 306.

Multiple approaches are disclosed herein for identifying reference vectors and applying the reference vectors to a damaged side for the restoration thereof. For example, as can be understood from FIGS. 4B and 4F, where the medial sides 302, 306 are the undamaged reference sides 302, 304 and the lateral sides 300, 304 the damaged sides 300, 304, in one embodiment, the ellipses and vectors associated with the reference side femur condyle 302 (e.g., the ellipse 305 of the N2 slice and the vector $U_2$) can be applied to the damaged side femur condyle 300 and damaged side tibia plateau 304 to restore the damaged condyle 300 and damaged plateau 304. Alternatively or additionally, the ellipses and vectors associated with the reference side femur condyle 302 as applied to the reference side tibia plateau 306 (e.g., the ellipse 305 of the N2 slice and the vector $V_2$) can be applied to the damaged side femur condyle 300 and damaged side tibia plateau 304 to restore the damaged condyle 300 and damaged plateau 304. In another embodiment, as can be understood from FIGS. 4C, 4E and 4F, the vectors associated with the reference side tibia plateau 306 (e.g., the vector $V_4$) can be applied to the damaged side femur condyle 300 and damaged side tibia plateau 304 to restore the damaged condyle 300 and damaged plateau 304. Of course, if the conditions of the sides 300, 302, 304, 306 were reversed in FIG. 4F, the identification of the reference sides, the damaged sides, the reference vectors and the application thereof would be reversed from examples given in this paragraph.

Figure 5A:
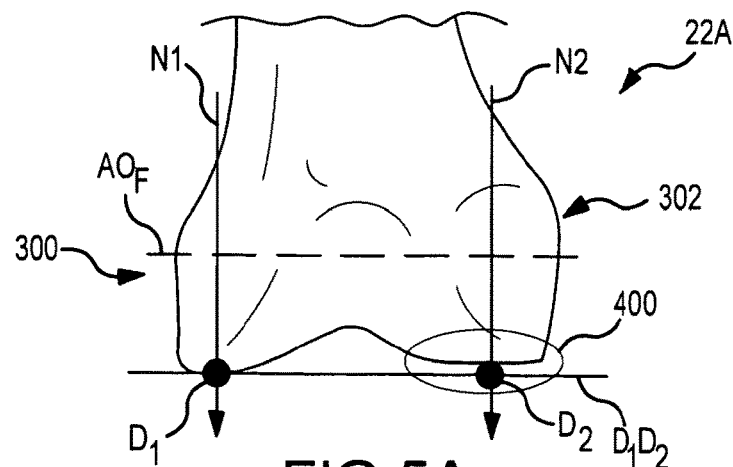
FIG. 5A is a coronal view of a femur bone model.
Figure 5B:
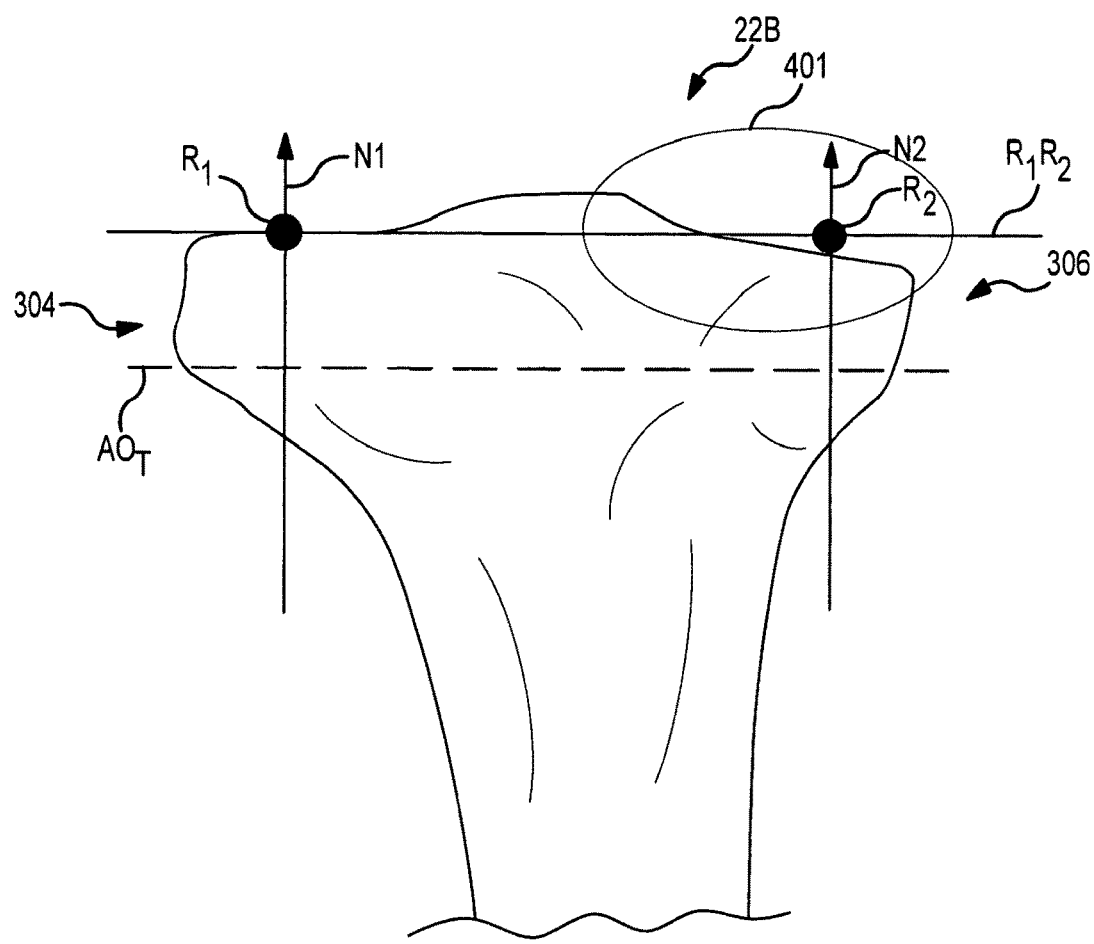
FIG. 5B is a coronal view of a tibia bone model.

1. Employing Vectors From a Femur Condyle of a Reference Side of a Knee Joint to Restore the Femur Condyle and Tibia Plateau of the Damaged Side For a discussion of a first scenario, wherein the medial sides 302, 306 are the damaged sides and the lateral sides 300, 304 are the reference sides, reference is made to FIGS. 5A-5B. FIG. 5A is a coronal view of a femur bone model 22A, and FIG. 5B is a coronal view of a tibia bone model 22B.

As shown in FIG. 5A, the medial femur condyle 302 is deteriorated in region 400 such that the most distal point of the medial condyle 302 fails to intersect point $D_2$ on line $D_1D_2$, which will be corrected once the femur bone model 22A is properly restored to a restored femur bone model 28A such as that depicted in FIG. 3A. As illustrated in FIG. 5B, the medial tibia plateau 306 is deteriorated in region 401 such that the lowest point of the medial plateau 306 fails to intersect point $R_2$ on line $R_1R_2$, which will be corrected once the tibia bone model 22B is properly restored to a restored tibia bone model 28B such as that depicted in FIG. 3C. Because the medial condyle 302 and medial plateau 306 of the bone models 22A, 22B are deteriorated, they will be identified as the damaged sides and targeted for restoration ([block 200] of FIG. 2).

As illustrated in FIG. 5A, the lateral condyle 300 and lateral plateau 304 of the bone models 22A, 22B are in a generally non-deteriorated state, the most distal point $D_1$ of the lateral condyle 300 intersecting line $D_1D_2$, and the lowest point $R_1$ of the lateral plateau 304 intersecting line $R_1R_2$. Because the lateral condyle 300 and lateral plateau 304 of the bone models 22A, 22B are generally in a non-deteriorated state, they will be identified as the reference sides and the source of information used to restore the damaged sides 302, 306 ([block 200] of FIG. 2).

As can be understood from FIGS. 3F, 4A and 5A, for most if not all of the image slices 16 of the lateral condyle 300, image slice information or data such as ellipses and vectors can be determined. For example, an ellipse 305 and vector $U_1$ can be determined for the N1 slice ([block 205] of FIG. 2). The data or information associated with one or more of the various slices 16 of the lateral condyle 300 is applied to or superimposed on one or more image slices 16 of the medial condyle 302 ([block 215] of FIG. 2). For example, as shown in FIG. 5C1, which is an N2 image slice of the medial condyle 302 as taken along the N2 line in FIG. 5A, data or information pertaining to the N1 slice is applied to or superimposed on the N2 image slice to determine the extent of restoration needed in deteriorated region 400. For example, the data or information pertaining to the N1 slice may be in the form of the N1 slice's ellipse 305-N1, vector $U_1$, ellipse axes $P_1'PP_1'$, $D_1DD_1$, etc. The ellipse 305-N1 will inherently contain its major and minor axis information, and the vector $U_1$ of the N1 slice will correspond to the major axis of the 305-N1 ellipse and motion vector of the femur condyles relative to the tibia plateaus. The major axis of the 305-N1 and the vector $U_1$ of the N1 slice are generally parallel to the joint line plane.

In a first embodiment, the N1 slice information may be applied only to the contour line of the N2 slice or another specific slice. In other words, information of a specific reference slice may be applied to a contour line of a single specific damaged slice with which the specific reference slice is coordinated with via manual selection or an algorithm for automatic selection. For example, in one embodiment, the N1 slice information may be manually or automatically coordinated to be applied only to the N2 slice contour line, and the N3 slice information may be manually or automatically coordinated to be applied only to the N4 slice contour line. Other reference side slice information may be similarly coordinated with and applied to other damaged side slice contours in a similar fashion. Coordination between a specific reference slice and a specific damaged slice may be according to various criteria, for example, similarity of the function and/or shape of the bone regions pertaining to the specific reference slice and specific damaged slice and/or similarity of accuracy and dependability for the specific reference slice and specific damaged slice.

In a second embodiment, the N1 slice information or the slice information of another specific slice may be the only image slice used as a reference slice for the contour lines of most, if not all, of the damaged slices. In other words, the N1 image slice information may be the only reference side information used (i.e., to the exclusion of, for example, the N3 image slice information) in the restoration of the contour lines of most, if not each, damaged side image slice (i.e., the N1 image slice information is applied to the contour lines of the N2 and N4 image slices and the N3 image slice information is not used). In such an embodiment, the appropriate single reference image slice may be identified via manual identification or automatic identification via, for example, an algorithm. The identification may be according to certain criteria, such as, for example, which reference image slice is most likely to contain the most accurate and dependable reference information.

While the second embodiment is discussed with respect to information from a single reference image being applied to the contour lines of most, if not all, damaged side image slices, in other embodiments, the reference information applied to the contour lines of the damaged image slices may be from more than one image slice. For example, information from two or more reference image slices (e.g., N1 image slice and N3 image slice) are applied individually to the contour lines of the various damage image slices. In one embodiment, the information from the two or more reference image slices may be combined (e.g., averaged) and the combined information then applied to the contour lines of individual damaged image slices.

In some embodiments, the reference side data or information may include a distal tangent line DTL and a posterior tangent line PTL. The distal tangent line DTL may tangentially intersect the extreme distal point of the reference image slice and be parallel to the major axis of the reference image slice ellipse. For example, with respect to the N1 image slice serving as a reference side image slice, the distal tangent line DTL may tangentially intersect the extreme distal point $D_1$ of the reference N1 image slice and be parallel to the major axis $P_1'P_1'$ of the reference N1 image slice ellipse 305-N1.

The posterior tangent line PTL may tangentially intersect the extreme posterior point of the reference image slice and be parallel to the major axis of the reference image slice ellipse. For example, with respect to the N1 image slice serving as a reference side image slice, the posterior tangent line PTL may tangentially intersect the extreme posterior point $P_1$ of the reference N1 image slice and be parallel to the minor axis $D_1DD_1$ of the reference N1 image slice ellipse 305-N1.

As can be understood from FIGS. 3F-3I, most, if not all, femur condlyle image slices N1, N2, N3, N4 will have an origin $O_1$, $O_2$, $O_3$, $O_4$ associated with the ellipse 305 used to describe or define the condyle surfaces of each slice N1, N2, N3, N4. When these image slices are combined together to form the 3D computer generated bone models 22, the various origins $O_1$, $O_2$, $O_3$, $O_4$ will generally align to form a femur axis $AO_F$ extending medial-lateral through the femur bone model 22A as depicted in FIG. 5A. This axis $AO_F$ can be used to properly orient reference side data (e.g., the ellipse 305-N1 and vector $U_1$ of the N1 slice in the current example) when being superimposed onto a damaged side image slice (e.g., the N2 image slice in the current example). The orientation of the data or information of the reference side does not change as the data or information is being superimposed or otherwise applied to the damaged side image slice. For example, the orientation of the ellipse 305-N1 and vector $U_1$ of the N1 slice is maintained or held constant during the superimposing of such reference information onto the N2 slice such that the reference information does not change with respect to orientation or spatial ratios relative to the femur axis $AO_F$ when being superimposed on or otherwise applied to the N2 slice. Thus, as described in greater detail below, since the reference side information is indexed to the damaged side image slice via the axis $AO_F$ and the orientation of the reference side information does not change in the process of being applied to the damaged side image slice, the reference side information can simply be adjusted with respect to size, if needed and as described below with reference to FIGS. 5C2 and 5C3, to assist in the restoration of the damaged side image slice.

While the reference side information may be positionally indexed relative to the damaged side image slices via the femur reference axis $AO_F$ when being applied to the damaged side image slices, other axes may be used for indexing besides an AO axis that runs through or near the origins of the respective image slice ellipses. For example, a reference axis similar to the femur reference axis $AO_F$ and running medial-lateral may pass through other portions of the femur bone model 22A or outside the femur bone model 22A and may be used to positionally index the reference side information to the respective damaged side image slices.

The contour line $N_2$ of the N2 image slice, as with any contour line of any femur or tibia image slice, may be generated via an open or closed loop computer analysis of the cortical bone of the medial condyle 302 in the N2 image slice, thereby outlining the cortical bone with an open or closed loop contour line $N_2$. Where the contour lines are closed loop, the resulting 3D models 22, 28 will be 3D volumetric models. Where the contour lines are open loop, the resulting 3D models 22, 28 will be 3D surface models.

Figure 5D:
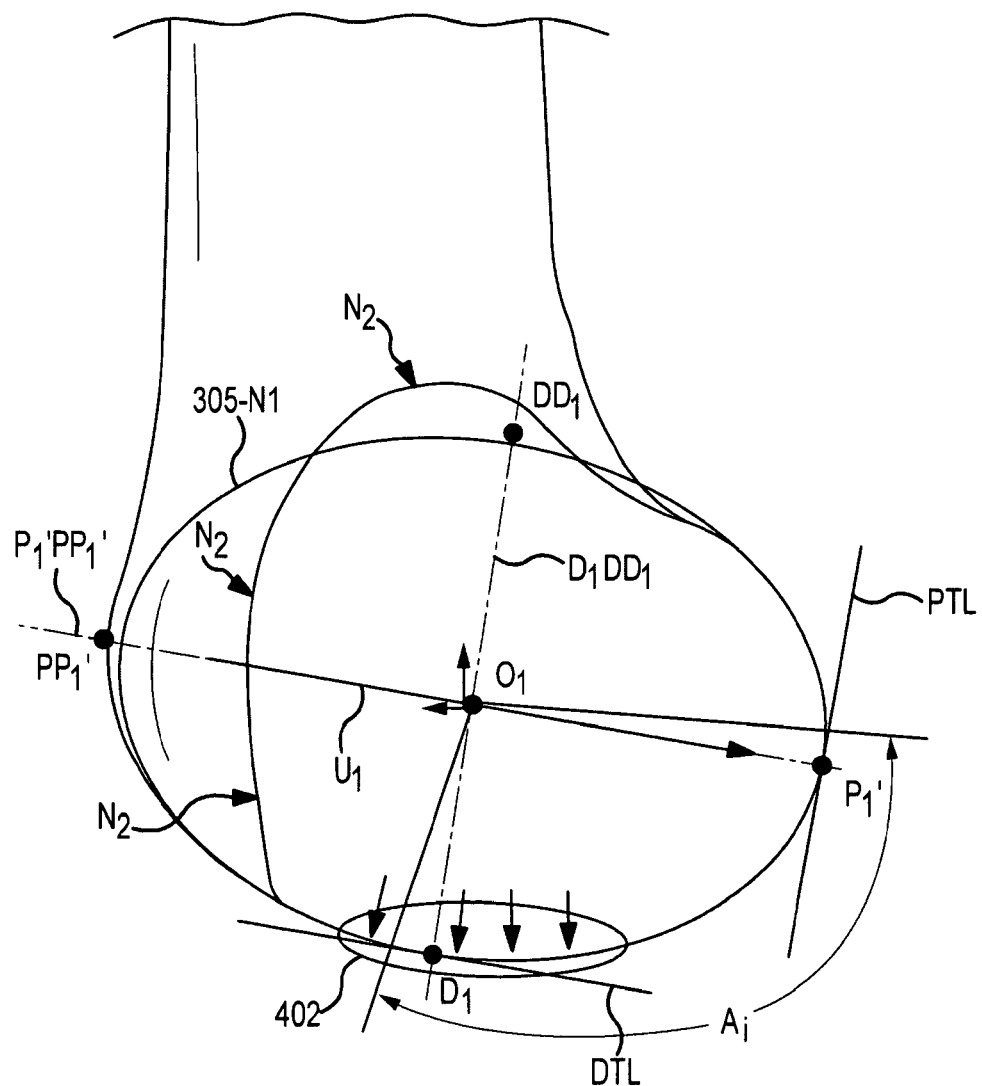
FIG. 5D is the N2 image slice of FIG. 5C1 subsequent to restoration.

While in some cases the reference information from a reference image slice may be substantially similar in characteristics (e.g., size and/or ratios) to the damaged image slice contour line to be simply applied to the contour line, in many cases, the reference information may need to be adjusted with respect to size and/or ratio prior to using the reference information to restore the damaged side contour line as discussed herein with respect to FIGS. 5C1 and 5D. For example, as indicated in FIG. 5C2, which is the same view as FIG. 5C1, except illustrating the reference information is too small relative to the damaged side contour line, the reference information should be increased prior to being used to restore the damaged side contour line. In other words, the N1 information (e.g., the N1 ellipse, vector and tangent lines PTL, DTL), when applied to the contour line of the N2 image slice based on the AO axis discussed above, is too small for at least some of the reference information to match up with at least some of the damaged contour line at the most distal or posterior positions. Accordingly, as can be understood from a comparison of FIGS. 5C1 and 5C2, the N1 information may be increased in size as needed, but maintaining its ratios (e.g., the ratio of the major/minor ellipse axes to each other and the ratios of the offsets of the PTL, DTL from the origin or AO axis), until the N1 information begins to match a boundary of the contour line of the N2 image slice. For example, as depicted in FIG. 5C2, the N1 ellipse is superimposed over the N2 image slice and positionally coordinated with the N2 image slice via the AO axis. The N1 ellipse is smaller than needed to match the contour line of the N2 image slice and is expanded in size until a portion (e.g., the PTL and $P_1'$ of the N1 ellipse) matches a portion (e.g., the most posterior point) of the elliptical contour line of the N2 image slice. A similar process can also be applied to the PTL and DTL, maintaining the ratio of the PTL and DTL relative to the AO axis. As illustrated in FIG. 5C1, the N1 information now corresponds to at least a portion of the damaged image side contour line and can now be used to restore the contour line as discussed below with respect to FIG. 5D.

as indicated in FIG. 5C3, which is the same view as FIG. 5C1, except illustrating the reference information is too large relative to the damaged side contour line, the reference information should be decreased prior to being used to restore the damaged side contour line. In other words, the N1 information (e.g., the N1 ellipse, vector and tangent lines PTL, DTL), when applied to the contour line of the N2 image slice based on the AO axis discussed above, is too large for at least some of the reference information to match up with at least some of the damaged contour line at the most distal or posterior positions. Accordingly, as can be understood from a comparison of FIGS. 5C1 and 5C3, the N1 information may be decreased in size as needed, but maintaining its ratios (e.g., the ratio of the major/minor ellipse axes to each other and the ratios of the offsets of the PTL, DTL from the origin or AO axis), until the N1 information begins to match a boundary of the contour line of the N2 image slice. For example, as depicted in FIG. 5C3, the N1 ellipse is superimposed over the N2 image slice and positionally coordinated with the N2 image slice via the AO axis. The N1 ellipse is larger than needed to match the contour line of the N2 image slice and is reduced in size until a portion (e.g., the PTL and $P_1'$ of the N1 ellipse) matches a portion (e.g., the most posterior point) of the elliptical contour line of the N2 image slice. A similar process can also be applied to the PTL and DTL, maintaining the ratio of the PTL and DTL relative to the AO axis. As illustrated in FIG. 5C1, the N1 information now corresponds to at least a portion of the damaged image side contour line and can now be used to restore the contour line as discussed below with respect to FIG. 5D.

As can be understood from FIG. 5D, which is the N2 image slice of FIG. 5C1 subsequent to restoration, the contour line $N_2$ of the N2 image slice has been extended out to the boundaries of the ellipse 305-N1 in the restored region 402 ([block 220] of FIG. 2). This process of applying information (e.g., ellipses 305 and vectors) from the reference side to the damaged side is repeated slice-by-slice for most, if not all, image slices 16 forming the damaged side of the femur bone model 22A. Once most or all of the image slices 16 of the damaged side have been restored, the image slices used to form the femur bone model 22A, including the recently restored images slices, are recompiled via 3D computer modeling programs into a 3D femur restored bone model 28A similar to that depicted in FIG. 3A ([block 225] of FIG. 2).

As can be understood from FIGS. 5C1 and 5D, in one embodiment, the damaged contour line $N_2$ of the N2 image slice is adjusted based on the ratio of the reference side major axis major axis $P_1'PP_1'$ to the reference side minor axis $D_1DD_1$. In one embodiment, the damaged contour line $N_2$ of the N2 image slice is adjusted based on reference side ellipse 305-N1. Therefore, the damaged contour lines of the damaged side image slices can be assessed to be enlarged according to the ratios pertaining to the ellipses of the reference side image slices.

Depending on the relationship of the joint contour lines of the damaged side image slice relative to the ratios obtained from the reference side information or data, the joint contour lines of the damaged side image slice may be manipulated so the joint contour line is increased along its major axis and/or its minor axis. Depending on the patient's knee shape, the major axis and minor axis of the condyle ellipse varies from person to person. If the major axis is close to the minor axis in the undamaged condyle, then the curvature of the undamaged condyle is close to a round shape. In such configured condyles, in the restoration procedure, the contour of the damaged condyle can be assessed and increased in a constant radius in both the major and minor axis. For condyles of other configurations, such as where the undamaged condyle shows an ellipse contour with a significantly longer major axis as compared to its minor axis, the bone restoration may increase the major axis length in order to modify the damaged condyle contour.

A damaged side tibia plateau can also be restored by applying data or information from the reference side femur condyle to the damaged side tibia plateau. In this continued example, the damaged side tibia plateau will be the medial tibia plateau 306, and the reference side femur condyle will be the lateral femur condyle 300. In one embodiment, the process of restoring the damaged side tibia plateau 306 begins by analyzing the damaged side tibia plateau 306 to determine at least one of a highest anterior point or a highest posterior point of the damaged side tibia plateau 306.

In one embodiment, as can be understood from FIG. 4C as viewed along the N4 image slice and assuming the damage to the medial tibia plateau 306 is not so extensive that at least one of the highest anterior or posterior points Q4, Q4' still exists, the damaged tibia plateau 306 can be analyzed via tangent lines to identify the surviving high point Q4, Q4'. For example, if the damage to the medial tibia plateau 306 was concentrated in the posterior region such that the posterior highest point Q4' no longer existed, the tangent line $T_{Q4}$ could be used to identify the anterior highest point Q4. Similarly, if the damage to the medial tibia plateau 306 was concentrated in the anterior region such that the anterior highest point Q4 no longer existed, the tangent line $T_{Q4'}$, could be used to identify the posterior highest point Q4'. In some embodiments, a vector extending between the highest points Q4, Q4' may be generally perpendicular to the tangent lines $T_{Q4}$, $T_{Q4'}$.

Figure 5E:
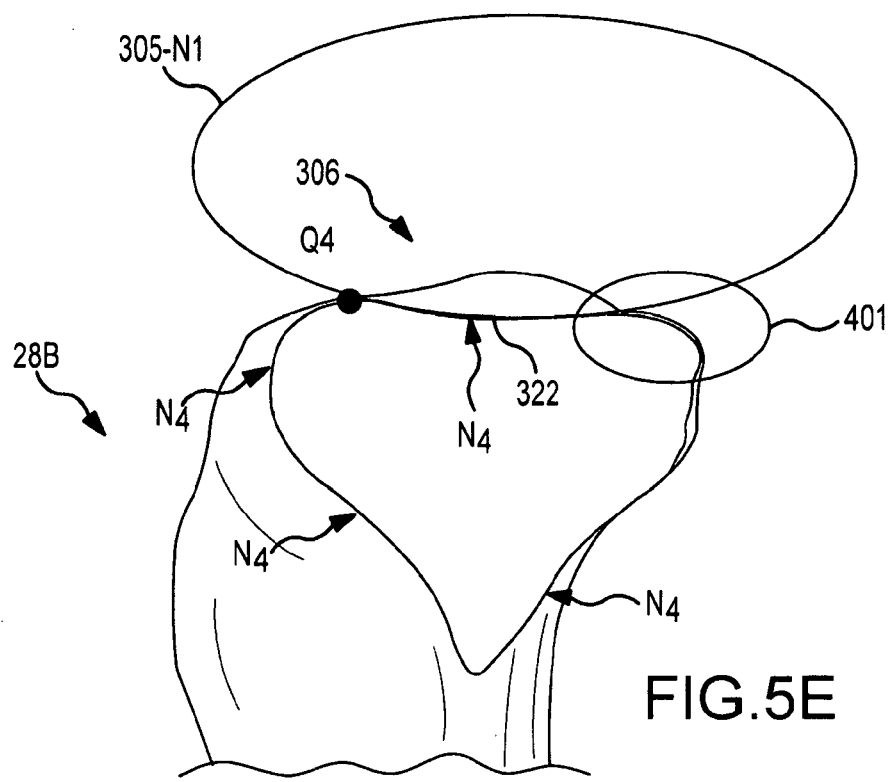
FIG. 5E is a sagital view of the medial tibia plateau along the N4 image slice, wherein damage to the plateau is mainly in the posterior region.

In another embodiment, the reference side femur condyle ellipse 305-N1 can be applied to the damaged medial tibia plateau 306 to determine at least one of the highest anterior or posterior points Q4, Q4' along the N4 image slice. This process may be performed assuming the damage to the medial tibia plateau 306 is not so extensive that at least one of the highest anterior or posterior points Q4, Q4' still exists. For example, as illustrated by FIG. 5E, which is a sagital view of the medial tibia plateau 306 along the N4 image slice, wherein damage 401 to the plateau 306 is mainly in the posterior region, the reference side femur condyle ellipse 305-N1 can be applied to the damaged medial tibia plateau 306 to identify the anterior highest point Q4 of the tibia plateau 306. Similarly, in another example, as illustrated by FIG. 5F, which is a sagital view of the medial tibia plateau 306 along the N4 image slice, wherein damage 401 to the plateau 306 is mainly in the anterior region, the reference side femur condyle ellipse 305-N1 can be applied to the damaged medial tibia plateau 306 to identify the posterior highest point Q4' of the tibia plateau 306.

In one embodiment in a manner similar to that discussed above with respect to FIGS. 5C2 and 5C3, the reference information (e.g., N1 information such as the N1 ellipse) may be applied to the damaged contour line via the AO axis and adjusted in size (e.g., made smaller or larger) until the N1 ellipse matches a portion of the damaged contour line in order to find the highest point, which may be, for example, Q4 or Q4'. As explained above with respect to FIGS. 5C2 and 5C3, the adjustments in size for reference information may be made while maintaining the ratio of the N1 information.

Figure 5F:
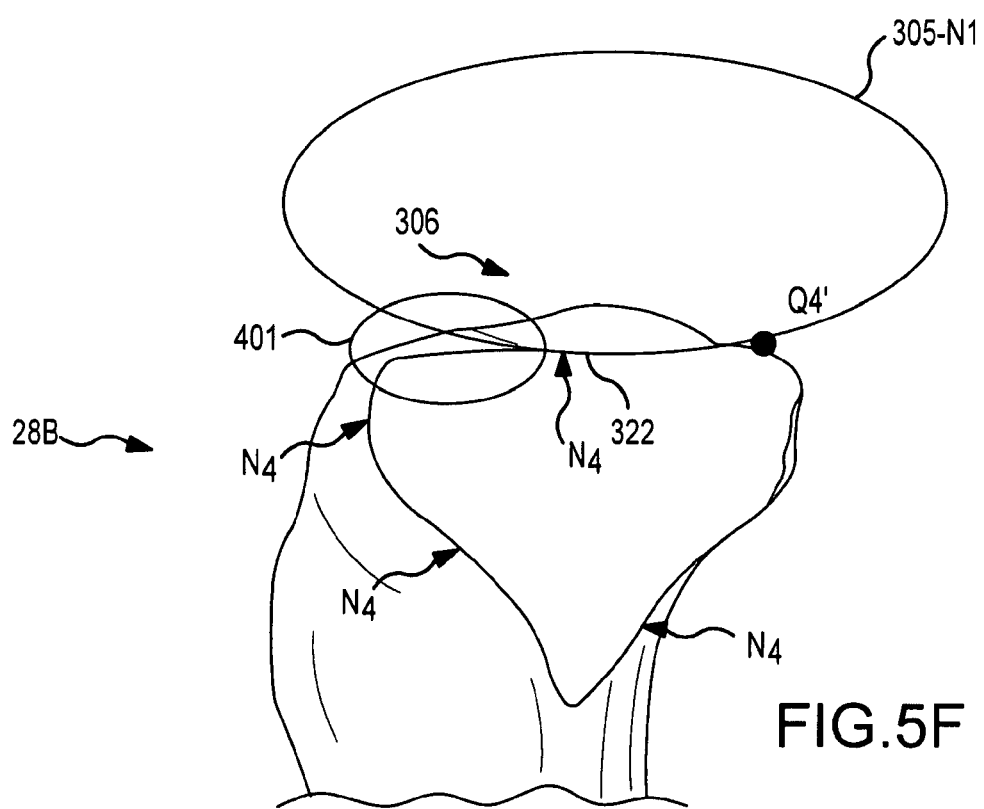
FIG. 5F is a sagital view of the medial tibia plateau along the N4 image slice, wherein damage to the plateau is mainly in the anterior region.
Figure 5G:
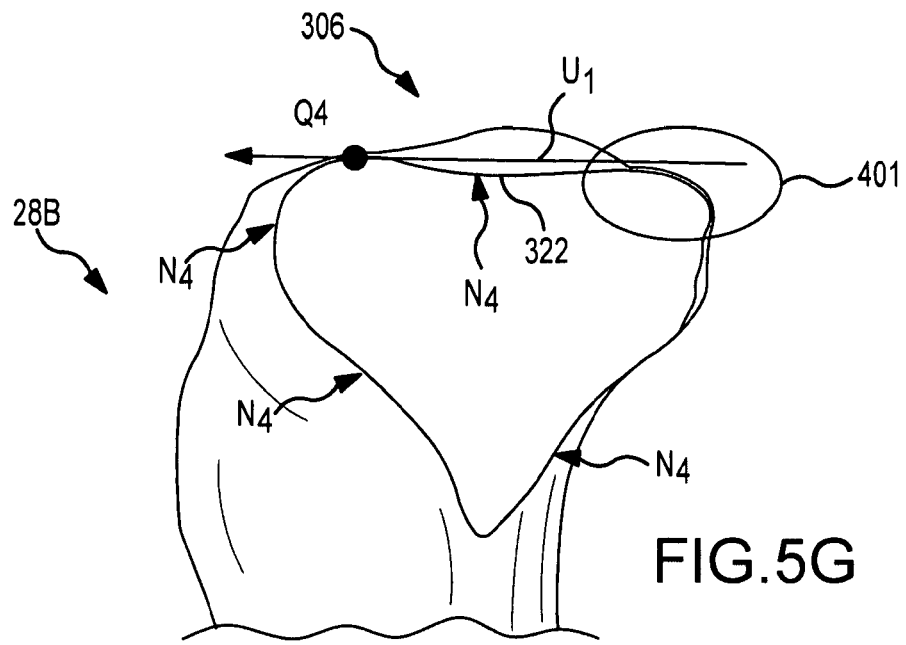
FIG. 5G is the same view as FIG. 5E, except showing the reference side femur condyle vector extending through the anterior highest point of the tibia plateau.
Figure 5H:
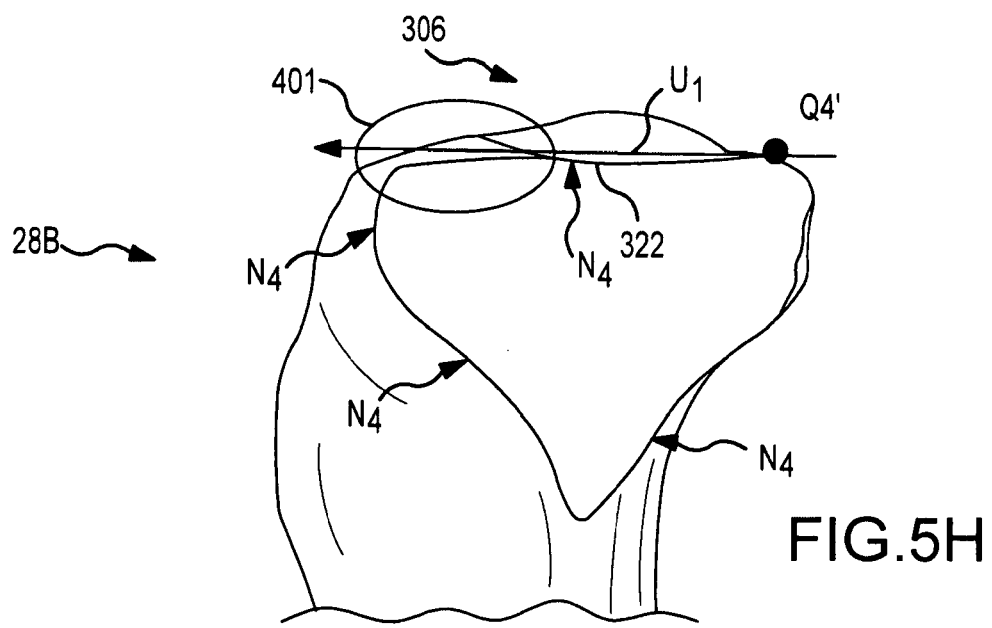
FIG. 5H is the same view as FIG. 5F, except showing the reference side femur condyle vector extending through the posterior highest point of the tibia plateau.

Once the highest point is determined through any of the above-described methods discussed with respect to FIGS. 4C, 5E and 5F, the reference side femur condyle vector can be applied to the damaged side tibia plateau to determine the extent to which the tibia plateau contour line 322 needs to be restored ([block 215] of FIG. 2). For example, as illustrated by FIGS. 5G and 5H, which are respectively the same views as FIGS. 5E and 5F, the vector from the reference side lateral femur condyle 300 (e.g., the vector $U_1$ from the N1 image slice) is applied to the damaged side medial tibia plateau 306 such that the vector $U_1$ intersects the existing highest point. Thus, as shown in FIG. 5G, where the existing highest point is the anterior point Q4, the vector $U_1$ will extend through the anterior point Q4 and will spaced apart from damage 401 in the posterior region of the tibia plateau contour line 322 by the distance the posterior region of the tibia plateau contour line 322 needs to be restored. Similarly, as shown in FIG. 5H, where the existing highest point is the posterior point Q4', the vector $U_1$ will extend through the posterior point Q4' and will spaced apart from the damage 401 of the anterior region of the tibia plateau contour line 322 by the distance the anterior region of the tibia plateau contour line 322 needs to be restored.

Figure 5I:
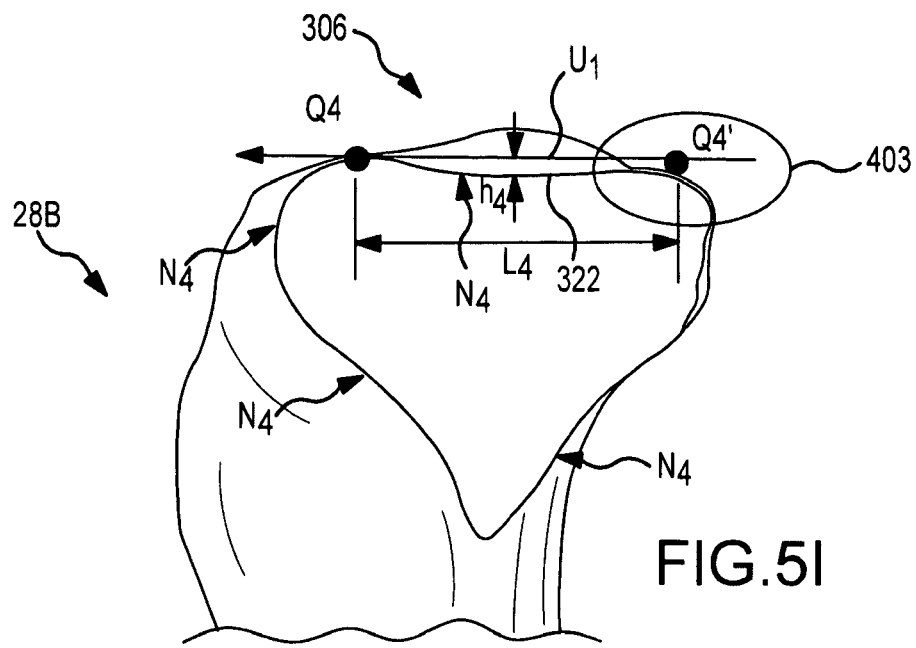
FIG. 5I is the same view as FIG. 5G, except showing the anterior highest point of the tibia plateau restored.
Figure 5J:
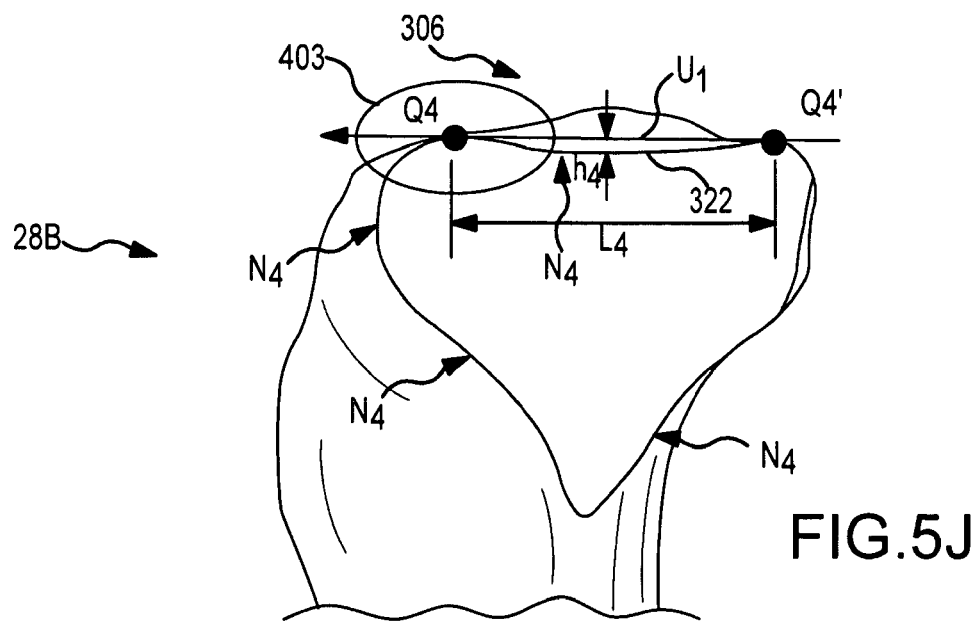
FIG. 5J is the same view as FIG. 5H, except showing the posterior highest point of the tibia plateau restored.

As shown in FIGS. 5I and 5J, which are respectively the same views as FIGS. 5G and 5H, the damaged region 401 of the of the tibia plateau contour line 322 is extended up to intersect the reference vector $U_1$, thereby restoring the missing posterior high point Q4' in the case of FIG. 5I and the anterior high point Q4 in the case of and FIG. 5J, the restoring resulting in restored regions 403. As can be understood from FIGS. 5E, 5F, 5I and 5J, in one embodiment, the reference side femur condyle ellipse 305-N1 may be applied to the damaged side tibia plateau 306 to serve as a guide to locate the proper offset distance $L_4$ between the existing high point (i.e., Q4 in FIG. 5I and Q4' in FIG. 5J) and the newly restored high point (i.e., Q4' in FIG. 5I and Q4 in FIG. 5J) of the restored region 403. Also, in one embodiment, the reference side femur condyle ellipse 305-N1 may be applied to the damaged side tibia plateau 306 to serve as a guide to achieve the proper curvature for the tibia plateau contour line 322. The curvature of the tibia plateau contour line 322 may such that the contour line 322 near the midpoint between the anterior and posterior high points Q4, Q4' is offset from the reference vector $U_1$ by a distance $h_4$. In some embodiments, the ratio of the distances $h_4/L_4$ after the restoration is less than approximately 0.01. As discussed above, the reference ellipse may be applied to the damaged contour line and adjusted in size, but maintaining the ratio, until the ellipse matches a portion of the damaged contour line.

As discussed above with respect to the femur condyle image slices being positionally referenced to each other via a femur reference axis $AO_F$, and as can be understood from FIG. 5B, each tibia image slice N1, N2, N3, N4 will be generated relative to a tibia reference axis $AO_T$, which may be the same as or different from the femur reference axis $AO_F$. The tibia reference axis $AO_T$ will extend medial-lateral and may pass through a center point of each area defined by the contour line of each tibia image slice N1, N2, N3, N4. The tibia reference axis $AO_T$ may extend through other regions of the tibia image slices N1, N2, N3, N4 or may extend outside of the tibia image slices, even, for example, through the origins $O_1$, $O_2$, $O_3$, $O_4$ of the respective femur images slices N1, N2, N3, N4 (in such a case the tibia reference axis $AO_F$ and femur reference axis $AO_F$ may be the same or share the same location).

The axis $AO_T$ can be used to properly orient reference side data (e.g., the ellipse 305-N1 and vector $U_1$ of the N1 slice in the current example) when being superimposed onto a damaged side image slice (e.g., the N4 image slice in the current example). The orientation of the data or information of the reference side does not change as the data or information is being superimposed or otherwise applied to the damaged side image slice. For example, the orientation of the ellipse 305-N1 and vector $U_1$ of the N1 slice is maintained or held constant during the superimposing of such reference information onto the N4 slice such that the reference information does not change when being superimposed on or otherwise applied to the N4 slice. Thus, since the reference side information is indexed to the damaged side image slice via the axis $AO_T$ and the orientation of the reference side information does not change in the process of being applied to the damaged side image slice, the reference side information can simply be adjusted with respect to size to assist in the restoration of the damaged side image slice.

The contour line $N_4$ of the N4 image slice, as with any contour line of any femur or tibia image slice, may be generated via an open or closed loop computer analysis of the cortical bone of the medial tibia plateau 306 in the N4 image slice, thereby outlining the cortical bone with an open or closed loop contour line $N_4$. Where the contour lines are closed loop, the resulting 3D models 22, 28 will be 3D volumetric models. Where the contour lines are open loop, the resulting 3D models 22, 28 will be 3D surface models.

The preceding example discussed with respect to FIGS. 5A-5J is given in the context of the lateral femur condyle 300 serving as the reference side and the medial femur condyle 302 and medial tibia condyle 306 being the damaged sides. Specifically, reference data or information (e.g., ellipses, vectors, etc.) from lateral femur condyle 300 is applied to the medial femur condyle 302 and medial tibia plateau 306 for the restoration thereof. The restoration process for the contour lines of the damaged side femur condyle 302 and damaged side tibia plateau 306 take place slice-by-slice for the image slices 16 forming the damaged side of the bone models 22A, 22B ([block 220] of FIG. 2). The restored image slices 16 are then utilized when a 3D computer modeling program recompiles the image slices 16 to generate the restored bone models 28A, 28B ([block 225] of FIG. 2).

While a specific example is not given to illustrate the reversed situation, wherein the medial femur condyle 302 serves as the reference side and the lateral femur condyle 300 and lateral tibia condyle 304 are the damaged sides, the methodology is the same as discussed with respect to FIGS. 5A-5J and need not be discussed in such great detail. It is sufficient to know that reference data or information (e.g., ellipses, vectors, etc.) from the medial femur condyle 302 is applied to the lateral femur condyle 300 and lateral tibia plateau 304 for the restoration thereof, and the process is the same as discussed with respect to FIGS. 5A-5J.

2. Employing Vectors From a Tibia Plateau of a Reference Side of a Knee Joint to Restore the Tibia Plateau of the Damaged Side A damaged side tibia plateau can also be restored by applying data or information from the reference side tibia plateau to the damaged side tibia plateau. In this example, the damaged side tibia plateau will be the medial tibia plateau 306, and the reference side tibia plateau will be the lateral tibia plateau 304.

In one embodiment, the process of restoring the damaged side tibia plateau 306 begins by analyzing the reference side tibia plateau 304 to determine the highest anterior point and a highest posterior point of the reference side tibia plateau 304. Theses highest points can then be used to determine the reference vector.

In one embodiment, as can be understood from FIG. 4C as viewed along the N3 image slice, the reference side tibia plateau 304 can be analyzed via tangent lines to identify the highest points Q3, Q3'. For example, tangent line $T_{Q3}$ can be used to identify the anterior highest point Q3, and tangent line $T_{Q3'}$ can be used to identify the posterior highest point Q3'. In some embodiments, a vector extending between the highest points Q3, Q3' may be generally perpendicular to the tangent lines $T_{Q3}$, $T_{Q3'}$.

In another embodiment, the reference side femur condyle ellipse 305-N1 can be applied to the reference side lateral tibia plateau 304 to determine the highest anterior or posterior points Q3, Q3' along the N3 image slice. For example, as can be understood from FIG. 4A, the reference side femur condyle ellipse 305-N1 (or ellipse 305-N3 if analyzed in the N3 image slice) can be applied to the reference side lateral tibia plateau 304 to identify the anterior highest point Q1 of the tibia plateau 304, and the reference side femur condyle ellipse 305-N1 (or ellipse 305-N3 if analyzed in the N3 image slice) can be applied to the reference side lateral tibia plateau 304 to identify the posterior highest point Q1' of the tibia plateau 306. Where the ellipse 305-N3 of the N3 image slice is utilized, the highest tibia plateau points may be Q3, Q3'.

As can be understood from FIG. 4A, once the highest points are determined, a reference vector can be determined by extending a vector through the points. For example, vector $V_1$ can be found by extending the vector through highest tibia plateau points Q1, Q1' in the N1 slice.

In one embodiment, the process of restoring the damaged side tibia plateau 306 continues by analyzing the damaged side tibia plateau 306 to determine at least one of a highest anterior point or a highest posterior point of the damaged side tibia plateau 306.

In one embodiment, as can be understood from FIG. 4C as viewed along the N4 image slice and assuming the damage to the medial tibia plateau 306 is not so extensive that at least one of the highest anterior or posterior points Q4, Q4' still exists, the damaged tibia plateau 306 can be analyzed via tangent lines to identify the surviving high point Q4, Q4'. For example, if the damage to the medial tibia plateau 306 was concentrated in the posterior region such that the posterior highest point Q4' no longer existed, the tangent line $T_{Q4}$ could be used to identify the anterior highest point Q4. Similarly, if the damage to the medial tibia plateau 306 was concentrated in the anterior region such that the anterior highest point Q4 no longer existed, the tangent line $T_{Q4'}$ could be used to identify the posterior highest point Q4'.

In another embodiment, the reference side femur condyle ellipse 305-N1 can be applied to the damaged medial tibia plateau 306 to determine at least one of the highest anterior or posterior points Q4, Q4' along the N4 image slice. This process may be performed assuming the damage to the medial tibia plateau 306 is not so extensive that at least one of the highest anterior or posterior points Q4, Q4' still exists. For example, as illustrated by FIG. 5E, which is a sagital view of the medial tibia plateau 306 along the N4 image slice, wherein damage 401 to the plateau 306 is mainly in the posterior region, the reference side femur condyle ellipse 305-N1 can be applied to the damaged medial tibia plateau 306 to identify the anterior highest point Q4 of the tibia plateau 306. Similarly, in another example, as illustrated by FIG. 5F, which is a sagital view of the medial tibia plateau 306 along the N4 image slice, wherein damage 401 to the plateau 306 is mainly in the anterior region, the reference side femur condyle ellipse 305-N1 can be applied to the damaged medial tibia plateau 306 to identify the posterior highest point Q4' of the tibia plateau 306.

In one embodiment in a manner similar to that discussed above with respect to FIGS. 5C2 and 5C3, the reference information (e.g., N1 information such as the N1 ellipse) may be applied to the damaged contour line via the AO axis and adjusted in size (e.g., made smaller or larger) until the N1 ellipse matches a portion of the damaged contour line in order to find the highest point, which may be, for example, Q4 or Q4'. As explained above with respect to FIGS. 5C2 and 5C3, the adjustments in size for reference information may be made while maintaining the ratio of the N1 information.

Figure 5K:
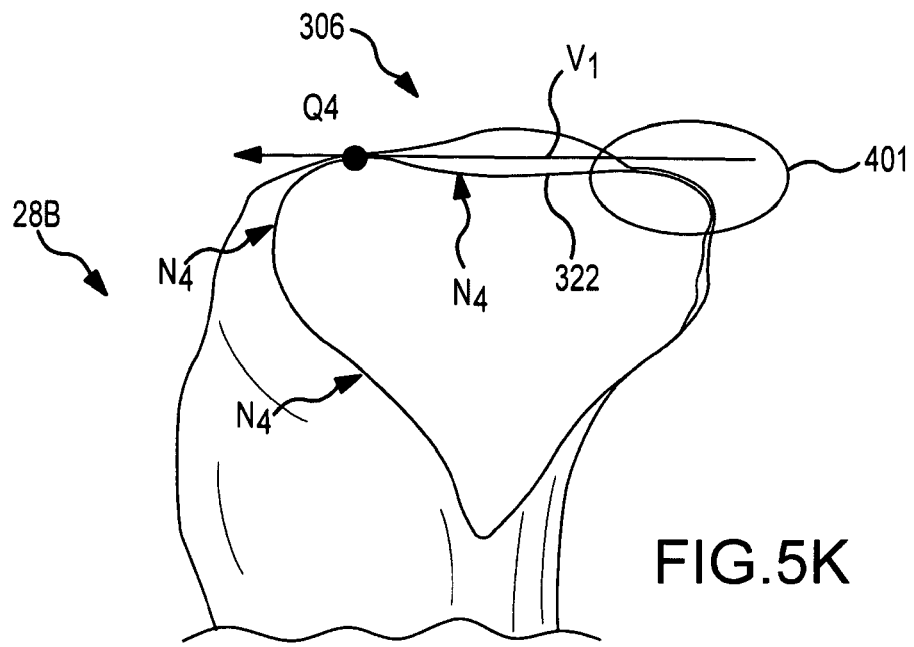
FIG. 5K is the same view as FIG. 5G, except employing reference vector $V_1$ as opposed to $U_1$.
Figure 5L:
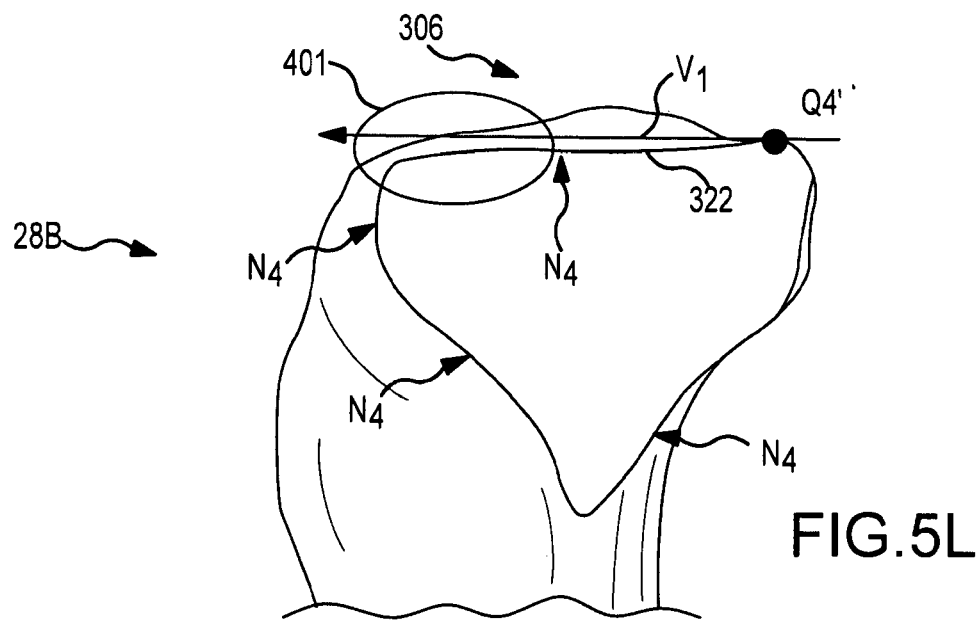
FIG. 5L is the same view as FIG. 5H, except employing reference vector $V_1$ as opposed to $U_1$.

Once the highest point is determined through any of the above-described methods discussed with respect to FIGS. 4C, 5E and 5F, the reference side tibia plateau vector can be applied to the damaged side tibia plateau to determine the extent to which the tibia plateau contour line 322 needs to be restored ([block 215] of FIG. 2). For example, as can be understood from FIGS. 5K and 5L, which are respectively the same views as FIGS. 5G and 5H, the vector from the reference side lateral tibia plateau 304 (e.g., the vector $V_1$ from the N1 image slice) is applied to the damaged side medial tibia plateau 306 such that the vector $V_1$ intersects the existing highest point. Thus, as shown in FIG. 5K, where the existing highest point is the anterior point Q4, the vector $V_1$ will extend through the anterior point Q4 and will spaced apart from damage 401 in the posterior region of the tibia plateau contour line 322 by the distance the posterior region of the tibia plateau contour line 322 needs to be restored. Similarly, as shown in FIG. 5L, where the existing highest point is the posterior point Q4', the vector $V_1$ will extend through the posterior point Q4' and will spaced apart from the damage 401 of the anterior region of the tibia plateau contour line 322 by the distance the anterior region of the tibia plateau contour line 322 needs to be restored.

Figure 5M:
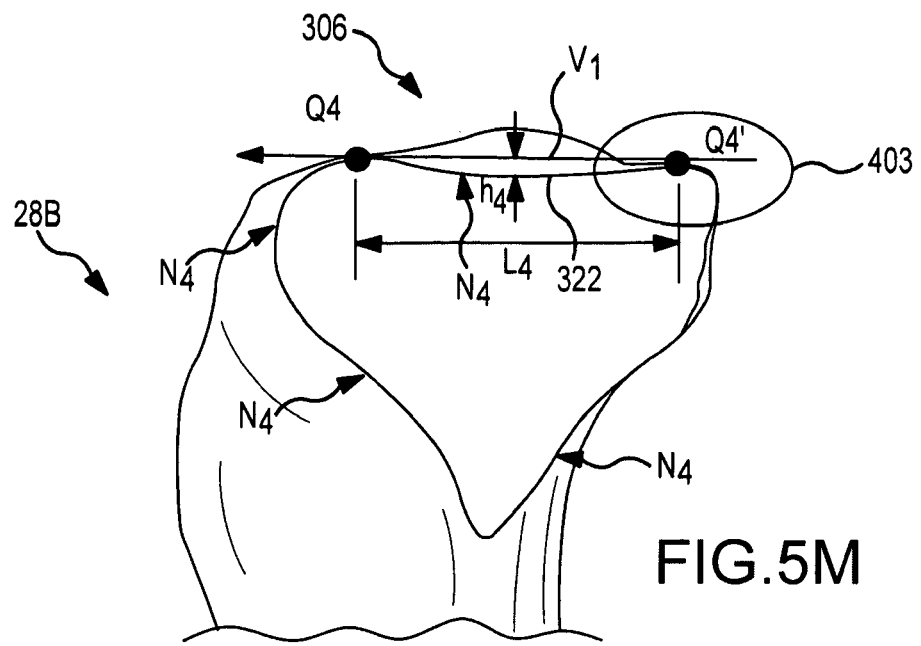
FIG. 5M is the same view as FIG. 5I, except employing reference vector $V_1$ as opposed to $U_1$.
Figure 5N:
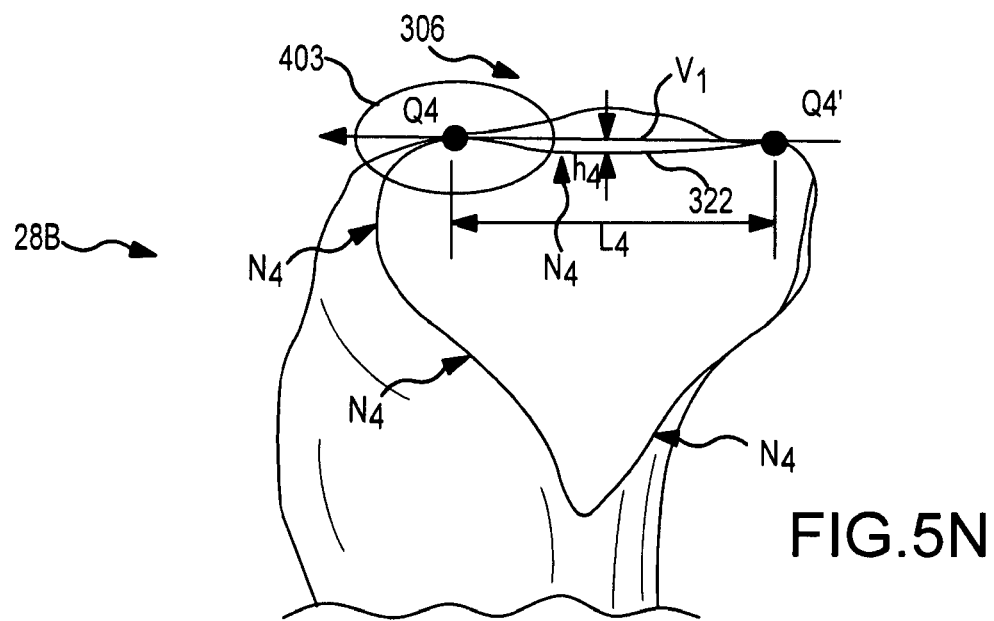
FIG. 5N is the same view as FIG. 5J, except employing reference vector $V_1$ as opposed to $U_1$.

As shown in FIGS. 5M and 5N, which are respectively the same views as FIGS. 5I and 5J, the damaged region 401 of the of the tibia plateau contour line 322 is extended up to intersect the reference vector $V_1$, thereby restoring the missing posterior high point Q4' in the case of FIG. 5M and the anterior high point Q4 in the case of and FIG. 5N, the restoring resulting in restored regions 403. As can be understood from FIGS. 5E, 5F, 5M and 5N, in one embodiment, the reference side femur condyle ellipse 305-N1 may be applied to the damaged side tibia plateau 306 to serve as a guide to locate the proper offset distance $L_4$ between the existing high point (i.e., Q4 in FIG. 5M and Q4' in FIG. 5N) and the newly restored high point (i.e., Q4' in FIG. 5M and Q4 in FIG. 5N) of the restored region 403. Also, in one embodiment, the reference side femur condyle ellipse 305-N1 may be applied to the damaged side tibia plateau 306 to serve as a guide to achieve the proper curvature for the tibia plateau contour line 322. The curvature of the tibia plateau contour line 322 may such that the contour line 322 near the midpoint between the anterior and posterior high points Q4, Q4' is offset from the reference vector $U_1$ by a distance $h_4$. In some embodiments, the ratio of the distances $h_4/L_4$ after the restoration is less than approximately 0.01. As discussed above, the reference ellipse may be applied to the damaged contour line and adjusted in size, but maintaining the ratio, until the ellipse matches a portion of the damaged contour line.

As discussed above with respect to the femur condyle image slices being positionally referenced to each other via a femur reference axis $AO_F$, and as can be understood from FIG. 5B, each tibia image slice N1, N2, N3, N4 will be generated relative to a tibia reference axis $AO_T$, which may be the same as or different from the femur reference axis $AO_F$. The tibia reference axis $AO_T$ will extend medial-lateral and may pass through a center point of each area defined by the contour line of each tibia image slice N1, N2, N3, N4. The tibia reference axis $AO_T$ may extend through other regions of the tibia image slices N1, N2, N3, N4 or may extend outside of the tibia image slices, even, for example, through the origins $O_1$, $O_2$, $O_3$, $O_4$ of the respective femur images slices N1, N2, N3, N4 (in such a case the tibia reference axis $AO_F$ and femur reference axis $AO_F$ may be the same or share the same location).

The axis $AO_T$ can be used to properly orient reference side data (e.g., the ellipse 305-N1 and vector $V_1$ of the N1 slice in the current example) when being superimposed onto a damaged side image slice (e.g., the N4 image slice in the current example). The orientation of the data or information of the reference side does not change as the data or information is being superimposed or otherwise applied to the damaged side image slice. For example, the orientation of the ellipse 305-N1 and vector $V_1$ of the N1 slice is maintained or held constant during the superimposing of such reference information onto the N4 slice such that the reference information does not change when being superimposed on or otherwise applied to the N4 slice. Thus, since the reference side information is indexed to the damaged side image slice via the axis $AO_T$ and the orientation of the reference side information does not change in the process of being applied to the damaged side image slice, the reference side information can simply be adjusted with respect to size to assist in the restoration of the damaged side image slice.

The contour line $N_4$ of the N4 image slice, as with any contour line of any femur or tibia image slice, may be generated via an open or closed loop computer analysis of the cortical bone of the medial tibia plateau 306 in the N4 image slice, thereby outlining the cortical bone with an open or closed loop contour line $N_4$. Where the contour lines are closed loop, the resulting 3D models 22, 28 will be 3D volumetric models. Where the contour lines are open loop, the resulting 3D models 22, 28 will be 3D surface models.

In the current example discussed with respect to FIGS. 5K-5N, the information from the reference side tibia plateau 304 is employed to restore the damaged side tibia plateau 306. However, the information from the reference side femur condyle 300 is still used to restore the damaged side femur condyle 302 as discussed above in the preceding example with respect to FIGS. 5A-5D.

The preceding example discussed with respect to FIGS. 5K-5N is given in the context of the lateral tibia plateau 304 and lateral femur condyle 300 serving as the reference sides and the medial femur condyle 302 and medial tibia condyle 306 being the damaged sides. Specifically, reference data or information (e.g., vectors from the lateral tibia plateau 304 and ellipses, vectors, etc. from the lateral femur condyle 300) are applied to the medial femur condyle 302 and medial tibia plateau 306 for the restoration thereof. The restoration process for the contour lines of the damaged side femur condyle 302 and damaged side tibia plateau 306 take place slice-by-slice for the image slices 16 forming the damaged side of the bone models 22A, 22B ([block 220] of FIG. 2). The restored image slices 16 are then utilized when a 3D computer modeling program recompiles the image slices 16 to generate the restored bone models 28A, 28B ([block 225] of FIG. 2).

While a specific example is not given to illustrate the reversed situation, wherein the medial tibia plateau 306 and medial femur condyle 302 serve as the reference sides and the lateral femur condyle 300 and lateral tibia condyle 304 are the damaged sides, the methodology is the same as discussed with respect to FIGS. 5A-5D and 5K-5N and need not be discussed in such great detail. It is sufficient to know that reference data or information (e.g., ellipses, vectors, etc.) from the medial tibia plateau 306 and medial femur condyle 302 are applied to the lateral femur condyle 300 and lateral tibia plateau 304 for the restoration thereof, and the process is the same as discussed with respect to FIGS. 5A-5D and 5K-5N.

e. Verifying Accuracy of Restored Bone Model

Once the bone models 22A, 22B are restored into restored bone models 28A, 28B as discussed in the preceding sections, the accuracy of the bone restoration process is checked ([block 230] of FIG. 2). Before discussion example methodology of conducting such accuracy checks, the following discussion regarding the kinetics surround a knee joint is provided.

The morphological shape of the distal femur and its relation to the proximal tibia and the patella suggests the kinetics of the knee (e.g., see Eckhoff et al., "Three-Dimensional Mechanics, Kinetics, and Morphology of the Knee in Virtual Reality", JBJS (2005); 87:71-80). The movements that occur at the knee joint are flexion and extension, with some slight amount of rotation in the bent position. During the movement, the points of contact of the femur with the tibia are constantly changing. Thus, in the flexed position (90° knee extension), the hinder part of the articular surface of the tibia is in contact with the rounded back part of the femoral condyles. In the semiflexed position, the middle parts of the tibia facets articulate with the anterior rounded part of the femoral condyles. In the fully extended position (0° knee extension), the anterior and the middle parts of the tibia facets are in contact with the anterior flattened portion of the femoral condyles.

With respect to the patella, in extreme flexion, the inner articular facet rests on the outer part of the internal condyle of the femur. In flexion, the upper part of facets rest on the lower part of the trochlear surface of the femur. In midflexion, the middle pair rest on the middle of the trochlear surface. However, in extension, the lower pair of facets on the patella rest on the upper portion of the trochlear surface of the femur. The difference may be described as the shifting of the points of contact of the articulate surface.

The traditional knee replacement studies focus mainly around the tibial-femoral joint. The methods disclosed herein employ the patella in a tri-compartmental joint study by locating the patella groove of the knee. The posterior surface of patella presents a smooth oval articular area divided into two facets by a vertical ridge, the facets forming the medial and lateral parts of the same surface.

The vertical ridge of the posterior patella corresponds to the femoral trochlear groove. In the knee flexion/extension motion movement, the patella normally moves up and down in the femoral trochlear grove along the vertical ridge and generates quadriceps forces on the tibia. The patellofemoral joint and the movement of the femoral condyles play a major role in the primary structure/mechanics across the joint. When the knee is moving and not fully extended, the femoral condyle surfaces bear very high load or forces. In a normal knee, the patella vertical ridge is properly aligned along the femoral trochlear groove so this alignment provides easy force generation in the sliding movement. If the patella is not properly aligned along the trochlear groove or tilted in certain angles, then it is hard to initiate the sliding movement so it causes difficulty with respect to walking. Further, the misaligned axis along the trochlear groove can cause dislocation of the patella on the trochlear groove, and uneven load damage on the patella as well.

The methods disclosed herein for the verification of the accuracy of the bone restoration process employ a "trochlear groove axis" or the "trochlear groove reference plane" as discussed below. This axis or reference plane extend across the lowest extremity of trochlear groove in both the fully-extended and 90° extension of the knee. Moreover, in relation to the joint line, the trochlear groove axis is perpendicular or generally perpendicular to the joint line of the knee.

Because the vertical ridge of the posterior patella is generally straight (vertical) in the sliding motion, the corresponding trochlear groove axis should be straight as well. The trochlear groove axis is applied into the theory that the joint line of the knee is parallel to the ground. In a properly aligned knee or normal knee, the trochlear groove axis is presumed to be perpendicular or nearly perpendicular to the joint line.

For the OA, rarely is there bone damage in the trochlear groove, typically only cartilage damage. Thus, the femoral trochlear groove can serve as a reliable bone axis reference for the verification of the accuracy of the bone restoration when restoring a bone model 22 into a restored bone model 28.

Figure 6A:
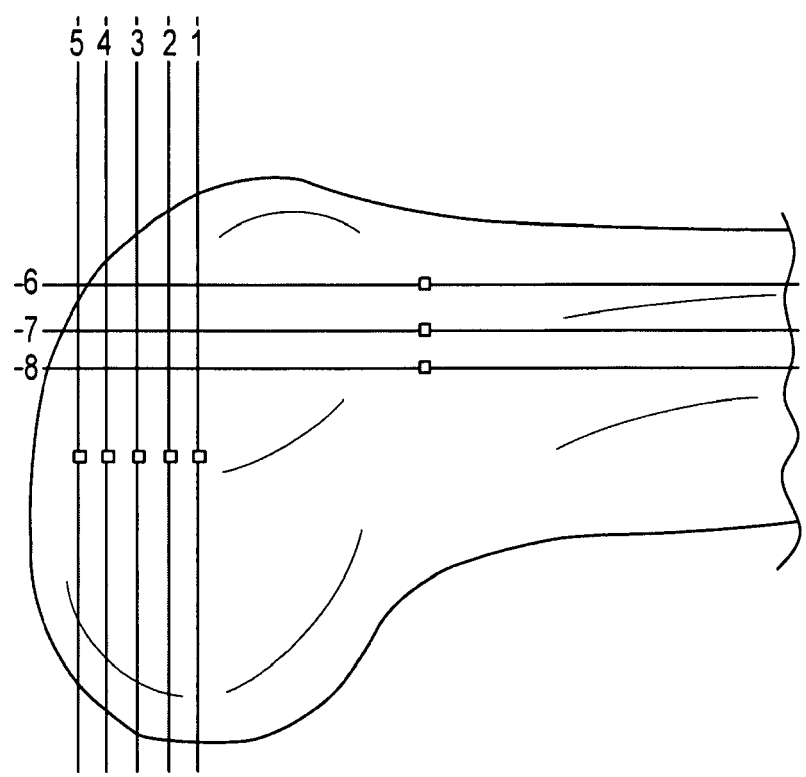
FIG. 6A is a sagital view of a femur restored bone model illustrating the orders and orientations of imaging slices (e.g., MRI slices, CT slices, etc.) forming the femur restored bone model.
Figure 6D:
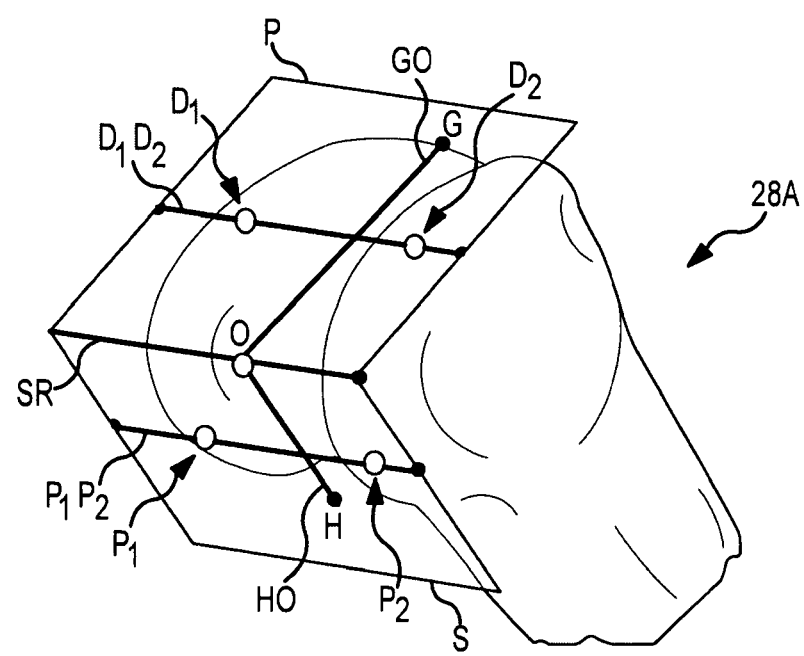
FIG. 6D is a perspective view of the distal end of the femur restored bone model.

For a detailed discussion of the methods for verifying the accuracy of the bone restoration process, reference is made to FIGS. 6A-6D. FIG. 6A is a sagital view of a femur restored bone model 28A illustrating the orders and orientations of imaging slices 16 (e.g., MRI slices, CT slices, etc.) forming the femur restored bone model 28A. FIG. 6B is the distal images slices 1-5 taken along section lines 1-5 of the femur restored bone model 28A in FIG. 6A. FIG. 6C is the coronal images slices 6-8 taken along section lines 6-8 of the femur restored bone model 28A in FIG. 6A. FIG. 6D is a perspective view of the distal end of the femur restored bone model 28A.

As shown in FIG. 6A, a multitude of image slices are compiled into the femur restored bone model 28A from the image slices originally forming the femur bone model 22A and those restored image slices modified via the above-described methods. Image slices may extend medial-lateral in planes that would be normal to the longitudinal axis of the femur, such as image slices 1-5. Image slices may extend medial-lateral in planes that would be parallel to the longitudinal axis of the femur, such as image slices 6-8. The number of image slices may vary from 1-50 and may be spaced apart in a 2 mm spacing.

As shown in FIG. 6B, each of the slices 1-5 can be aligned vertically along the trochlear groove, wherein points G1, G2, G3, G4, G5 respectively represent the lowest extremity of trochlear groove for each slice 1-5. By connecting the various points G1, G2, G3, G4, G5, a point O can be obtained. As can be understood from FIGS. 3B and 6D, resulting line GO is perpendicular or nearly perpendicular to tangent line $P_1P_2$. In a 90° knee extension in FIG. 3B, line GO is perpendicular or nearly perpendicular to the joint line of the knee and line $P_1P_2$. As shown in FIG. 6C, each of the slices 6-8 can be aligned vertically along the trochlear groove, wherein points H6, H7, H8 respectively represent the lowest extremity of the trochlear groove for each slice 6-8. By connecting the various points H6, H7, H8, the point O can again be obtained. As can be understood from FIGS. 3A and 6D, resulting line HO is perpendicular or nearly perpendicular to tangent line $D_1D_2$. In a 0° knee extension in FIG. 3A, line HO is perpendicular or nearly perpendicular to the joint line of the knee and line $D_1D_2$.

As illustrated in FIG. 6D, the verification of the accuracy of the restoration process includes determining if the reference lines GO and HO are within certain tolerances with respect to being parallel to certain lines and perpendicular to certain lines. The line GO, as the reference across the most distal extremity of the trochlear groove of the femur and in a 90° knee extension, should be perpendicular to tangent line $D_1D_2$. The line HO, as the reference across the most posterior extremity of trochlear groove of the femur and in a 0° knee extension, should be perpendicular to tangent line $P_1P_2$.

Line HO and line $P_1P_2$ may form a plane S, and lines GO and line $D_1D_2$ may form a plane P that is perpendicular to plane S and forms line SR therewith. Line HO and line GO are parallel or nearly parallel to each other. Lines $P_1P_2$, $D_1D_2$ and SR are parallel or nearly parallel to each other. Lines $P_1P_2$, $D_1D_2$ and SR are perpendicular or nearly perpendicular to lines HO and GO.

As can be understood from FIG. 6D, in one embodiment, lines HO and GO must be within approximately three degrees of being perpendicular with lines $P_1P_2$, and $D_1D_2$ or the restored bones models 28A, 28B will be rejected and the restoration process will have to be repeated until the resulting restored bone models 28A, 28B meet the stated tolerances, or there has been multiple failed attempts to meet the tolerances ([block 230]-[block 240] of FIG. 2). Alternatively, as can be understood from FIG. 6D, in another embodiment, lines HO and GO must be within approximately six degrees of being perpendicular with lines $P_1P_2$, and $D_1D_2$ or the restored bones models 28A, 28B will be rejected and the restoration process will have to be repeated until the resulting restored bone models 28A, 28B meet the stated tolerances, or there has been multiple failed attempts to meet the tolerances ([block 230]-[block 240] of FIG. 2). If multiple attempts to provide restored bone models 28A, 28B satisfying the tolerances have been made without success, then bone restoration reference data may be obtained from another similar joint that is sufficiently free of deterioration. For example, in the context of knees, if repeated attempts have been made without success to restore a right knee medial femur condyle and tibia plateau from reference information obtained from the right knee lateral sides, then reference data could be obtained from the left knee lateral or medial sides for use in the restoration process in a manner similar to described above.

In some embodiments, as depicted in the table illustrated in FIG. 7, some OA knee conditions are more likely to be restored via the methods disclosed herein than other conditions when it comes to obtaining the reference data from the same knee as being restored via the reference data. For example, the damaged side of the knee may be light (e.g., no bone damage or bone damage less than 1 mm), medium (e.g., bone damage of approximately 1 mm) or severe (e.g., bone damage of greater than 1 mm). As can be understood from FIG. 7, the bone restoration provided via some of the above-described embodiments may apply to most OA patients having light-damaged knees and medium-damaged knees and some OA patients having severe-damaged knees, wherein restoration data is obtained from a reference side of the knee having the damaged side to be restored. However, for most OA patients having severe-damaged and some OA patients having medium-damaged knees, in some embodiments as described below, bone restoration analysis entails obtaining restoration data from a good first knee of the patient for application to, and restoration of, a bad second knee of the patient.

It should be understood that the indications represented in the table of FIG. 7 are generalities for some embodiments disclosed herein with respect to some patients and should not be considered as absolute indications of success or failure with respect to whether or not any one or more of the embodiments disclosed herein may be successfully applied to an individual patient having any one of the conditions (light, medium, severe) reflected in the table of FIG. 7. Therefore, the table of FIG. 7 should not be considered to limit any of the embodiments disclose herein.

f. Further Discussion of Bone Model Restoration Methods

Figure 8A:
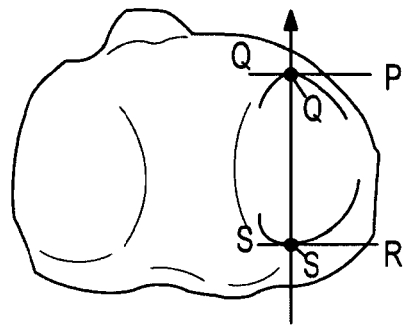
FIGS. 8A-8D are various views of the tibia plateau with reference to restoration of a side thereof.

For further discussion regarding embodiments of bone model restoration methods, reference is made to FIGS. 8A-8D. FIG. 8A shows the construction of reference line SQ in a medial portion of the tibia plateau. In one embodiment, the reference line SQ may be determined by superimposing an undamaged femoral condyle ellipse onto the medial tibia plateau to obtain two tangent points Q and S. In another embodiment, the tangent points Q and S may be located from the image slices by identifying the highest points at the posterior and anterior edges of the medial tibia plateau. By identifying tangent points Q and S, the tangent lines QP and SR may be determined by extending lines across each of the tangent points Q and S, wherein the tangent lines QP and SR are respectively tangent to the anterior and posterior curves of the medial tibia plateau. Reference line SQ may be obtained where tangent line QP is perpendicular or generally perpendicular to reference line SQ and tangent line SR is perpendicular or generally perpendicular to reference line SQ.

Figure 8B:
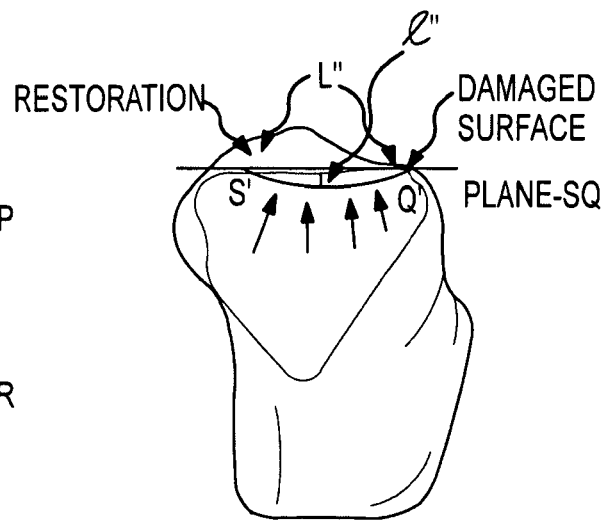

FIG. 8B shows the restoration of a damaged anterior portion of the lateral tibia plateau. The reference vector line or the vector plane is obtained from FIG. 8A, as line SQ or plane SQ. The reference vector plane SQ from the medial side may be applied as the reference plane in the damaged lateral side of the tibia plateau surface. In FIG. 8B, the contour of the damaged anterior portion of the lateral tibia plateau may be adjusted to touch the proximity of the reference vector plane SQ from the undamaged medial side. That is, points S' and Q' are adjusted to reach the proximity of the plane SQ. The outline between points S' and Q' are adjusted and raised to the reference plane SQ. By doing this adjustment, a restored tangent point Q' may be obtained via this vector plane SQ reference.

Figure 8C:
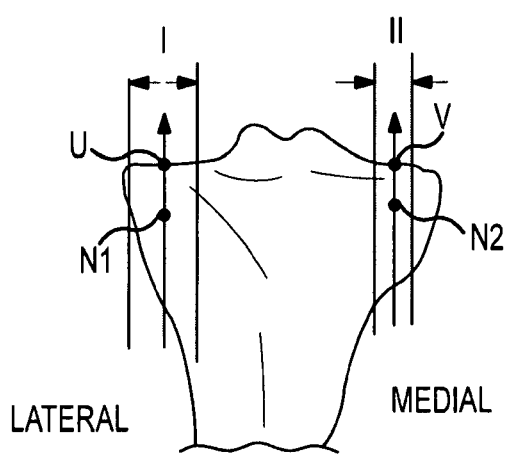
Figure 8D:
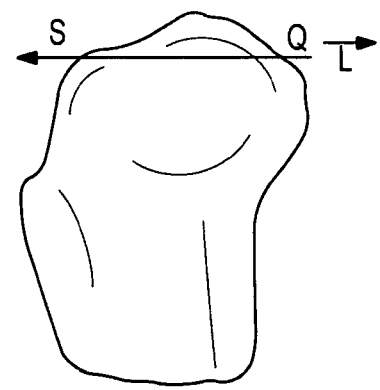

As shown in FIG. 8D, the reference vector plane SQ in the medial side is parallel or nearly parallel to the restored vector plane S'Q' in the lateral side. In FIG. 8B, the length L" represents the length of line S'Q'. The length l" is the offset from the recessed surface region of the tibia plateau to the plane S'Q' after the restoration. In the bone restoration assessment, the ratio of l"/L" may be controlled to be less than 0.01.

FIG. 8C is the coronal view of the restored tibia after 3D reconstruction, with a 0° knee extension model. The points U and V represent the lowest extremity of tangent contact points on each of the lateral and medial tibia plateau, respectively. In one embodiment, tangent points U and V are located within the region between the tibia spine and the medial and lateral epicondyle edges of the tibia plateau, where the slopes of tangent lines in this region are steady and constant. In one embodiment, the tangent point U in the lateral plateau is in area I between the lateral side of lateral intercondylar tubercule to the attachment of the lateral collateral ligament. For the medial portion, the tangent point V is in area II between the medial side of medial intercondylar tubercule to the medial condyle of tibia, as shown in FIG. 8C.

As previously stated, FIG. 8C represents the restored tibia models and, therefore, the reference lines N1 and N2 can apply to the restored tibia model in FIG. 8C, when the knee is at 0° extension. As can be understood from FIG. 8C, line N1 when extended across point U is perpendicular or generally perpendicular to line-UV, while line N2 when extended across point V is perpendicular or generally perpendicular to line UV. In restored the tibia model, line UV may be parallel or nearly parallel to the joint line of the knee. Within all these reference lines, in one embodiment, the tolerable range of the acute angle between nearly perpendicular or nearly parallel lines or planes may be within an absolute 6-degree angle, |x−x'|<6°. If the acute angle difference from FIG. 8C is less than 6°, the numerical data for the femur and/or tibia restoration is acceptable. This data may be transferred to the further assess the varus/valgus alignment of the knee models.

Figure 9A:
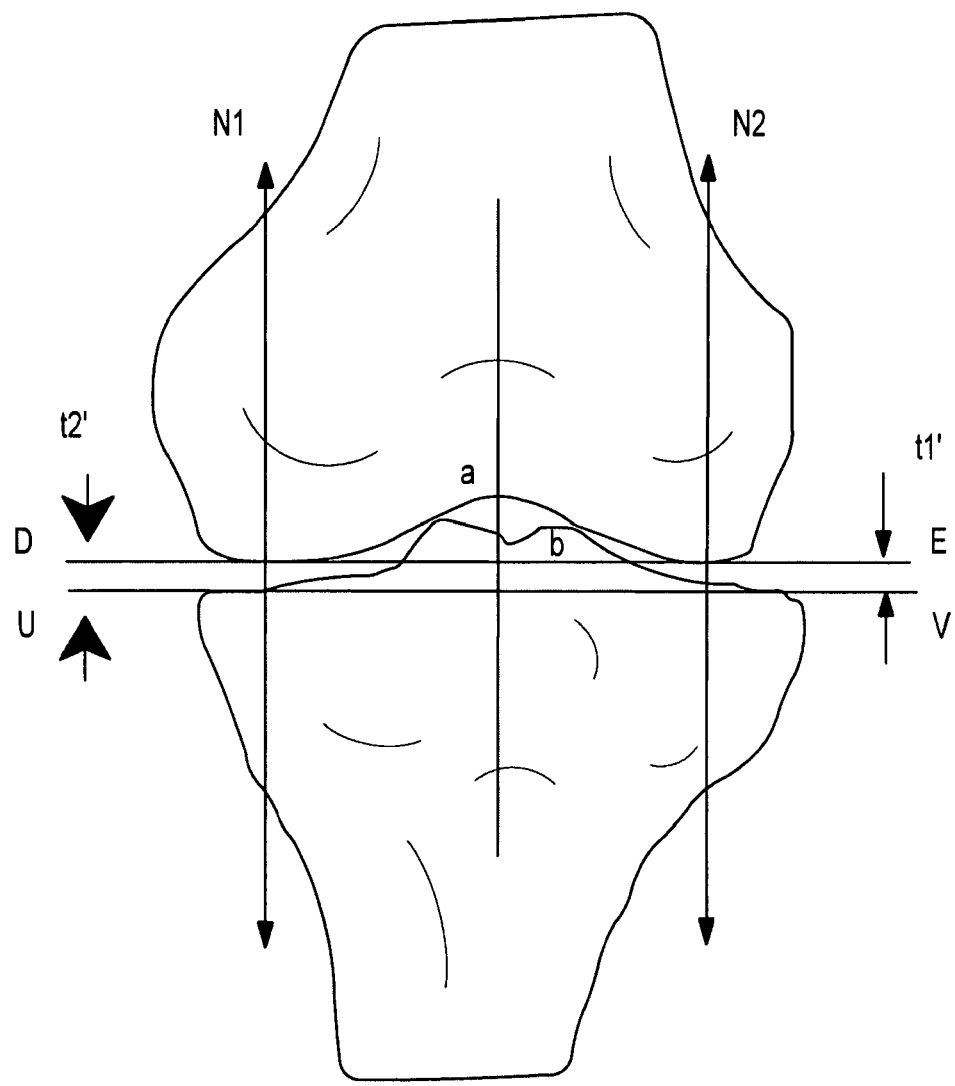
FIGS. 9A and 9B are, respectively, coronal and sagital views of the restored bone models.

FIG. 9A is a coronal view of the restored knee models of proximal femur and distal tibia with 0° extension of the knee. Line ab extends across the lowest extremity of trochlear groove of the distal femur model. Reference lines N1 and N2 are applied to the restored knee model of varus/valgus alignment, where line-N1 is parallel or generally parallel to line N2 and line ab. Depending on the embodiment, the acute angles between these lines may be controlled within a 3 degree range or a 5 degree range. The tangent points D and E represent the lowest extremities of the restored proximal femur model. The tangent points U and V are obtained from the restored distal tibia plateau surface. In the medial portion, t1' represents the offset of the tangent lines between the medial condyle and medial tibia plateau. In the lateral portion, t2' represents the offset of the tangent lines between the lateral condyle and lateral tibia plateau. In the varus/valgus rotation and alignment, t1' is substantially equal to t2', or |t1'−t2'|<<1 mm. Therefore, line DE may be generally parallel to the joint line of the knee and generally parallel to line UV.

Figure 9B:
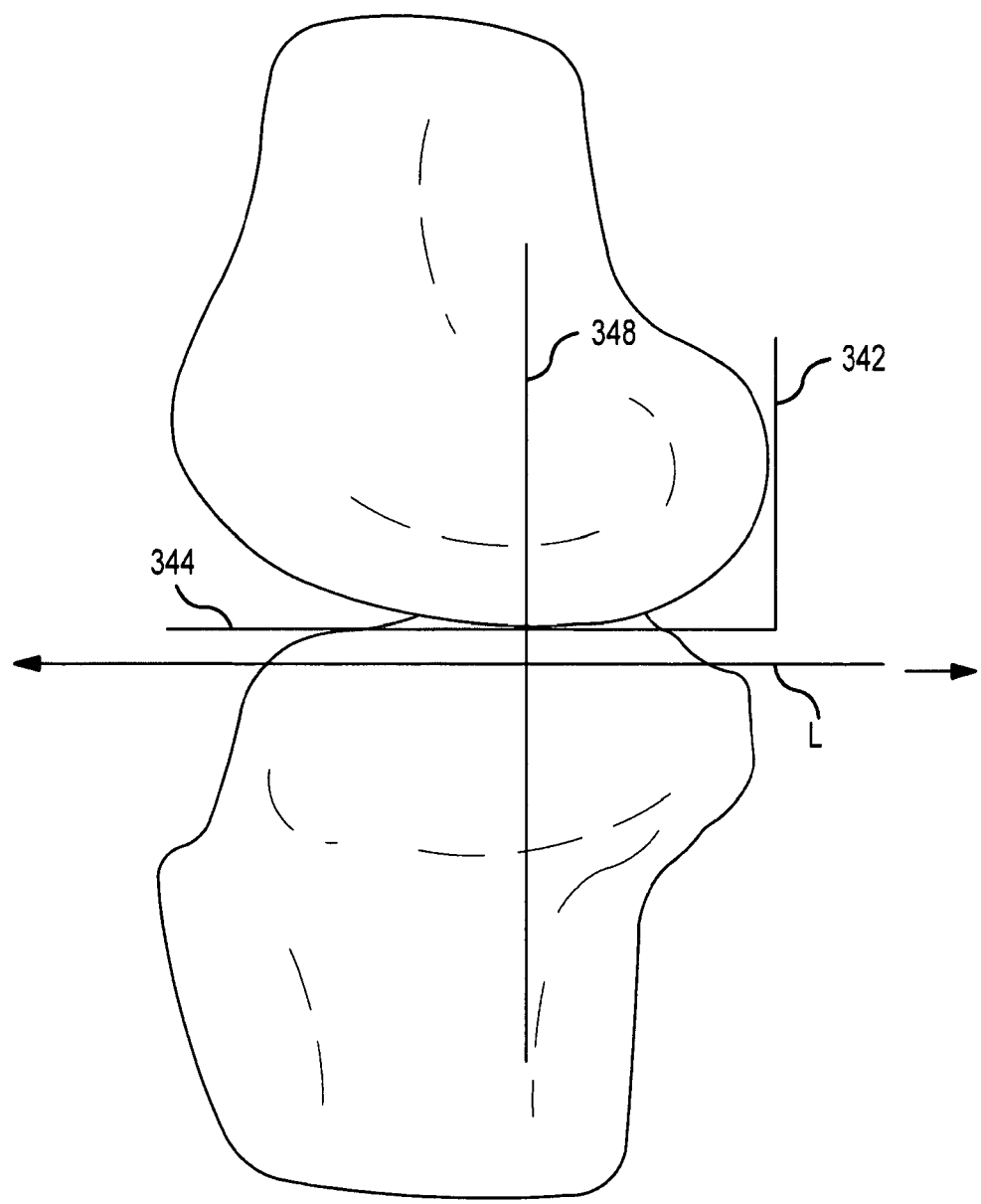

FIG. 9B is a sagital view of the restored knee models. Line 348 represents the attachment location of lateral collateral ligament which lies on the lateral side of the joint. Line 342 represents the posterior extremity portion of the lateral femoral condyle. Line 344 represents the distal extremity portion of the lateral condyle. In this restored knee model, line 344 may be parallel or generally parallel to line L. That is, plane 344 is parallel or generally parallel to plane L and parallel or generally parallel to the joint plane of the knee. In one embodiment, the tolerable range of acute angle between these planes may be controlled within an absolute 6 degrees. If the angle is less than an absolute 6 degrees, the information of the femur and tibia model will then be forwarded to the preoperative design for the implant modeling. If the acute angle is equal or larger than an absolute 6 degrees, the images and 3D models will be rejected. In this situation, the procedure will be returned to start all over from the assessment procedure of reference lines/planes.

g. Using Reference Information From a Good Joint to Create a Restored Bone Model For a Damaged Joint As mentioned above with respect to the table of FIG. 7, the knee that is the target of the arthroplasty procedure may be sufficiently damaged on both the medial and lateral sides such that neither side may adequately serve as a reference side for the restoration of the other side. In a first embodiment and in a manner similar to that discussed above with respect to FIGS. 2-6D, reference data for the restoration of the deteriorated side of the target knee may be obtained from the patient's other knee, which is often a healthy knee or at least has a healthy side from which to obtain reference information. In a second embodiment, the image slices of the healthy knee are reversed in a mirrored orientation and compiled into a restored bone model representative of the deteriorated knee prior to deterioration, assuming the patient's two knees where generally mirror images of each other when they were both healthy. These two embodiments, which are discussed below in greater detail, may be employed when the knee targeted for arthroplasty is sufficiently damaged to preclude restoration in a manner similar to that described above with respect to FIGS. 2-6D. However, it should be noted that the two embodiments discussed below may also be used in place of, or in addition to, the methods discussed above with respect to FIGS. 2-6D, even if the knee targeted for arthroplasty has a side that is sufficiently healthy to allow the methods discussed above with respect to FIGS. 2-6D to be employed.

Figure 10A:
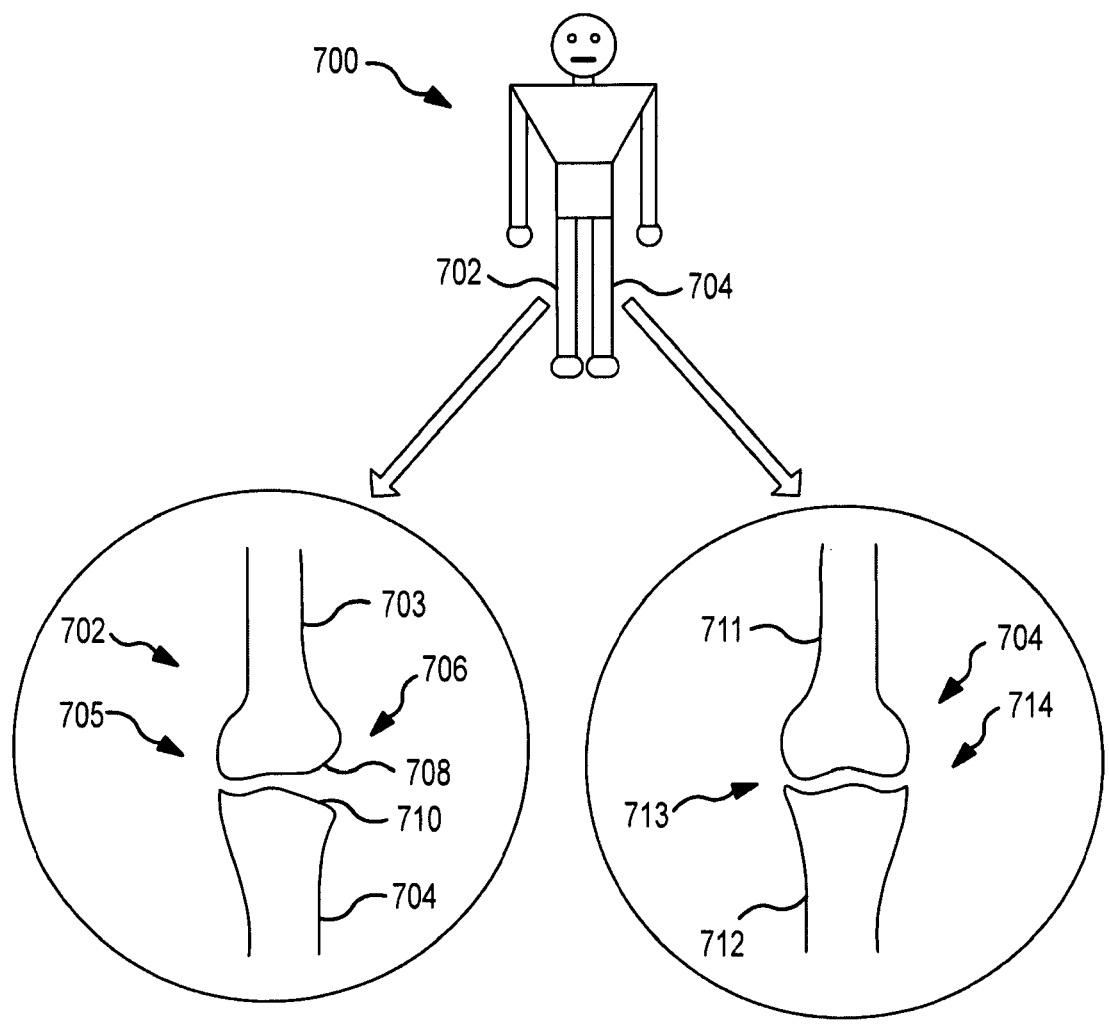
FIG. 10A is a diagram illustrating the condition of a patient's right knee, which is in a deteriorated state, and left knee, which is generally healthy.
Figure 10B:
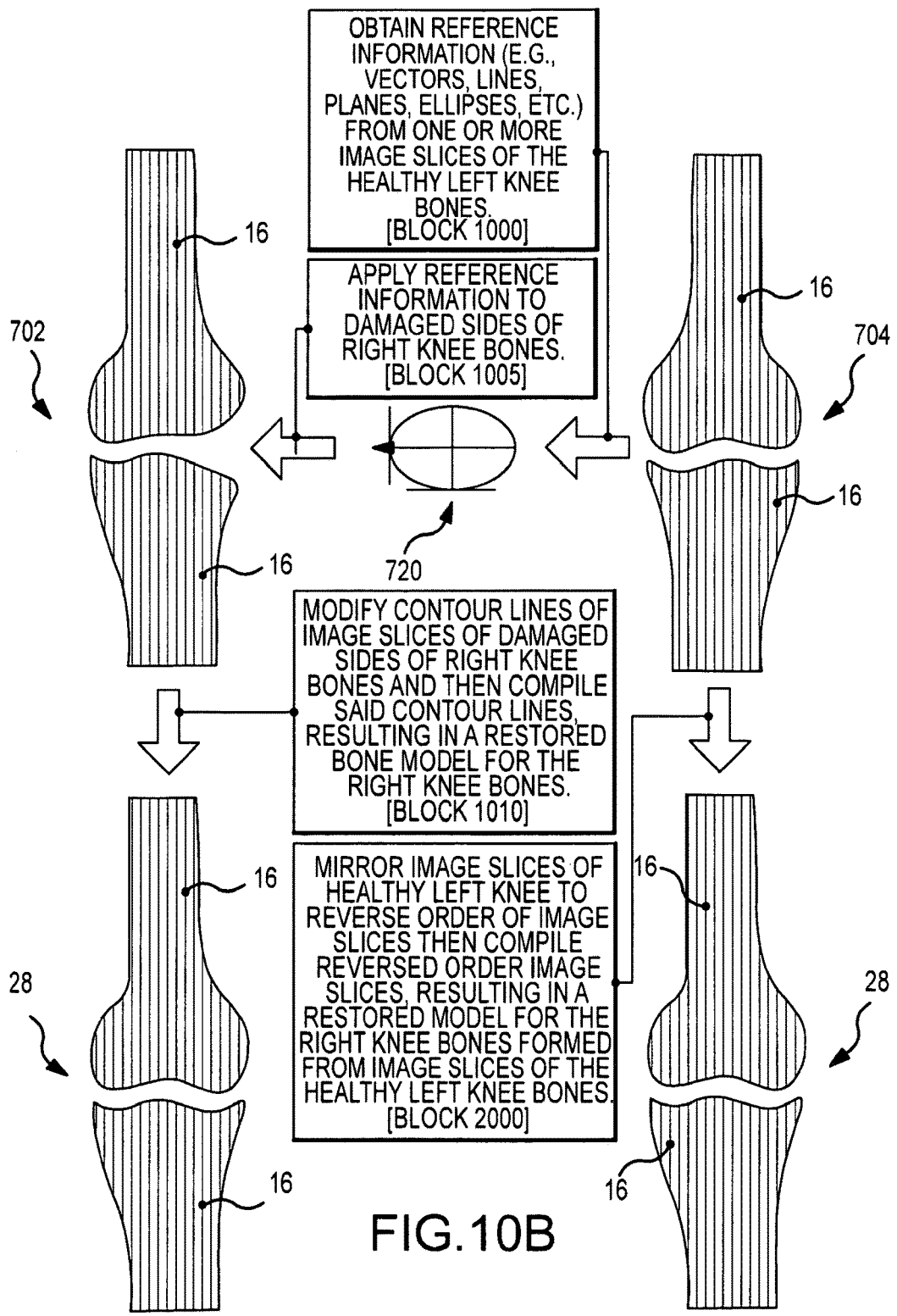
FIG. 10B is a diagram illustrating two options for creating a restored bone model for a deteriorated right knee from image slices obtained from a healthy left knee.

For a discussion of the two embodiments for creating a restored bone model for a deteriorated knee targeted for arthroplasty from image slices obtained from a healthy knee, reference is made to FIGS. 10A and 10B. FIG. 10A is a diagram illustrating the condition of a patient's right knee, which is in a deteriorated state, and left knee, which is generally healthy. FIG. 10B is a diagram illustrating the two embodiments. While in FIGS. 10A and 10B and the following discussion the right knee 702 of the patient 700 is designated as the deteriorate knee 702 and the left knee 704 of the patient 700 is designated as the healthy knee 704, of course such designations are for example purposes only and the conditions of the knees could be the reverse.

As indicated in FIG. 10A, the patient 700 has a deteriorated right knee 702 formed of a femur 703 and a tibia 707 and which has one or both of sides in a deteriorated condition. In this example, the lateral side 705 of the right knee 702 is generally healthy and the medial side 706 of the right knee 702 is deteriorated such that the right medial condyle 708 and right medial tibia plateau 710 will need to be restored in any resulting restored bone model 28. As can be understood from FIG. 10A, the patient also has a left knee 704 that is also formed of a femur 711 and a tibia 712 and which has a medial side 713 and a lateral side 714. In FIG. 10A, both sides 713, 714 of the left knee 704 are generally healthy, although, for one of the following embodiments, a single healthy side is sufficient to generate a restored bone model 28 for the right knee 702.

As indicated in FIG. 10B, image slices 16 of the deteriorated right knee 702 and healthy left knee 704 are generated as discussed above with respect to FIGS. 1A and 1B. In the first embodiment, which is similar to the process discussed above with respect to FIGS. 2-6D, except the process takes place with a deteriorated knee and a health knee as opposed to the deteriorated and healthy sides of the same knee, reference information (e.g., vectors, lines, planes, ellipses, etc. as discussed with respect to FIGS. 2-6D) 720 is obtained from a healthy side of the healthy left knee 704 [block 1000 of FIG. 10B]. The reference information 720 obtained from the image slices 16 of the health left knee 704 is applied to the deteriorated sides of the right knee 702 [block 1005 of FIG. 10B]. Specifically, the applied reference information 720 is used to modify the contour lines of the images slices 16 of the deteriorated sides of the right knee 702, after which the modified contour lines are compiled, resulting in a restored bone model 28 that may be employed as described with respect to FIG. 1C. The reference information 720 obtained from the healthy left knee image slices 16 may be coordinated with respect to position and orientation with the contour lines of the deteriorated right knee image slices 16 by identifying a similar location or feature on each knee joint that is generally identical between the knees and free of bone deterioration, such as a point or axis of the femur trochlear groove or tibia plateau spine.

In the second embodiment, image slices 16 are generated of both the deteriorate right knee 702 and healthy left knee 704 as discussed above with respect to FIG. 1B. The image slices 16 of the deteriorated right knee 702 may be used to generate the arthritic model 36 as discussed above with respect to FIG. 1D. The image slices 16 of the healthy left knee 704 are mirrored medially/laterally to reverse the order of the image slices 16 [block 2000 of FIG. 10B]. The mirrored/reversed order image slices 16 of the healthy left knee 704 are compiled, resulting in a restored bone model 28 for the right knee 702 that is formed from the image slices 16 of the left knee 704 [block 2000 of FIG. 10B]. In other words, as can be understood from [block 2000] and its associated pictures in FIG. 10B, by medially/laterally mirroring the image slices 16 of left knee 704 to medially/laterally reverse their order and then compiling them in such a reversed order, the image slices 16 of the left knee 704 may be formed into a bone model that would appear to be a bone model of the right knee 702 in a restored condition, assuming the right and left knees 702, 704 were generally symmetrically identical mirror images of each other when both were in a non-deteriorated state.

To allow for the merger of information (e.g., saw cut and drill hole data 44 and jig data 46) determined respectively from the restored bone model 28 and the arthritic model 28 as discussed above with respect to FIG. 1E, the restored bone model 28 generated from the mirrored image slices 16 of the healthy left knee 704 may be coordinated with respect to position and orientation with the arthritic model 36 generated from the image slices 16 of the deteriorated right knee 702. In one embodiment, this coordination between the models 28, 36 may be achieved by identifying a similar location or feature on each knee joint that is generally identical between the knees and free of bone deterioration, such as a point or axis of the femur trochlear groove or tibia plateau spine. Such a point may serve as the coordination or reference point P' ($X_{O-k}$, $Y_{O-k}$, $Z_{O-k}$) as discussed with respect to FIG. 1E.

While the two immediately preceding embodiments are discussed in the context of knee joints, these embodiments, like the rest of the embodiments disclosed throughout this Detailed Description, are readily applicable to other types of joints including ankle joints, hip joints, wrist joints, elbow joints, shoulder joints, finger joints, toe joints, etc., and vertebrae/vertebrae interfaces and vertebrae/skull interfaces. Consequently, the content of this Detailed Description should not be interpreted as being limited to knees, but should be consider to encompass all types of joints and bone interfaces, without limitation.

Although the present invention has been described with reference to preferred embodiments, persons skilled in the art will recognize that changes may be made in form and detail without departing from the spirit and scope of the invention.

What is claimed is:

1. A method of generating a computerized bone model representative of at least a portion of a first patient bone in a pre-degenerated state, the method comprising:
   receiving at least one first image of the first patient bone in a degenerated state at at least one computer linked with at least one medical imaging system, the at least one first image generated with the at least one medical imaging system and comprising a degenerated portion corresponding to a generally degenerated portion of the first patient bone in the degenerated state;
   receiving at least one second image of a second patient bone in a pre-degenerated state at the at least one computer linked with the at least one medical imaging system, the at least one second image generated with the at least one medical imaging system and comprising a reference portion corresponding to a generally non-degenerated portion of the second patient bone in the pre-degenerated state;
   using the at least one computer, modifying at least one aspect associated with the degenerated portion of the at least one first image with information from the at least one second image associated with the reference portion;
   using the at least one computer, generating the computerized bone model of the first patient bone with the modified degenerated portion of the at least one first image; and
   outputting instructions for restoring the first patient bone to the pre-degenerated state using the computerized bone model.

2. The method of claim 1, wherein the first patient bone is part of a first joint and the second patient bone is part of a second joint.

3. The method of claim 1, wherein the at least one aspect includes at least one contour line.

4. The method of claim 3, wherein the at least one contour line represents a contour line along a bone surface of the first patient bone.

5. The method of claim 3, wherein the at least one contour line represents at least one of a contour line along a bone surface of the first patient bone and a contour line along a cartilage surface of the first patient bone.

6. The method of claim 3, wherein the computerized bone model includes at least the following: at least one contour line associated with the at least one first image associated with a generally non-degenerated portion; and the modified at least one contour line associated with the at least one first image associated with the generally degenerated portion.

7. The method of claim 6, wherein the computerized bone model represents bone only.

8. The method of claim 6, wherein the computerized bone model represents at least one of bone or cartilage.

9. The method of claim 1, wherein the information includes at least one of ellipse information, circle information, line information, plane information, and vector information.

10. The method of claim 1, wherein the information includes vector information.

11. The method of claim 1, wherein the information pertains to a characteristic of at least one of a femur condyle or a tibia plateau.

12. The method of claim 1, wherein the at least one first and second images are generated via at least one of MRI or CT.

13. The method of claim 1, wherein the first patient bone is at least one of a femur or a tibia.

14. The method of claim 1, further comprising verifying accuracy of the computerized bone model representative of the at least a portion of the first patient bone in the pre-degenerated state, the accuracy based on an analysis of a trochlear groove of the computerized bone model representative of the at least a portion of the first patient bone in the pre-degenerated state.

15. The method of claim 14, wherein the accuracy of the computerized bone model representative of the at least a portion of the first patient bone in the pre-degenerated state is acceptable if an axis extending along the trochlear groove of the computerized bone model representative of the at least a portion of the first patient bone in the pre-degenerated state is equal to or less than approximately six degrees of being perpendicular with a line associated with a joint line associated with the computerized bone model representative of the at least a portion of the first patient bone in the pre-degenerated state.

16. The method of claim 1, wherein the instructions include manufacturing instructions for the manufacture of a customized arthroplasty jig.

17. A method of generating a computerized bone model representative of at least a portion of a first patient bone in a pre-degenerated state, wherein the first patient bone is part of a first patient joint, the method comprising:
   receiving a plurality of images of a second patient bone of a second joint at at least one computer linked with a medical imaging system, the plurality of images generated by the medical imaging system, wherein the second bone is a generally symmetrical mirror image of the first patient bone and is in a generally non-degenerated state;
   mirroring, using the at least one computer, the plurality of images into a reversed order of the plurality images; and
   generating, using the at least one computer, the computerized bone model representative of the at least a portion of the first patient bone from the reversed order of the plurality of images.

18. The method of claim 17, wherein the first and second joints are knee joints.

19. The method of claim 17, wherein the first and second joints are selected from the group consisting of knee joints, elbow joints, hip joints, wrist joints, shoulder joints, and ankle joints.

20. The method of claim 17, wherein the plurality of images are generated via at least one of MRI or CT.

21. The method of claim 17, further comprising employing the computerized bone model representative of the at least a portion of the first patient bone in the pre-degenerated state in defining manufacturing instructions for the manufacture of a customized arthroplasty jig.

22. The method of claim 1, wherein the at least one medical imaging system comprises a first and a second medical imaging system, the at least one first image generated with the first medical imaging system, and the at least one second image generated with the second medical imaging system.

* * * * *